(12) United States Patent
Page

(10) Patent No.: US 11,424,025 B2
(45) Date of Patent: Aug. 23, 2022

(54) SYSTEMS AND METHODS FOR MEDICAL DEVICE MONITORING

(71) Applicant: GE Precision Healthcare LLC, Milwaukee, WI (US)

(72) Inventor: John Page, Verona, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 238 days.

(21) Appl. No.: 16/557,930

(22) Filed: Aug. 30, 2019

(65) Prior Publication Data

US 2021/0065888 A1 Mar. 4, 2021

(51) Int. Cl.
*G06F 3/048* (2013.01)
*G16H 40/40* (2018.01)
(Continued)

(52) U.S. Cl.
CPC .......... *G16H 40/40* (2018.01); *G06F 3/0482* (2013.01); *G06F 3/04847* (2013.01); *G06F 3/14* (2013.01);
(Continued)

(58) Field of Classification Search
CPC ..... A61B 5/0205; A61B 5/7275; A61B 5/746; A61B 5/002; A61B 5/0022; A61B 5/02055; A61B 5/029; A61B 5/08; A61B 5/742; A61B 5/7235; A61B 5/0002; A61B 5/14532; A61B 5/01; A61B 5/7475; A61B 5/021; A61B 5/0816; A61B 5/0833; A61B 5/1118; A61B 5/318; G16H 40/60;
(Continued)

(56) References Cited

U.S. PATENT DOCUMENTS 7,612,679 B1 * 11/2009 Fackler ................ A61B 5/7475
340/539.12
8,881,724 B2 * 11/2014 Choncholas .......... A61M 16/00
128/204.21

(Continued)

OTHER PUBLICATIONS

Page, J., "Systems and Methods for Graphical User Interfaces for Supervisory Application," U.S. Appl. No. 16/557,919, filed Aug. 30, 2019, 119 pages.

(Continued)

*Primary Examiner* — Steven B Theriault
(74) *Attorney, Agent, or Firm* — McCoy Russell LLP

(57) ABSTRACT

In an example, a system includes a computing device storing instructions executable to: receive an insight defined by a user, the insight dictating that a notification be output when a condition and a scope of the condition are met, the condition and the scope defined by the user; receive real-time medical device data determined from output from a plurality of medical devices monitoring a plurality of patients; determine if a set of values of one or more patient monitoring parameters of the medical device data meet the condition and the scope, and if so, output the notification for display on a display operably coupled to a first care provider device associated with the user; and responsive to a request from the user, adjust a privacy setting of the insight to allow the insight to be distributed to one or more additional care provider devices associated with other users.

17 Claims, 29 Drawing Sheets
(23 of 29 Drawing Sheet(s) Filed in Color)

(51) Int. Cl.
*G06F 3/0482* (2013.01)
*G06F 3/04847* (2022.01)
*G06F 3/14* (2006.01)
*G08B 21/18* (2006.01)

(52) U.S. Cl.
CPC .. *G08B 21/182* (2013.01); *G06F 2203/04803* (2013.01)

(58) Field of Classification Search
CPC ...... G16H 40/63; G16H 40/40; G06F 3/0482; G06F 3/04847; G06F 3/14; G06F 2203/04803; G08B 21/182
See application file for complete search history.

(56) References Cited

U.S. PATENT DOCUMENTS

| | | | | |
|---|---|---|---|---|
| 8,972,272 | B1* | 3/2015 | Dvorak | G16H 40/63 705/3 |
| 9,028,407 | B1* | 5/2015 | Bennett-Guerrero | A61B 5/4094 600/301 |
| 9,119,925 | B2* | 9/2015 | Vandine | A61M 16/0051 |
| 9,262,588 | B2* | 2/2016 | Skidmore | G16H 40/63 |
| 9,400,874 | B2* | 7/2016 | Powell | G16H 15/00 |
| 9,563,336 | B2* | 2/2017 | Barak | G06F 9/451 |
| 9,852,265 | B1* | 12/2017 | Treacy | A61B 5/746 |
| 10,204,081 | B2* | 2/2019 | Vann | G06F 40/106 |
| 10,226,200 | B2* | 3/2019 | Vassallo | G16H 40/63 |
| 10,387,612 | B2* | 8/2019 | Wu | G16H 50/20 |
| 10,420,480 | B1* | 9/2019 | Schermerhorn | A61B 5/743 |
| 10,463,315 | B2* | 11/2019 | Watson | A61B 5/14552 |
| 10,512,436 | B2* | 12/2019 | Muhsin | A61B 5/002 |
| 10,911,891 | B2* | 2/2021 | Brouse | H04W 4/023 |
| 2002/0183976 | A1* | 12/2002 | Pearce | G16H 40/67 702/188 |
| 2004/0054261 | A1* | 3/2004 | Kamataki | A61B 5/0002 600/300 |
| 2005/0109828 | A1* | 5/2005 | Jay | G06F 9/4451 235/375 |
| 2008/0103375 | A1* | 5/2008 | Kiani | A61B 5/14551 600/323 |
| 2008/0281168 | A1* | 11/2008 | Gibson | A61B 5/14551 600/301 |
| 2008/0314973 | A1* | 12/2008 | Zuhars | G16H 40/40 235/380 |
| 2009/0055735 | A1* | 2/2009 | Zaleski | G16H 40/63 715/700 |
| 2009/0099866 | A1* | 4/2009 | Newman | G16H 40/67 705/2 |
| 2010/0056883 | A1* | 3/2010 | Meschisen | G16H 40/40 600/301 |
| 2010/0152544 | A1* | 6/2010 | Weaver | G16H 15/00 600/300 |
| 2010/0249540 | A1* | 9/2010 | Lisogurski | G16H 40/20 600/301 |
| 2011/0004071 | A1* | 1/2011 | Faiola | G16H 15/00 600/300 |
| 2011/0071368 | A1* | 3/2011 | Baker, Jr. | A61B 5/7475 600/301 |
| 2011/0071420 | A1* | 3/2011 | St. Pierre | A61B 5/7475 600/549 |
| 2011/0118573 | A1* | 5/2011 | McKenna | A61B 5/7445 600/323 |
| 2011/0202490 | A1* | 8/2011 | Gawlick | G16H 40/67 706/47 |
| 2012/0029301 | A1* | 2/2012 | Battista, Jr. | G06F 19/00 600/300 |
| 2012/0310660 | A1* | 12/2012 | Liu | G16H 10/60 705/2 |
| 2013/0182107 | A1* | 7/2013 | Anderson | G06T 7/20 348/143 |
| 2014/0126770 | A1* | 5/2014 | Odessky | G06F 19/00 382/103 |
| 2014/0132413 | A1* | 5/2014 | Fox | G16H 40/20 340/573.1 |
| 2014/0266709 | A1* | 9/2014 | Nagase | G08B 25/10 340/539.13 |
| 2014/0266786 | A1* | 9/2014 | Sugiyama | G16H 40/63 340/870.4 |
| 2015/0137968 | A1* | 5/2015 | Rusin | G08B 25/001 340/506 |
| 2015/0205921 | A1* | 7/2015 | Dick | G06F 19/00 705/2 |
| 2015/0302539 | A1* | 10/2015 | Mazar | G16H 40/20 705/3 |
| 2015/0351695 | A1* | 12/2015 | Cronin | G16H 40/67 600/485 |
| 2015/0364022 | A1* | 12/2015 | Dyell | G16H 40/63 340/573.1 |
| 2016/0143598 | A1* | 5/2016 | Rusin | A61B 5/7435 340/573.1 |
| 2016/0361030 | A1* | 12/2016 | Buresh, II | G08B 3/10 |
| 2017/0000412 | A1* | 1/2017 | Scott | G16H 20/40 |
| 2017/0042488 | A1* | 2/2017 | Muhsin | A61B 5/0205 |
| 2017/0103175 | A1* | 4/2017 | Chopra | G16H 10/60 |
| 2018/0082036 | A1* | 3/2018 | Hanrahan | H04L 65/602 |
| 2018/0189946 | A1* | 7/2018 | Kusens | G06T 7/0016 |
| 2018/0193579 | A1 | 7/2018 | Hanrahan et al. | |
| 2019/0117070 | A1* | 4/2019 | Muhsin | A61B 5/0295 |
| 2019/0125278 | A1* | 5/2019 | Soosalu | G06T 11/206 |
| 2019/0139646 | A1* | 5/2019 | Roberts | G16H 50/70 |
| 2019/0311804 | A1* | 10/2019 | Boyer | G16H 40/67 |
| 2019/0320988 | A1* | 10/2019 | Ahmed | A61B 5/002 |
| 2019/0336085 | A1* | 11/2019 | Kayser | A61B 5/002 |
| 2021/0057111 | A1* | 2/2021 | Barkol | G16H 40/20 |
| 2021/0059616 | A1* | 3/2021 | Abrol | G16H 40/67 |
| 2021/0064224 | A1* | 3/2021 | Page | A61M 16/01 |
| 2021/0065888 | A1* | 3/2021 | Page | G06F 3/04847 |
| 2021/0065889 | A1* | 3/2021 | Page | G16H 40/63 |

OTHER PUBLICATIONS

Page, J., "Systems and Methods for Graphical User Interfaces for Medical Device Trends," U.S. Appl. No. 16/557,943, filed Aug. 30, 2019, 120 pages.

* cited by examiner

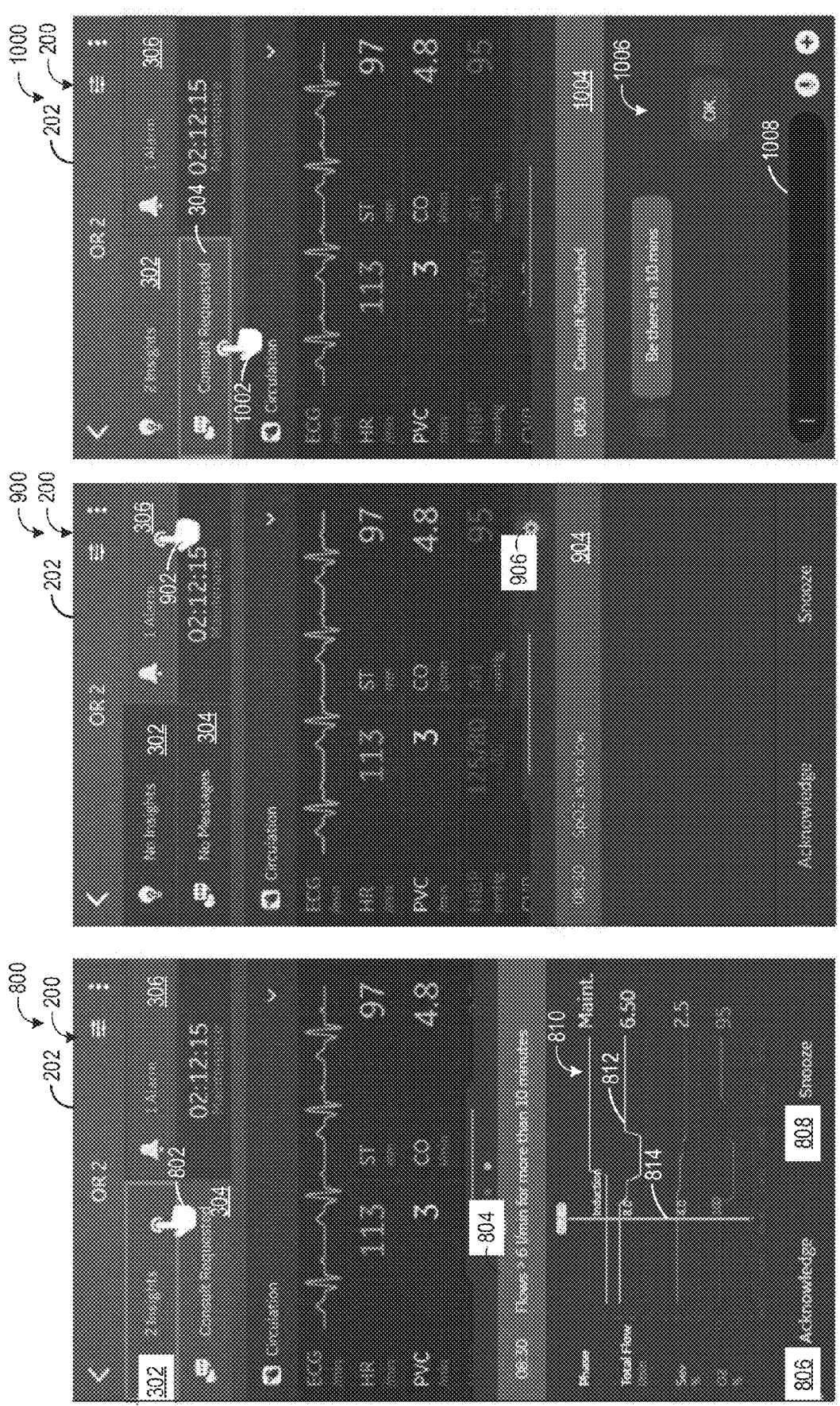

SYSTEMS AND METHODS FOR MEDICAL DEVICE MONITORING

FIELD

Embodiments of the subject matter disclosed herein relate to medical device monitoring, and more specifically to medical device monitoring during perioperative care.

BACKGROUND

Certain medical procedures, such as surgery, may require various sub-procedures to be performed to prep the patient for surgery, maintain the patient in a certain condition during surgery (e.g., anesthetized), and help the patient recover after surgery. Such sub-procedures that are performed in support of a main procedure may be referred to as perioperative care. Perioperative care of patients in a hospital or other medical facility may include multiple patient monitoring devices monitoring multiple patients. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the presentation of patient medical information to the care providers may require multiple time-consuming and cumbersome requests or searches for information.

BRIEF DESCRIPTION

In one embodiment, a system includes a computing device storing instructions executable to: receive an insight defined by a user, the insight dictating that a notification be output when a condition and a scope of the condition are met, the condition and the scope defined by the user; receive real-time medical device data determined from output from a plurality of medical devices monitoring a plurality of patients; determine if a set of values of one or more patient monitoring parameters of the medical device data meet the condition and the scope, and if so, output the notification for display on a display operably coupled to a first care provider device associated with the user; and responsive to a request from the user, adjust a privacy setting of the insight to allow the insight to be distributed to one or more additional care provider devices associated with other users.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below:

FIGS. 8-10 show the display device displaying various notifications output as part of the single-patient graphical user interface generated via the supervisory application.

DETAILED DESCRIPTION

Figure 1A:
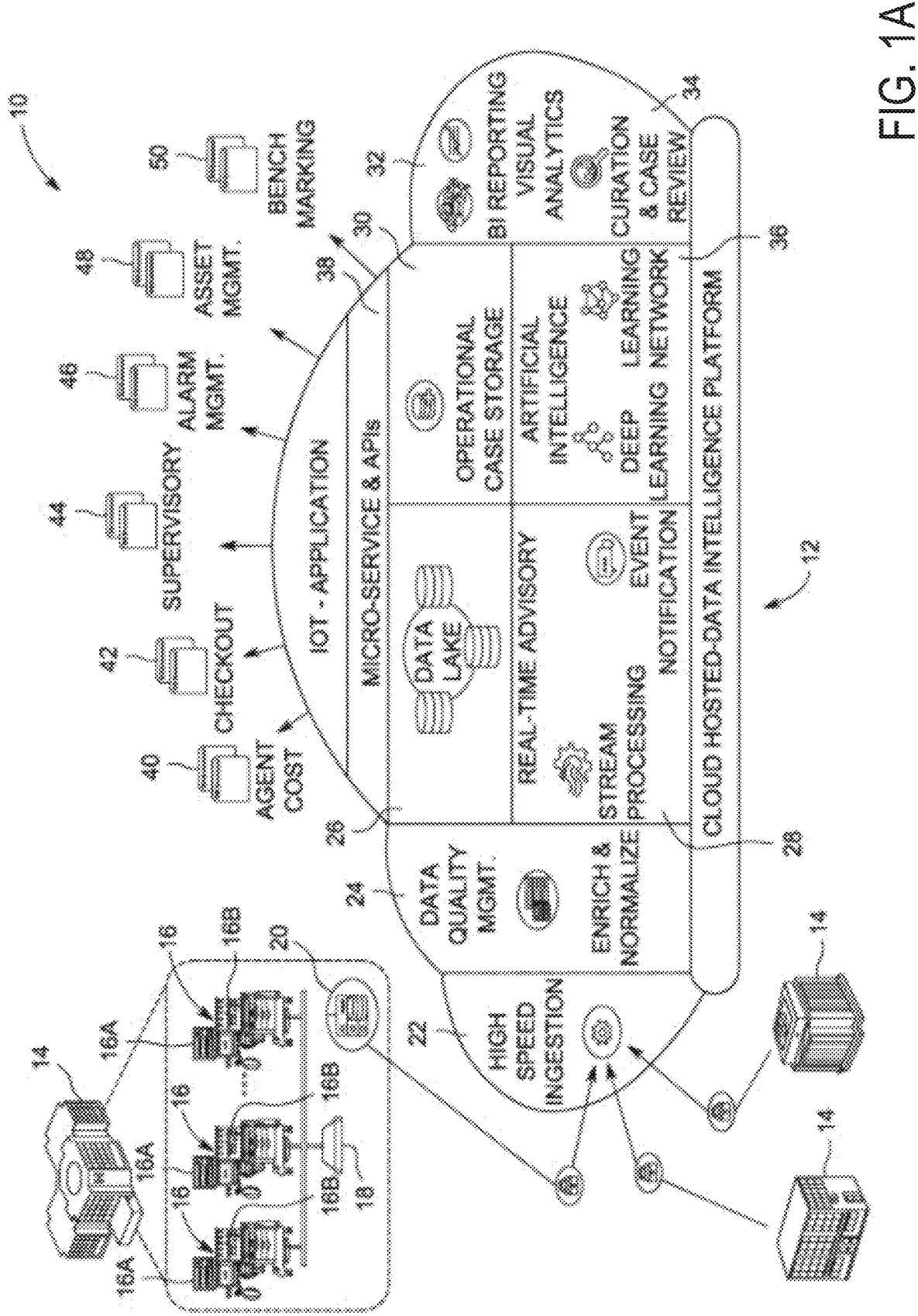
FIGS. 1A and 1B schematically show an example system for perioperative care and supervision including a supervisory application.

Embodiments of systems and methods as disclosed herein operate to facilitate perioperative care for a plurality of patients, and supervision of a plurality of care providers attending to the plurality of patients. To facilitate the perioperative care and supervision described herein, the systems and methods as disclosed herein collect and process a wide variety of medical device data. Medical device data includes physiological data (also referred to as patient monitoring data) that is acquired from a patient by a medical device and machine data collected internally from the medical device itself. Machine data may include alarms, device status, settings, messages, and measured operational data. Machine data may further include settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. Still further examples of the machine data include proactive or predictive service alerts from the medical device, maintenance checkout information, and/or processor clock cycle signals or power signals or other operational signals from various components of the medical device indicative that the medical device is turned on, in use, in operation, held in a stand by condition, or turned off.

The medical device data can be collected in time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical device. In embodiments, this increased velocity of the received data and the monitoring and analysis of medical device machine data can enable improved monitoring systems and methods as disclosed herein. As described in further detail herein, embodiments of systems and methods support high speed data ingestion, enrichment, normalization, and data curation of the medical device data. The medical device data can undergo real time analysis and further enrichment of the data with event detection and notation. While all of the medical device data can be saved for retrospective and automated machine learning and analysis, event detection and notation can be used to create further exemplary files of medical device data stemming from particular events or conditions which can be used as exemplary or case study data for further analysis.

The medical device data may be supplied to one or more care providers, such as a supervising anesthesiologist, nurse anesthesiologists, and other care providers. In particular, the medical device data may be supplied to the supervising anesthesiologist or other supervising care provider via a supervisory application that facilitates presentation of the medical device data in real-time or near real-time via one or more graphical user interfaces that may be displayed on a device of the supervising care provider, such as a mobile device (e.g., smart phone, tablet, wearable). The supervisory application may facilitate display of medical device data, including physiological data and medical device setting/parameter data, for a plurality of patients and for a plurality of different patient monitoring parameters to the supervising care provider. The displayed medical device data for the plurality of patients may be displayed simultaneously in a multi-patient graphical user interface (GUI), which may allow the supervising care provider to easily monitor patient status for each patient, even if the care provider is located away from the patient(s). When additional information for a specific patient is desired, the supervisory application may generate a single-patient GUI that provides more detailed medical device data for the patient.

The supervisory application may also monitor patient status, via the medical device data, and may output various notifications, such as alarms, when patient status changes or a specified patient monitoring parameter or combination of parameters (such as blood oxygenation) reaches a predefined condition relative to a threshold (e.g., drops below a threshold) or changes over time. The supervisory application may also facilitate communication between the supervising care provider and one or more subordinate care providers that may be in a room with a patient while the supervising care provider is located in a different room or area of the medical facility. For example, a subordinate care provider may send a request, via an in-room GUI of the supervisory application that is executed on a device of the subordinate care provider, for a consultation from the supervising care provider, which may be received by the supervising care provider's device and output to the supervising care provider via a GUI of the supervisory application. The in-room GUI may also facilitate text or voice messaging between the subordinate care provider and the supervising care provider.

The supervisory application may also generate a trends GUI that may be output on the supervising care provider's device. Via the trends GUI, the supervising care provider may assess, for a plurality of selected patient monitoring parameters, change in medical device data over time. The trend for each selected patient monitoring parameter may be displayed simultaneously in a time-aligned fashion. Further, a relative change in each patient monitoring parameter over a specified time duration may be determined and displayed in response to a single user input.

The various GUIs and functions of the supervisory application described above may allow for a single supervising care provider to simultaneously monitor multiple patients during respective medical procedures, such as surgery. While each patient may be attended to by multiple care providers during the medical procedure, such as one or more surgeons, nurses, medical technicians, etc., certain supervising care providers, such as anesthesiologists, may attend to multiple patients at once and may oversee a plurality of subordinate care providers, such as nurse anesthesiologists. As the number of subordinate care providers increases relative to the number of supervising care providers, and as medical procedures become more complex, the need for a supervising care provider to be able to monitor patients and oversee subordinate care providers remotely has increased. For example, a supervising anesthesiologist may be scheduled to initiate and monitor an induction phase of anesthesia for a patient, which may demand the supervising anesthesiologist be in the operating room with the patient during that time. However, the supervising anesthesiologist may also be attending to six other patients that are in the maintenance phase of anesthesia, with each of the six other patients being monitored by an in-room nurse anesthesiologist. If an event were to occur to one of the six other patients that demanded the care of the supervising anesthesiologist, there may be a delay from when the supervising anesthesiologist is notified of the event to when the supervising anesthesiologist could actually arrive to care for the patient. However, via the supervisory application described herein, the supervising care provider may be able to monitor patient status for all patients from any location, and may be able to adjust medical therapy device settings and/or instruct subordinate care providers from afar. In doing so, patient care may be improved.

The supervisory application may facilitate the display of real-time medical device data obtained and/or determined from a plurality of medical devices monitoring a plurality of patients. The real-time medical device data may be displayed via various graphical user interfaces (GUIs). As an example, a single-patient GUI may be displayed on a care provider device (e.g., mobile phone, tablet, and/or wearable). Via the single-patient GUI, real-time medical device data for a patient may be displayed via a plurality of patient monitoring parameter tiles. The plurality of patient monitoring parameter tiles may be scalable, modular, and customizable by the user and/or by the supervisory application to allow for easy customizability, and ease of adding new patient monitoring parameters/medical device data in the future. For example, a user of the supervisory application (e.g., a care provider such as an anesthesiologist) may create a set of rules or an algorithm (where the rules or algorithm may be referred to as an insight) that may be executed using the real-time medical device data to determine a result (e.g., a determination of procedure phase, a prediction of patient state, a recommended course of action, etc.) or a notification of patient status. When the user selects to apply the insight, the result of the insight may be displayed as a tile on the patient-specific GUI going forward, and the other patient monitoring parameter tiles on the patient-specific GUI may be adjusted (e.g., moved, resized, scaled, and so forth) to accommodate the new insight result tile. As another example, the user may select to include a real time video feed from the patient's room as a tile in the single-patient GUI (larger variety), which may require a relatively large sized tile. The remaining tiles may be rearranged (whether automatically or in response to the user) to accommodate the larger tile.

Figure 1B:
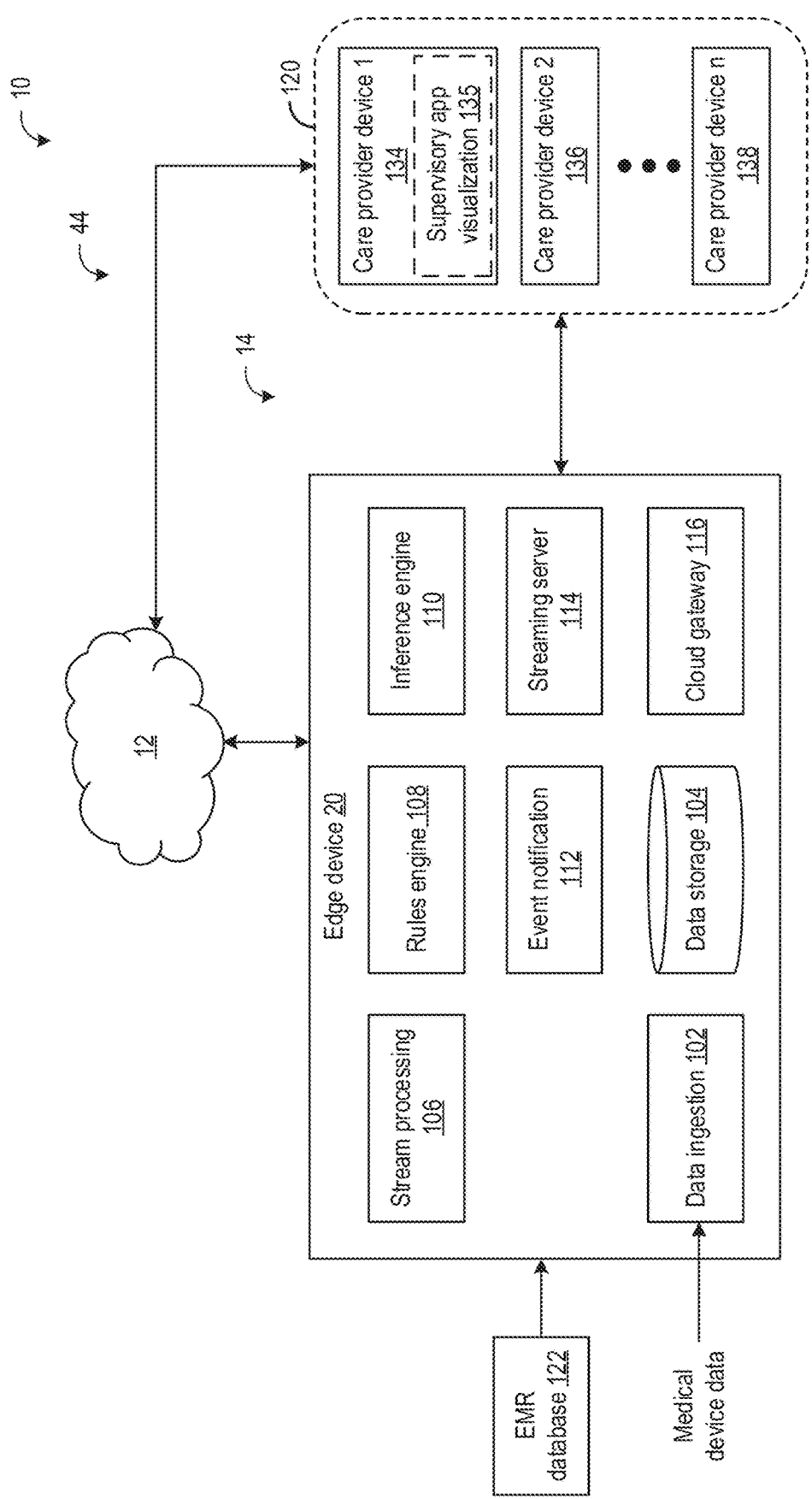

FIGS. 1A and 1B depict an exemplary embodiment of a system 10 for perioperative care and supervision. Referring first to FIG. 1A, system 10 includes a medical device data (MDD) processing system 12. The MDD processing system 12 can be implemented in a variety of hardware and/or software implementations and it should be noted that such implementations are not considered to be limiting. For example, it is contemplated that any or all of the MDD processing system 12 may be embodied exclusively in hardware, exclusively in software, exclusively in firmware or in any combination of hardware, software, and/or firmware. While the following describes exemplary methods and systems, the examples provided herein are not the only way to implement such methods and systems.

In embodiments wherein any of the claims are read to cover an entirely software and/or firmware implementation, in any embodiment, at least one of the elements is hereby expressly defined to include a tangible and non-transient computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g. for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the system 12 is implemented by one or more networked processors or computing devices. Processing system 12 may be implemented in a cloud computing platform and/or infrastructure. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; wired or wireless (e.g. optical, Bluetooth, radio frequency (RF) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments, while individual hospitals or groups of hospitals may use the MDD processing system 12, the MDD processing system 12 may receive and process information from a plurality of hospital networks including those unaffiliated with one another at the same time.

As depicted in FIG. 1A, the hospital network 14 includes a plurality of medical devices 16. The medical devices 16 may include physiological monitoring devices 16a as well as patient therapy devices 16b. Physiological monitoring devices 16a may include, but are not limited to, heart rate monitors, blood pressure oxygenation monitors, respiration monitors, ECG monitors, EEG monitors, or EMG monitors. An exemplary embodiment of an anesthesia delivery machine will be used for discussion purposes as the medical device, and more specifically as the patient therapy device 16b, although it will be recognized by a person of ordinary skill in the art that other devices, including but not limited to patient respiratory assistance devices or dialysis machines, may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In some embodiments, imaging devices, including but not limited to X-ray, CT, MM, and ultrasound devices, may be examples of medical devices 16 as contemplated within the present disclosure. Still further examples of medical devices may include video and/or audio recording devices.

In an exemplary embodiment, a limited version of the MDD processing system 12 as described herein may be implemented locally, for example as an anesthesia delivery management system 18. In such an embodiment, the anesthesia delivery management system 18 may operate to collect medical device data from a plurality of anesthesia delivery machines 16b inter alia to monitor anesthesia agent use between anesthesia delivery machines and across procedures performed by the anesthesia delivery machines in an effort to visualize anesthetic agent consumption and use as well as to quantify, monitor, and evaluate trends across all of the anesthesia delivery machines in the hospital or surgical unit.

The medical devices 16 may be communicatively connected to one or more edge devices, such as edge device 20. Edge device 20 may exemplarily be an edge processing device, cloud processing device, or internet gateway. The edge device 20 may include an internet of things (IOT) gateway which facilitates a secure communications link between the medical devices 16 at the hospital network 14 with the servers, processors, and computer readable media implementing the MDD processing system 12. In exemplary embodiments, the edge device 20 may communicate directly with one or more of the medical devices 16, or may communicate with the medical devices 16 through an intermediate network, for example, the anesthesia delivery management system 18 or another medical device data system or network.

The edge device 20 receives the medical device data as time series data for any of the medical device data available from the medical devices. As noted above, the data streams of medical device data (e.g., machine data, monitored patient physiological parameter data) are available in time series format as acquired from the medical devices and may include, but are not limited to time series information of alarms, device status, device settings, messages, and measured data. In embodiments, the medical devices may be equipped with sensors that improve the self-awareness of the medical device, e.g. sensors that monitor the function, inputs and/or outputs of various components of the medical device itself. Many such sensors are already incorporated into medical devices such as to measure compressor speeds and/or cycle times, internal pressures, voltages, clock speeds, or temperatures, or other sensors as will be recognized by a person of ordinary skill in the art or as disclosed in further detail herein.

The edge device 20 encrypts the time series formatted data and the encrypted data is transmitted using wired and/or wireless communication techniques for encrypted data to the server, processors, and data storage carrying out the MDD processing system 12. The edge device 20 continuously transmits de-identified medical device data in time series format over an encrypted communication channel to a high speed data ingestion module 22 of the MDD processing system 12. While the exemplary embodiment described herein may reference de-identified data, it will be recognized that other embodiments may use patient-identified data with appropriate considerations taken for handling patient data. The high speed data ingestion module 22 takes in the real time streams of medical device data. The data ingestion can be performed in an automated fashion and can preprocess the received streams of real time data in the time series for later processing by the MDD processing system 12. The high speed ingestion module 22 can receive concurrent data streams from multiple connected devices across multiple sites at a high incoming velocity, for example at or near the frequency at which medical devices can output data. In exemplary embodiments the high speed ingestion module 22 is scalable to continue to ingest increased bandwidth of medical device data without significant decrease in ingestion speeds.

The high speed ingestion module 22 takes the time series medical device data from the medical devices of one or more hospital networks and formats it for further processing by a data quality management module 24. In exemplary and non-limiting embodiments, the high speed injection module 22 supports open standard such as ASTMF 2761 or integrated clinical environmental (ICE). The data quality management module 24 may normalize, enrich, and tag the data streams without negatively impacting data latency. In a healthcare environment, a variety of healthcare information products and/or systems may be used to provide medical services, collect medical data, conduct medical exams, etc. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.)) and various standards and/or protocols (e.g., cross-enterprise document sharing (XDS.A/B) cross-enterprise document media interchange (XDM) cross-enterprise document reliable interchange (XDR), patient identifier cross-referencing/patient demographics query (PIX/PDQ) patient administration management (PAM), query for existing data (QED), national counsel for prescription drug programs (NCPDP), etc.)) that make system integration and/or communication more difficult. Thus, normalization may include reformatting of medical data to a consistent or compatible format for use within the MDD processing system 12. In an exemplary embodiment, the medical device data may be normalized into the ISO/IEEE 11073-10101 nomenclature and its extensions. In a still further exemplary embodiment, the data quality management module 24 can normalize the streams of incoming time series data by converting units of measure. The data quality management module 24 can further operate to identify and tag various types of medical device data, locations from which the medical device data was received, or time series data streams originating from the same medical device. These tags can be used as further detailed herein to identify and analyze groups of streams of time series data.

In an exemplary embodiment, the data quality management module 24 normalizes the received incoming data by transforming and/or translating the clinical data streamed from the source healthcare system or device into a canonical data model with associated metadata. The processed medical device data is stored in a data lake 26 which is exemplarily implemented in computer readable storage embodying capability to store terabytes of data. The data lake 26 is a long-term computer storage repository that holds large amounts of raw data in a native format until the data is needed. The native format may include the time series data from the medical devices which may be in waveform or binary format, audio data, image data, and/or video data. In embodiments, this can help to facilitate the ingestion of the data that may not be processed in real time but may still be taken in in real time or near real time and instead stored in the data lake until further needed. This may be facilitated by identifying particular data streams and limiting the processing of those data streams, for example by the data quality management module 24, if it is known at that time that such data stream is not being used in real time analysis. In an exemplary embodiment, the data quality management module 24 may not convert the data to a canonical data model but may still attempt to tag, enrich, or index the data to facilitate later retrieval of that data in a standardized way from the data lake 26.

In a still further embodiment, portions of the data that are stored in the data lake 26 may also be additionally stored in a graph database which may be a separate database residing on the same computer readable storage, or may be embodied on separate computer readable storage from the data lake 26. The graph database may receive the data streams of which it is known that the system may analyze trends in that data stream. The graph database may store the streams of data in a time series format in a way that facilitates trending of the data over time and appending the data with events either identified in the data itself, in one or more of the other data streams, or received by the system from an external source. These events may include, but are not limited to, medical device or clinician actions, clinical events, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data may be provided to a stream processing engine 28. The stream processing engine 28 identifies cases and events in the time series streams of medical device data. Identified clinical cases may be stored in an operational case database 30. Clinical cases may exemplarily include surgical and intensive care unit (ICU) cases. The clinical cases may be identified by the medical device used and the timing of the medical data in the time series of the medical device data. For example, a time series of medical device data from an anesthesia delivery machine showing a change in status turning the machine on and followed by changes to device settings and delivery and/or consumption of anesthetic agent all indicate that a clinical case has begun or is ongoing.

As noted above, the streams of time series medical device data originating from the same medical device or from the same location in a hospital may be tagged or otherwise identified as being related. These tags can be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located may further be used to identify clinical cases. For example, coordinated or similar actions in data streams of an anesthesia delivery device and a related patient monitoring device, and/or respiratory support device and/or imaging device, etc., may further be used to identify that these devices are being used together for a clinical case. In still further embodiments, the streaming time series medical device data may be combined with information regarding scheduled clinical cases to help to further identify when and how the medical devices are used during clinical cases.

In embodiments, knowledge of a scheduled use of the medical device (e.g. anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device may help to identify clinical cases from maintenance or calibration actions which may similarly require powering up and at least partial operation of the medical device.

The medical device data associated with the actions by the anesthesia delivery device and/or other medical devices during the identified clinical case may be stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the clinical case database 30, the clinical cases may be classified or profiled which is a technique used for data curation. The profiling of the clinical cases may be based upon, in part, the information in the clinical case summary, and as described in further detail herein, may be used to group the clinical cases into groups, for example normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In a merely exemplary embodiment, for a particular measured value or occurrence, a distribution of such occurrences may be used to establish normal, edge, and outlier cases. In a merely exemplary embodiment, a normal case may be within a standard deviation of a median value in the normal distribution while edge cases are between one and two standard deviations and outlier cases are greater than two standard deviations from the median. The categorized cases, as explained in further detail herein, for example, identified edge cases may be further investigated to create or improve event detection algorithms, rules for clinical decision support, alert algorithms, and predictive algorithms.

The stream processing engine 28 also identifies events in the time series streams of medical device data, for example in the manners as described in further detail herein and presented in business intelligence and visual analytics tools 32 which exemplarily may be presented on a graphical display communicatively connected to the medical device data processing system 12.

Once clinical cases are stored in the operational case database 30, clinical cases may be reviewed manually by a clinician or technician using a curation and case review tool 34. The curation and case review tool 34 may be presented in a graphical user interface on a graphical display and further provide inputs exemplarily through the graphical user interface for the user or technician to curate or otherwise assess the clinical cases. This can be performed for investigative, educational, and data curation purposes.

The reporting and visual analytics tool 32 can present the detected events in a variety of channels of communication. For example, the detected events may be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display, as will be explained in more detail below.

The results of the streaming analytics and event detection in the time series of medical device data may be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to, an anesthetic agent cost dashboard 40, a checkout dashboard 42, a supervisory application 44, an alarm management application 46, an asset management application 48, and a benchmarking application 50.

The agent cost dashboard 40 may present medical device data regarding anesthetic agent use across clinical cases as well as between anesthesia delivery machines within a hospital network or comparatively between hospital networks. By comparatively presenting this information, anesthetic agent use and behavioral changes can be understood and undertaken to promote efficient use of anesthetic agent.

The checkout dashboard 42 may assist in monitoring the inspection and maintenance of the monitored medical devices. Medical device data such as device status and settings, as well as messages and information in machine data, may provide insight into the inspection processes for maintaining medical devices at a hospital network. The checkout dashboard may identify maintenance and/or testing events in the streams of machine data and note these identified testing events against a testing schedule, requirement (e.g., daily), or other criterion.

The supervisory application 44 may be used by attending and/or supervising anesthesiologists to more efficiently manage remote personnel, nurse anesthetists, and/or other care providers simultaneously working across multiple locations or theatres. The alarm management application 46 may report and present medical device data regarding alarm notifications and silences of alarm notifications in order to better understand and adjust alarms to improve signal to noise in alarm events and to reduce alarm fatigue by clinicians. Additional information about the supervisory application 44 is presented below.

The asset management applications 48 may present use, status, maintenance, and/or inspection information regarding medical devices (e.g. anesthesia delivery machines) or consumables used by medical devices, including components that may be frequently replaced, refilled, or refurbished during normal operation of the medical device (e.g. filters, absorbers). The benchmarking application 50 may provide further operational and quality performance across providers and/or organizations or in a comparative manner for example between hospital networks versus averages or between specific locations.

The supervisory application 44 allows for users (e.g., clinicians such as anesthesiologists, nurses, and other care providers) to view ventilator, anesthesia, and vital parameters of a plurality of patients in different locations (e.g., in different operating rooms) on various smart phones, tablets, or other computing devices associated with the users. The supervisory application 44 may include a backend that is hosted on edge device 20 and/or MDD processing system 12 as dockers/micro services and may be rendered on a user's device (such as care provider device 134 shown in FIG. 1B) using a suitable visualization platform.

FIG. 1B schematically shows example devices of system 10 via which supervisory application may be executed, including edge device 20 in communication with a plurality of care provider devices 120 via hospital network 14 and also in communication with MDD processing system 12.

As mentioned above, the edge device 20 receives the medical device data from the medical devices 16. The medical device data received by the edge device 20 may be ingested by a data ingestion module 102, which may be similar to ingestion module 22 of FIG. 1A, and stored in data storage 104. Data storage 104 may be an ephemeral datastore where the received data is stored temporarily rather than persistently. (The received data, such as the medical device data from the medical devices 16, may be sent to the MDD processing system 12 for long-term storage). Further, the received medical device data may be allocated to various micro services on the edge device 20 in order to carry out aspects of supervisory application 44, including a stream processing module 106, a rules engine 108, an inference engine 110, an event notification service 112, a streaming server 114, and a cloud gateway 116.

As explained above, the supervisory application 44 may be used by attending and/or supervising anesthesiologists to manage other care providers, such as nurse anesthesiologists and/or other subordinate care providers. The hospital/medical facility may rely on a relatively high supervision ratio (e.g., 4-10 subordinate care providers for each supervising anesthesiologist), which may increase the need for the supervising anesthesiologists to have high mobility among operating rooms while still overseeing all subordinate care providers and monitoring patient status for all procedures that may be simultaneously ongoing. The supervisory application 44 may facilitate this mobility and management by allowing supervising anesthesiologists to monitor patient status and communicate with subordinate care providers from a remote location. As will be explained in more detail below, the supervisory application 44 may present, via one or more graphical user interfaces displayed on a mobile or other device of a supervising anesthesiologist, patient monitoring parameters (e.g., ECG, heart rate, blood oxygenation) as determined from the received medical device data, procedure phase (e.g., induction, maintenance, and emergence), alarms, anesthesiology machine settings, and other relevant or selected information to a user (e.g., the supervising anesthesiologist). The processing and analysis of the time series streams of medical device data as described above in order to detect events relevant to identified cases (e.g., such as identifying a phase of anesthesia administration) may be utilized and the output of such processing and analysis may be provided to the supervisory application 44. The supervisory application 44 may provide determined values of specified patient monitoring parameters, indications of detected events, and other notifications as determined from the time series streams of medical device data to the user via the graphical user interfaces described herein.

For example, via the supervisory application 44, the user may toggle between graphical user interfaces that show limited information for a plurality of patients (a multi-patient GUI) and more detailed information for a selected patient (a single patient GUI). The user may also view, via the supervisory application 44, trends of patient monitoring data, detailed alarm/notification information, insights, and/or other information. Further, the user may communicate with other care providers, such as a subordinate care provider that is in the room with a patient, via the supervisory application 44. The user may customize which patients/rooms to view, which patient monitoring parameters to view, which alarms and insights to apply, and other parameters of the graphical user interfaces used to present the above-described information, such as a layout of each graphical user interface.

The graphical user interfaces that are generated via the supervisory application 44 may be displayed on one or more suitable display devices associated with a respective care provider device and/or medical facility administration device. As shown in FIG. 1B, a plurality of care provider devices 120 may be included as part of hospital network 14, from a first care provider device 134, a second care provider device 136, and on up to an nth care provider device 138, and may be communicatively coupled to edge device 20 via hospital network 14. Each care provider device may include a processor, memory, communication module, user input device, display (e.g., screen or monitor), and/or other sub-systems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility and substantially fixed in place (such as in a nurses station or in the room of a patient) and/or located locally or remotely from the medical facility and configured to move with the care provider (such as a care provider's mobile device).

When viewing graphical user interfaces generated via the supervisory application 44 via a display of a care provider device, a care provider may enter input (e.g., via the user input device, which may include a keyboard, mouse, microphone, touch screen, stylus, or other device) that may be processed by the care provider device and sent to edge device 20. In examples where the user input is a selection of a link or user interface control button of a graphical user interface, the user input may trigger progression to a desired view or state of the graphical user interface (e.g., trigger display of desired patient medical information), trigger updates to the configuration of the graphical user interface, trigger alarm, insight, and/or other notification settings to be saved, trigger changes to a machine (such as an anesthesia delivery machine), or other actions.

The devices disclosed herein, such as the care provider devices and/or aspects of the edge device 20, may each include a communication module, memory, and processor(s) to store and execute aspects of the supervisory application 44 as well as send and receive communications, graphical user interfaces, medical data, and other information.

Each communication module facilitates transmission of electronic data within and/or among one or more systems. Communication via the communication module can be implemented using one or more protocols. In some examples, communication via the communication module occurs according to one or more standards (e.g., Digital Imaging and Communications in Medicine (DICOM), Health Level Seven (HL7), ANSI X12N, etc.). The communication module can be a wired interface (e.g., a data bus, a Universal Serial Bus (USB) connection, etc.) and/or a wireless interface (e.g., radio frequency, infrared, near field communication (NFC), etc.). For example, a communication module may communicate via wired local area network (LAN), wireless LAN, wide area network (WAN), etc. using any past, present, or future communication protocol (e.g., BLUETOOTH®, USB 2.0, USB 3.0, etc.).

Each memory may include one or more data storage structures, such as optical memory devices, magnetic memory devices, or solid-state memory devices, for storing programs and routines executed by the processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. The processor(s) may be any suitable processor, processing unit, or microprocessor, for example. The processor(s) may be a multiprocessor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, edge device 20 is shown in FIG. 1B as constituting a single entity, but it is to be understood that edge device 20 may be distributed across multiple devices, such as across multiple servers.

The supervisory application 44 may provide various data, notifications, and messages to the plurality of care provider devices 120. The data, notifications, and/or messages may include historical data, real-time medical device data (e.g., provided by streaming server 114), and notifications that may pushed to the plurality of care provider devices 120 from an event notification service 112 via MDD processing system 12 or another a cloud-based service.

Figure 2:
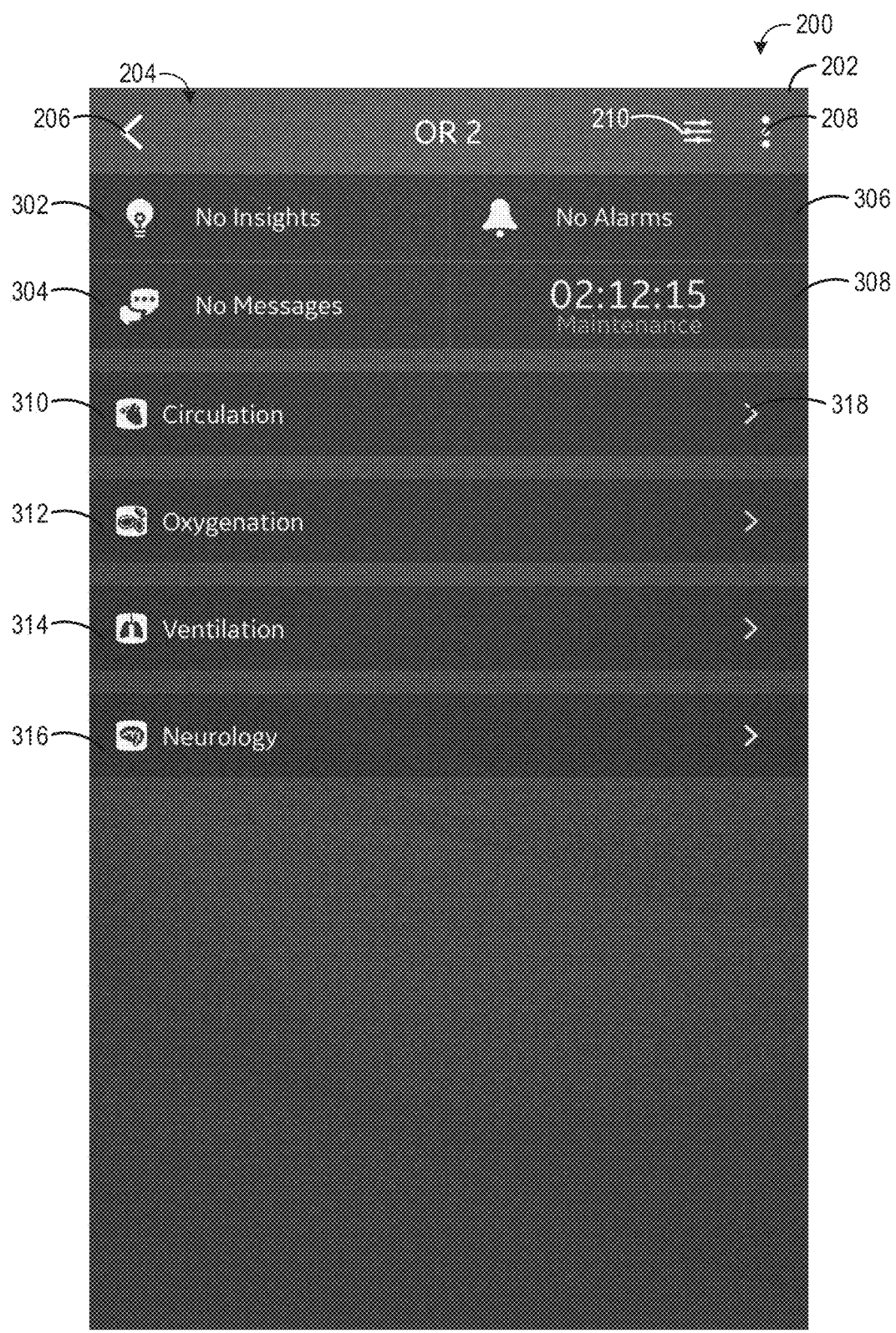
FIGS. 2-5 and 28 show an example display device displaying various views of a single-patient graphical user interface generated via the supervisory application.
Figure 4A:

As will be explained in more detail below, the supervisory application 44 may be visualized on a care provider device in the form of one or more graphical user interfaces. The one or more graphical user interfaces may be populated with real-time patient monitoring parameters, such most-recently determined values or waveforms for heart rate, blood oxygen saturation, respiration rate, and so forth, obtained from the medical devices. When the medical device data is received by the edge device 20, some or all of the medical device data may be processed by stream processing module 106 and supplied to the streaming server 114, which may then supply the real-time patient monitoring parameter values and/or waveforms to a requesting care provider device. For example, when a user is viewing a patient-specific graphical user interface of the supervisory application 44 on care provider device 134, the graphical user interface may include tiles or other display areas where the most-recently determined values for selected patient monitoring parameters are displayed (for example, as shown in FIGS. 2 and 4A and explained in more detail below). The streaming server 114 may stream the most-recently determined values for the selected patient monitoring parameters to the care provider device 134, which may then populate the received values into the graphical user interface. The stream processing module 106 may include rule-based streaming analytics algorithms applying windowing functions (sliding, tumbling, hopping, etc.) used for waveform analysis and event detection, thereby triggering alerts, detection of surgical phases, flow analysis, triaging algorithms, etc. Furthermore, the stream processing module 106 coupled with inference engine 110 may perform predictions such as continuously predictive scoring, patient deterioration scoring, calculate risk indexes, identify early signs of trouble, sepsis prediction, onset of respiratory distress, end-of-case prediction, and clinical decision support in general.

The determination of which patient monitoring parameter values to send to which care provider device may be based at least in part on data requests sent by the care provider devices to the edge device 20. The edge device 20 may include a representational state transfer (REST) server, for example, that may receive data requests from the care provider devices 120 and may respond to the data requests by commanding the streaming server 114 to stream selected medical device data to a requesting care provider device(s). The streaming server 114 may maintain a stateful session (e.g., WebSocket) with each client (e.g., the care provider devices). The medical device data may be adapted (transformed and filtered) before being streamed to the client devices.

Figure 6:
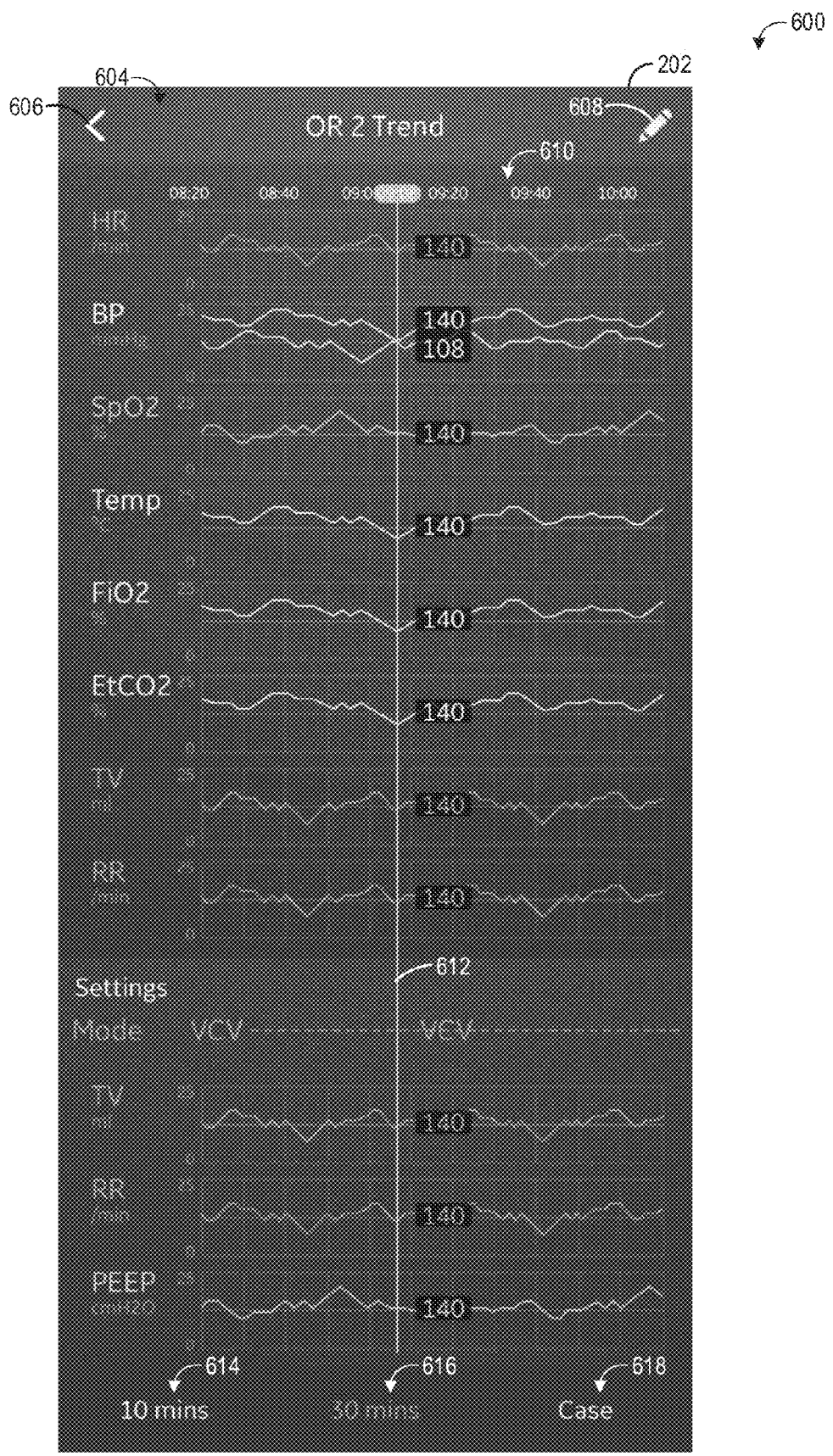
FIGS. 6 and 7 show the display device displaying various views of a trends graphical user interface generated via the supervisory application.

The data requests from the care provider devices 120 may also include requests for historical data (e.g., prior or non-real time patient monitoring parameter values). The historical data may include trends of selected patient monitoring parameters over time. For example, as shown in FIG. 6 and explained in more detail below, a trends graphical user interface may be displayed on a care provider device as part of the supervisory application 44 that shows values for selected patient monitoring parameters over time as trend lines. The trend lines may be assembled from stored medical device data (e.g., stored in data storage 104). When a user requests to view a trends graphical user interface on a care provider device, the care provider device may send a request for the trend lines that are to be displayed in the trends graphical user interface to the edge device 20, and the edge device 20 may obtain the trend lines from the data storage 104 or the edge device 20 may obtain relevant stored medical device data and the trend lines may be assembled at a different location (e.g., by the care provider device).

Figure 22:
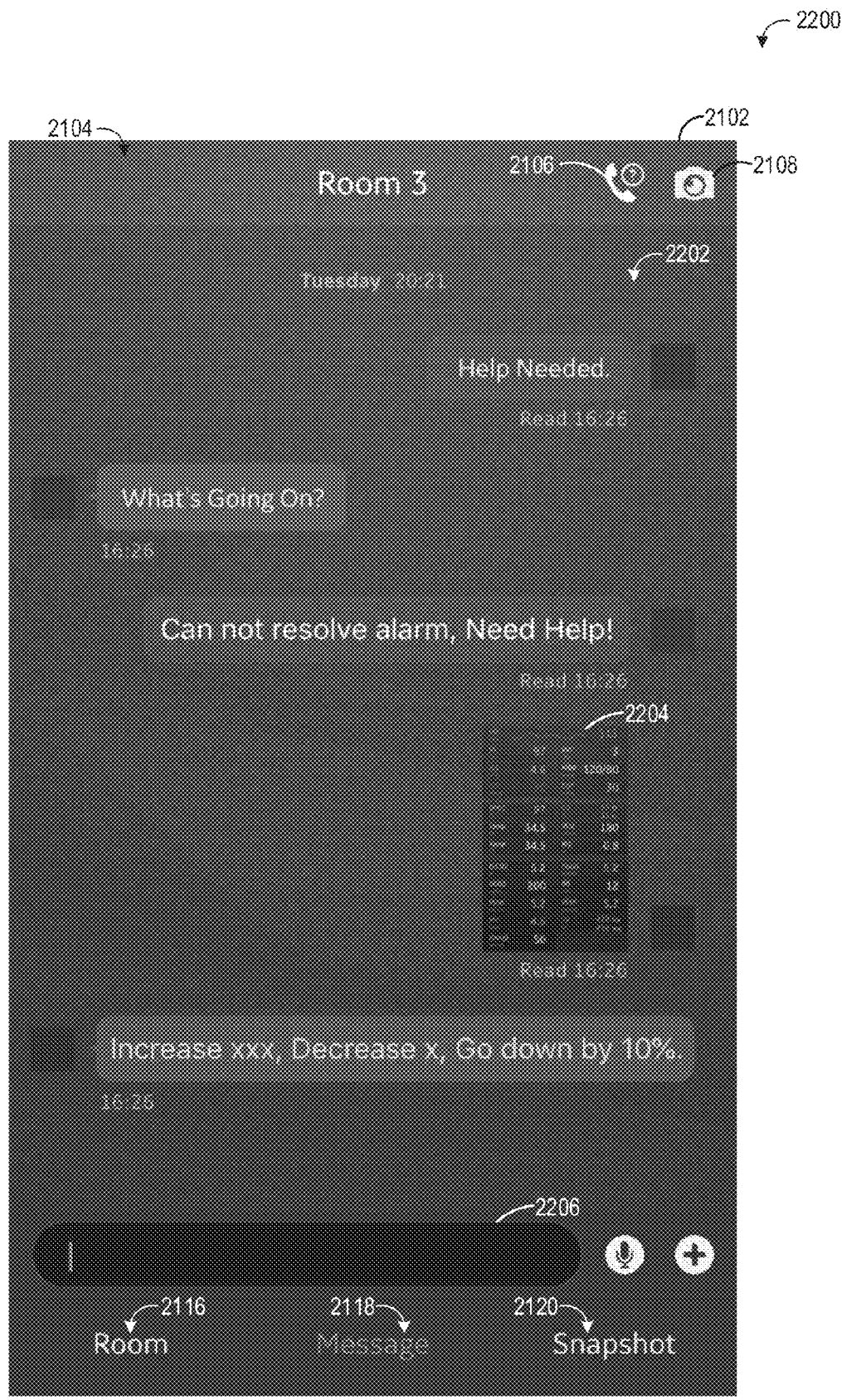

In some examples, users may communicate with one another via the supervisory application 44. For example, as shown in FIG. 22 and described in more detail below, an in-room graphical user interface may be displayed on a care provider device as part of the supervisory application 44. The in-room graphical user interface may include a message view where a care provider in the room with a patient (e.g., a nurse) may communicate with another care provider located outside the room (e.g., an anesthesiologist) via text messages, for example. The messages sent and received via the supervisory application may be routed through the edge device 20 and/or the MDD processing system 12. For example, a first care provider device (e.g., care provider device 134) may send a message intended for a second care provider device (e.g., care provider device 136). The message may be sent from the first care provider device to the edge device 20 and a messaging module of the edge device 20 may receive the message, determine the intended recipient care provider device, and send the message to the intended care provider device (e.g., the second care provider device).

The supervisory application 44 may generate and/or send various alarms and notifications based on the medical device data received from the various medical devices. The alarms may include threshold-based alarms, where a notification/alarm is generated and output to one or more care provider devices in response to a patient monitoring parameter value meeting a predetermined condition relative to a threshold (e.g., an alarm may be generated and sent to a care provider device in response to blood oxygen saturation for a particular patient dropping below a threshold saturation). For example, as shown in FIG. 9 and explained in more detail below, an alarm tile may be displayed as part of a single-patient or multi-patient graphical user interface of the supervisory application 44, where the alarm tile includes an indication of how many alarms have been triggered for a particular patient, where an alarm is generated by a medical device in response to a determination that a patient monitoring parameter for a particular patient has reached a predefined condition relative to a threshold.

The alarms described above may be triggered by a medical device monitoring the patient. For example, the patient may be monitored by a pulse oximeter, which may send SpO2 data to edge device 20 directly or via an anesthesia delivery machine. If the patient's blood oxygen saturation drops below a threshold, the pulse oximeter and/or anesthesia delivery machine may send a notification to edge device 20 indicating that the patient's SpO2 value has dropped below a threshold. Edge device 20, via event notification service 112 and/or cloud gateway 116, may send a notification of the alarm to the care provider device of the care provider attending to the patient. For example, the alarms that are generated may be sent to the appropriate care provider device(s) directly via event notification service 112 or via the cloud gateway 116, which may push the alarms (and other notifications that are generated by edge device 20, as explained in more detail below) via MDD processing system 12 to the appropriate care provider device(s), even when the supervisory application 44 is in an unlaunched state on the care provider device(s).

As mentioned above, the supervisory application 44 is configured to apply insights to the received medical device data in order to provide user-selected notifications, predictions, etc., of patient status. The insights may include the rule-based streaming analytics algorithms performed by the stream processing module 106 and/or inference engine 110 described above (e.g., waveform analysis and event detection, thereby triggering alerts, detection of surgical phases, flow analysis, triaging algorithms, continuously predictive scoring, patient deterioration scoring, calculate risk indexes, identify early signs of trouble, sepsis prediction, onset of respiratory distress, end-of-case prediction, and clinical decision support). The insights may include artificial intelligence based models, such as machine learning or deep learning models. In general, any algorithm, model, or set of rules that may be applied to the medical device data in order to monitor patient state may be considered an insight. In some examples, particularly where the insight requires a high amount of processing power, the insight may be stored/executed on a cloud based device such as the MDD processing system 12.

In some examples, insights may be defined by a user according to a predefined set of parameters and a predefined set of operators and saved as a set of rules. The predefined set of parameters may include all the patient monitoring parameters (including physiological data and machine parameters/settings) that are available to the system (e.g., all the patient monitoring parameters that can be measured, inferred, or otherwise determined from the medical device data). When a parameter is selected (e.g., when a patient monitoring parameter is selected), the user may be presented with a predefined scopes (e.g., timings) to select to limit the insight to specific procedures, timing, etc. Further, when a parameter is selected, the user may be presented with predefined or adjustable thresholds to apply to the parameter. The predefined set of operators may include an "and" operator, an "or" operator, a "while or during" operator, and/or any other suitable operators that allow the user to combine multiple parameters in an insight, or allow the user to select only one parameter for the insight.

Figure 20:
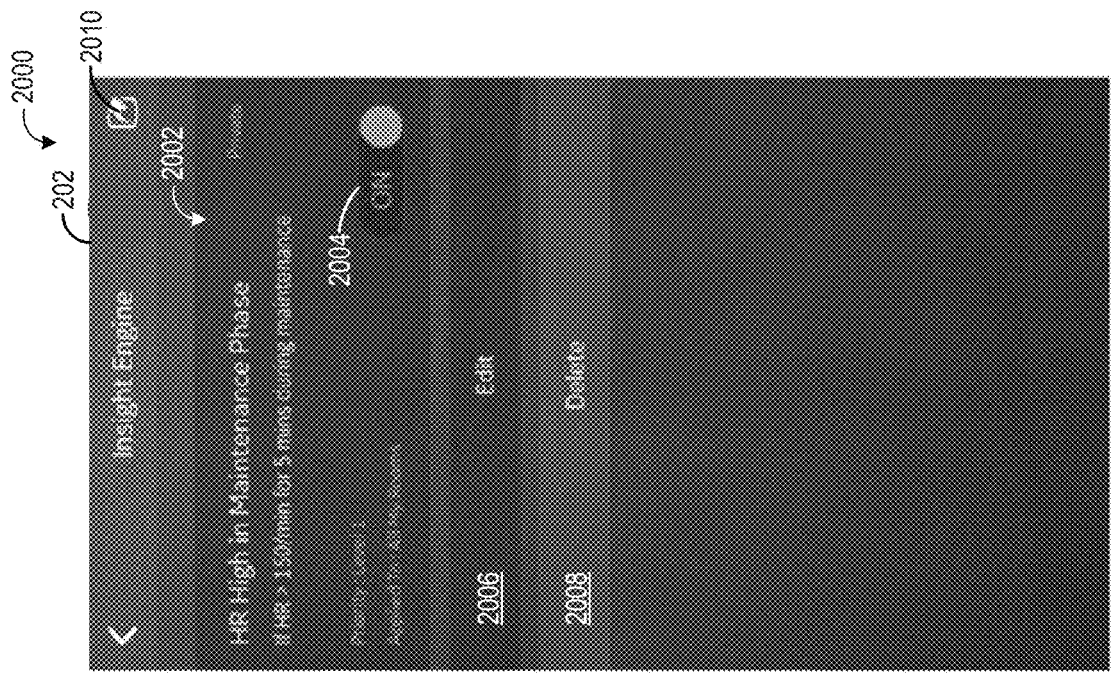

The rules engine 108 may include resources (e.g., memory and processors) of the edge device 20 allocated to store and apply sets of insight rules, which may be similar to alarms, but may be multi-modal and/or multi-parameter. The insights may be user-customized/defined. The insight rules may define a condition and a scope of each insight. For example, as shown in FIG. 20 and explained in more detail below, an insight may include a condition that defines a patient monitoring parameter and corresponding threshold value that may trigger the insight notification, such as patient heart rate being above 150 beats/minute. An insight may further include a scope, which may be a timing- or procedure-based limitation on when the condition of the insight will trigger a notification or result. For example, the scope may define the parameters during which the condition is to be applied, such as how long the condition is to persist before triggering the insight notification (e.g., five minutes), which stage of the procedure the condition is to occur in order to trigger the insight notification (e.g., in maintenance stage of anesthesia delivery), and so forth. As explained above, the user may define the condition and scope from the predefined set of parameters, and if more than one condition is desired in an insight, the user may select an operator from the predefined set of operators. When multiple conditions are included in an insight, after selecting an operator such as "and" or "or," the user may select another parameter from the set of parameters.

The insight rules may be customized by user, and thus the insight rules may define which users (and hence which care provider devices) are to receive which insight notifications. The edge device 20 may distribute medical device data streams to the rules engine 108, and the rules engine 108 may apply the stored insight rules to the incoming streams of medical device data in order to determine if any insight notifications or results should be generated. If an insight notification is to be generated, an insight notification may be generated and sent to the appropriate care provider device(s) via the event notification service 112 and/or cloud gateway 116.

In some examples, an insight may include, as an input, the result of another insight. For example, a first insight may include an algorithm that determines a current anesthesia delivery phase for an anesthesia delivery machine. The output/result of the first insight may be displayed as a tile on a GUI of the supervisory application that is displayed on a care provider device, as will be explained in more detail below. The result of the first insight may also be used as input, along with the medical device data, to a second insight. For example, the second insight may dictate that a notification be output when a selected patient monitoring parameter value reaches a threshold value (or when a change in a selected patient monitoring parameter over a particular time period reaches a threshold) when the result from the first insight indicates that the patient is in maintenance phase of anesthesia delivery. A user may select to include the result of an insight as an input into another insight via the predefined set of parameters described above. For example, when the user creates an insight or applies an insight created by another user, that insight may be included in the predefined set of parameters.

Figure 17:
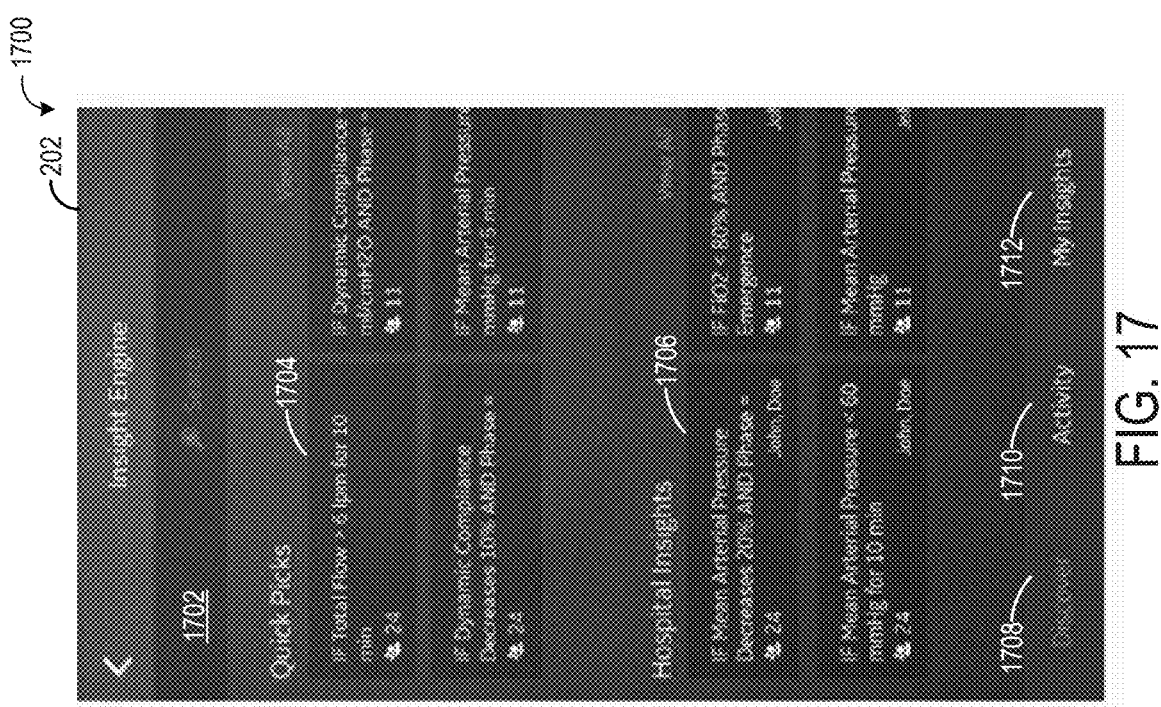

Further, insights may be shared with other users at the medical facility and/or other users at other medical facilities. Thus, when requested, insight rules may be saved at the MDD processing system 12. As shown in FIG. 17 and explained in more detail below, an insight graphical user interface of the supervisory application 44 may be displayed on a care provider device when requested. Via the insights graphical user interface, a user may search for insights defined by users at other medical facilities and/or for insights defined by users at the same medical facility as the user is located, as well as view insights defined by the user. If the user selects to apply an insight, the notification that the insight has been selected may be sent to the rules engine 108 and/or the inference engine 110 and saved as an insight rule to be applied for that user.

The inference engine 110 may be used with artificial intelligence (AI) based models, such as trained deep learning models, to process the incoming data and derive conclusions (insights) from the facts and rules contained in the various machine learning models. The inference engine 110 may be the run-time engine for AI based algorithms, such as prediction of signs of trouble, and these will be part of the inference engine 110. In addition, there may be a deep learning and/or learning network in the cloud, e.g., MDD processing system 12, to train algorithms, where very high compute and resources are necessary.

As explained above, and will be explained in more detail below, via an insights engine feature of the supervisory application 44, users may create their own rules/algorithms from within a user interface and current available data to generate insights, based on their pre-configuration. The insights engine uses streaming, and applies windowing functions, to generate the insights. These insights are then notified to the respective users, based on the users' configuration (e.g., user-subscribed insights), using the event notification service 112. The available data to create a rule may include raw machine data, or the result of an AI algorithm powered by the inference engine 110 (e.g., another insight).

When a user creates their own insight (e.g., rule/algorithm) through the insights engine, they have the opportunity to share that the insight with other users, so other users can adopt and use the same insight. For example, a user may share an insight within the user's institution and other users can see how many people are using the insight and adopt the insight for their own patients/rooms. A user may also see rules (or "insights") that others on the platform outside the user's institution globally have set up, and see the popularity of each insight, and if desired, select one or more of the insights to be applied for their own patients/rooms.

Thus, as explained above, the supervisory application 44 may include a backend hosted on the edge device 20, where the backend includes a plurality of micro services, such as the rules engine 108, inference engine 110, event notification service 112, and streaming server 114. The supervisory application 44, via the backend/edge device 20, may output real-time medical device data to a plurality of care provider devices, trends of medical device data, messages, alarms, insight notifications/results, and/or other information as requested by the front end of the supervisory application 44 that is executed on the care provider devices. The front end of the supervisory application 44 may include a supervisory application visualization platform that may be stored on each care provider device. The supervisory application visualization platform, such as supervisory application visualization platform 135 stored on care provider device 134, may render the data received from the edge device 20 into one or more graphical user interfaces. Additionally, the aspects of the supervisory application 44 that are saved on each care provider device may include various container, component, and presentation layers to receive the data from the edge device 20, populate the graphical user interfaces with the received data, send and receive messages, display notifications, collect GUI settings and other requested customizations (and send the settings/configurations to the edge device 20) and so forth. As an example, the historical data received form the edge device 20 (e.g., the trends) may be sent to a first layer via a REST application programming interface (API), the real-time medical device data may be streamed to the first layer via a web socket, and the push notifications sent from the MDD processing system 12 may be received, processed, and displayed via the visualization platform. Further, when interacting with the graphical user interfaces of the supervisory application, the user may adjust various settings (such as which patient monitoring parameters to display) activate or deactivate alarm notifications, create insights, and so forth. These user-specific preferences/configurations may be saved on the edge device 20 in a preferences/configuration database.

In some embodiments, medical device data and/or other information requested via the supervisory application 44 may be obtained from an electronic medical records (EMR) database 122. For example, historical data (e.g., trend lines) may be obtained from the EMR database 122 in addition to or instead of data storage 104. EMR database 122 may be an external database via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR database 122 is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

The edge device 20 can be implemented in a variety of hardware and/or software implementations and it should be noted that such implementations are not considered to be limiting. For example, it is contemplated that any or all of the edge device 20 may be embodied exclusively in hardware, exclusively in software, exclusively in firmware, or in any combination of hardware, software, and/or firmware. The examples provided herein are not the only way to implement such methods and systems.

In exemplary and non-limiting embodiments of the edge device, the edge device 20 is implemented by one or more processors or computing devices. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to, RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

Figure 13:
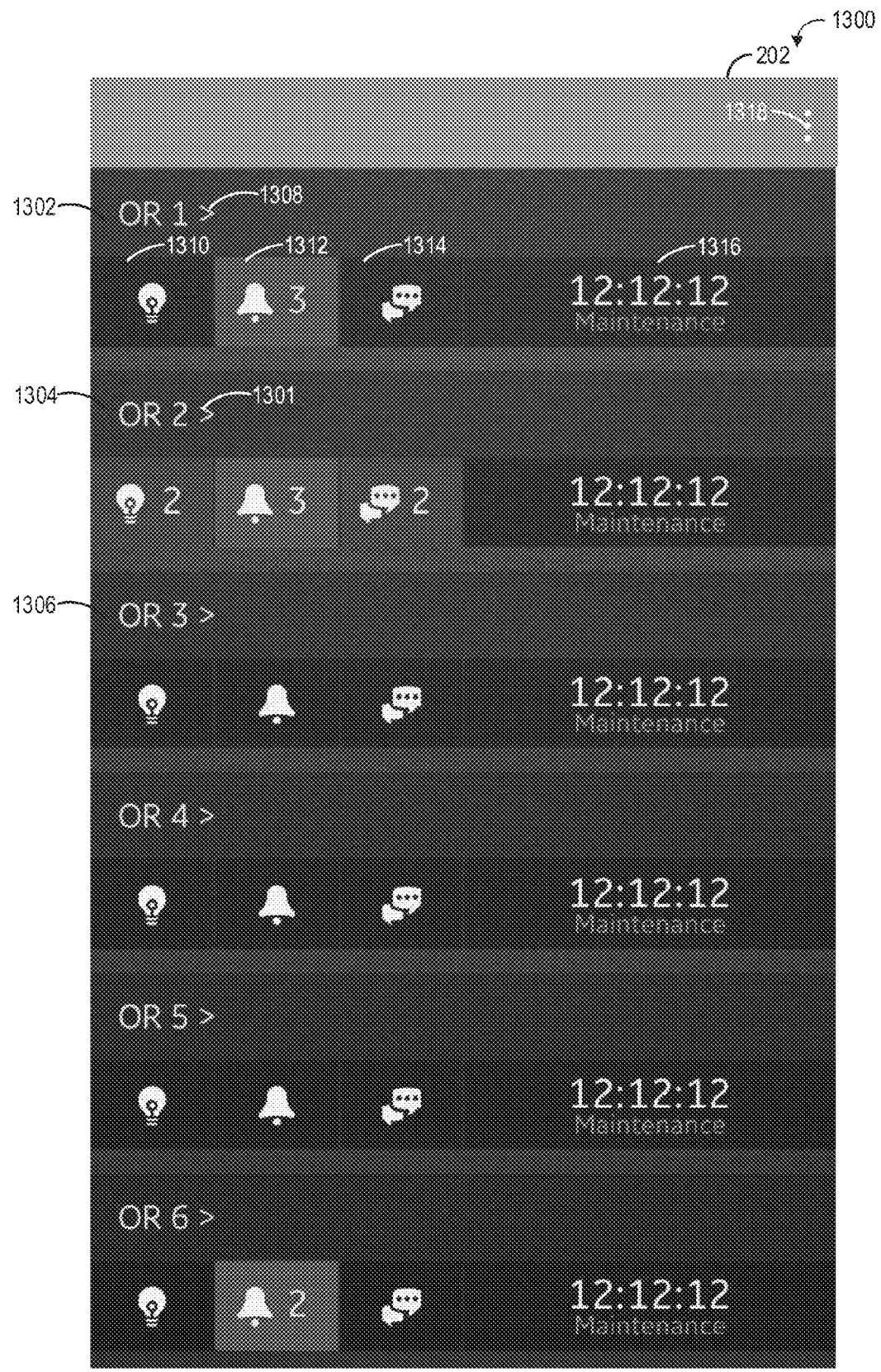

FIG. 2 shows an example single-patient graphical user interface (GUI) 200 that may be displayed when supervisory application 44 is launched on a supervising care provider device. Single-patient GUI 200 may be displayed on a display device 202. Display device 202 may include a screen on which the single-patient GUI is displayed and may be coupled to and/or included as a part of a computing device, such as care provider device 134. Single-patient GUI 200 may be displayed in response to a user request to display the GUI. For example, a user may launch the supervisory application 44 by selecting a supervisory application icon displayed on a home page of the display device. When the supervisory application 44 launches (at least initially), the user may be authenticated via a suitable authentication method, such as via a password, facial recognition, fingerprint recognition, etc. Upon authentication, the user may select to view the single-patient GUI 200 from a suitable menu. For example, the user may access a multi-patient interface that includes a global view of all patients the user has selected to monitor (which may include all patients at the medical facility the care provider is attending to) and may select a desired patient to view. An example multi-patient GUI 1300 is shown in FIG. 13. Multi-patient GUI 1300 may be displayed on display device 202 (or other suitable display device associated with a care provider device) and may include all patients/rooms selected by a user for monitoring. As shown, multi-patient GUI 1300 includes links to patient-specific interfaces. In the examples shown herein, rather than identifying each patient by name or a patient ID number, each patient-specific interface may be identified by the room that patient is currently located in. For example, as shown in FIG. 13, links are displayed for interfaces specific to patients located in a first operating room (OR 1), a second operating room (OR 2), a third operating room (OR 3), and so forth. Additional patient links may be viewed by scrolling the interface. Selection of a patient link may launch the single-patient GUI for that patient. For example, selection of forward button 1301 for OR 2 may cause the single-patient GUI 200 to be displayed.

Returning to FIG. 2, single-patient GUI 200 may include an identification header 204 that identifies the patient whose medical device data/status is being displayed, in the form of the room in which the patient is currently located. In the illustrated example, single-patient GUI 200 is specific to the patient located in the second operating room of the medical facility (OR 2). Identification header 204 may include a back button 206, which when selected via user input (e.g., via touch input to the back button) may cause display of a multi-patient GUI (such as multi-patient GUI 1300 of FIG. 13). Identification header 204 may further include one or more menu buttons, such as menu button 208. When menu button 208 is selected, a context menu may be displayed, which will be explained in more detail below with respect to FIG. 5.

Figure 3:
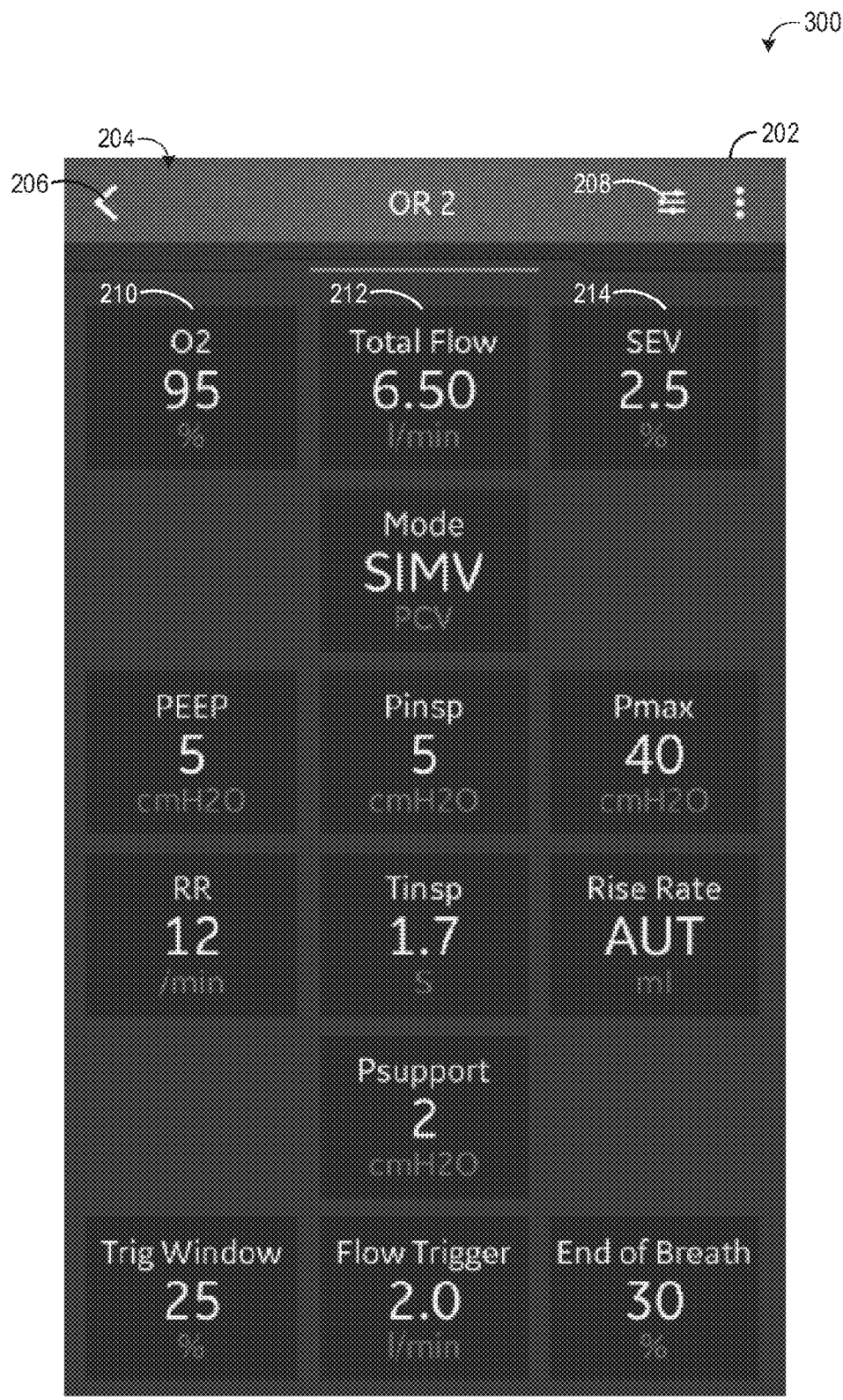

Identification header also includes a parameter view button 210 that, when selected causes display of a parameter view where machine settings/parameters for the one or more medical devices monitoring the patient and/or delivery therapy to the patient (such as machine settings for an anesthesia machine) are displayed. FIG. 3 shows an example parameter view 300 displayed on display device 202 in response to selection of the parameter view button 210. Parameter view 300 displays machine parameters in a first layout that includes an array of tiles. Each selected machine parameter may be displayed as a respective tile, such as a first tile 210, a second tile 212, and a third tile 214. In the example shown in FIG. 3, the first tile 210 displays a first parameter, oxygen percentage, the second tile 212 displays a second parameter, oxygen or medical gas flow rate to the patient, and the third tile 214 displays a third parameter, anesthetic agent type and concentration. Each parameter tile that is displayed via the parameter view 300 may present a most-recently determined value of the respective machine parameter. For example, the first tile 210 is presenting an oxygen concentration of 95%, the second tile 212 is presenting a gas flow rate of 6.50 L/min, and the third tile 214 is presenting a sevoflurane concentration of 2.5%. Each determined value that is presented via a machine parameter tile may be determined from the time series streams of medical device data described above with respect to FIGS. 1A and 1B, and as such may be sent to the care provider device from the edge device 20 via the supervisory application 44. The determined values that are displayed in the parameter view 300, as well as other determined values (such as the patient monitoring parameter values that will be explained in more detail below) may be measured values, estimated values, and/or inferred values. For example, SpO2 may be directly measured from a pulse oximeter, while respiration rate may be inferred from the output of a capnography or from the output form the pulse oximeter.

The patient monitoring parameter tiles included in the single-patient GUI 200 (described below) may present physiological data (e.g., SpO2, respiration rate) of the patient as obtained from one or more patient monitoring medical devices (e.g., a pulse oximeter, a capnograph). The machine parameter tiles included in the single-patient GUI 200 and/or parameter view 300 may present machine data of one or more therapy medical devices that are being utilized during a medical procedure being performed on the patient, such as an anesthesia delivery machine. The machine data may include machine settings or parameters (e.g., ventilator mode, anesthesia type and concentration).

Returning to FIG. 2, single-patient GUI 200 further includes an insights tile 302, a message tile 304, an alarms tile 306, and a procedure timing tile 308. The insights tile 302 may notify the user if any of the user's preset and saved insights have been triggered, which will be explained in more detail below. Briefly, the insights may be similar to threshold-based alarms, but may be multi-modal and/or multi-parameter such that an insight may only be triggered when more than one parameter meets a predetermined condition and/or when a selected parameter meets a predetermined condition during a particular stage of a medical procedure, meets the predetermined condition for a specified amount of time, changes at a specified rate, etc. The messages tile 304 may notify the user if any messages have been received, such as text messages from another care provider. The alarms tile 306 may notify the user if any alarms have been triggered. An alarm may be triggered when a select patient monitoring parameter, such as SpO2, reaches a predetermined condition relative to a threshold, such as SpO2 dropping below 90%. The procedure timing tile 308 may inform the user of the current progress on the medical procedure being performed on the patient. For example, as shown in FIG. 2, an amount of elapsed time since commencement of anesthesia delivery is shown (e.g., 02:12:15), as well as the current phase of the anesthesia delivery (e.g., maintenance phase). The phase of anesthesia delivery may be determined by a phase determining insight that may be executed by the MDD processing system 12 and/or edge device 20, as explained above with respect to FIGS. 1A and 1B.

Additional patient monitoring parameters that are displayable via single-patient GUI 200 may be organized into categories, and each patient monitoring category may be collapsed or expanded. When collapsed, no patient monitoring parameters for that category are displayed. When expanded, the patient monitoring parameters for that category are displayed. FIG. 2 shows each category in a collapsed configuration. The patient monitoring categories shown in FIG. 2 include a circulation category 310, an oxygenation category 312, a ventilation category 314, and a neurology category 316, although other categories are possible without departing from the scope of this disclosure. The displayed patient monitoring categories may be customized by the user, such that the user may select which categories will be displayed on that user's device. Each patient monitoring category includes a forward arrow, such as forward arrow 318, which when selected by the user causes the category to expand so that the patient monitoring parameters in that category may be viewed.

FIG. 4A shows a first view 400 of a progression through different views of single-patient GUI 200. In the first view 400, the user has selected two categories to expand (the circulation category 310 and the oxygenation category 312) and two categories remain collapsed (the ventilation category 314 and the neurology category 316). When a category is expanded, the associated forward arrow may switch to a down arrow, as shown by down arrow 402, to signify that the category has been expanded. User selection of the down arrow causes the category to collapse.

As appreciated by FIG. 4A, when a category is expanded, a plurality of patient monitoring parameters may be displayed. For example, the circulation category 310 includes eight patient monitoring parameters (e.g., an ECG waveform, a most-recently determined heart rate, and so forth) each related to circulation. The oxygenation category 312 includes six patient monitoring parameters (e.g., a most-recently determined SpO2), each related to oxygenation. The patient monitoring parameters that are included in each category may be selected by the user via an edit function, which may be executed via the context menu of FIG. 5 or by a user input made to a category. For example, a swipe motion on the circulation category 310 banner may trigger display of an edit button. Selection of the edit button may trigger control buttons to be displayed, via which patient monitoring parameters in the category may be deleted and/or additional patient monitoring parameters may be added. In this way, the edit/customization functionality gives the power to the user to view any parameter in the system using the single-patient GUI, including a trend of that parameter, within a tile. For example, via the edit function, the user may choose to view a patient monitoring parameter as a single value (e.g., most recently determined value), as a trend showing change in the patient monitoring parameter over time, or both. The user has the power to create their own views, their own insights, and so forth, as will be explained in more detail below.

As explained above, one or more of the patient monitoring parameters that are displayed in the expanded view of a category may include a most-recently determined value for that parameter. For example, in the oxygenation category 312, an SpO2 tile 404 may be displayed, showing the most-recently obtained SpO2 value. However, it may be beneficial for the user to view a change in the values of a patient monitoring parameter over time. To access a view where one or more patient monitoring parameter trends are displayed, the user may enter an input to a selected patient monitoring parameter tile, such as a single touch input (schematically shown by hand 406) to SpO2 tile 404. Selection of the patient monitoring parameter tile may trigger a trend view for the selected patient monitoring parameter, as shown in FIG. 4B.

Figure 4B:
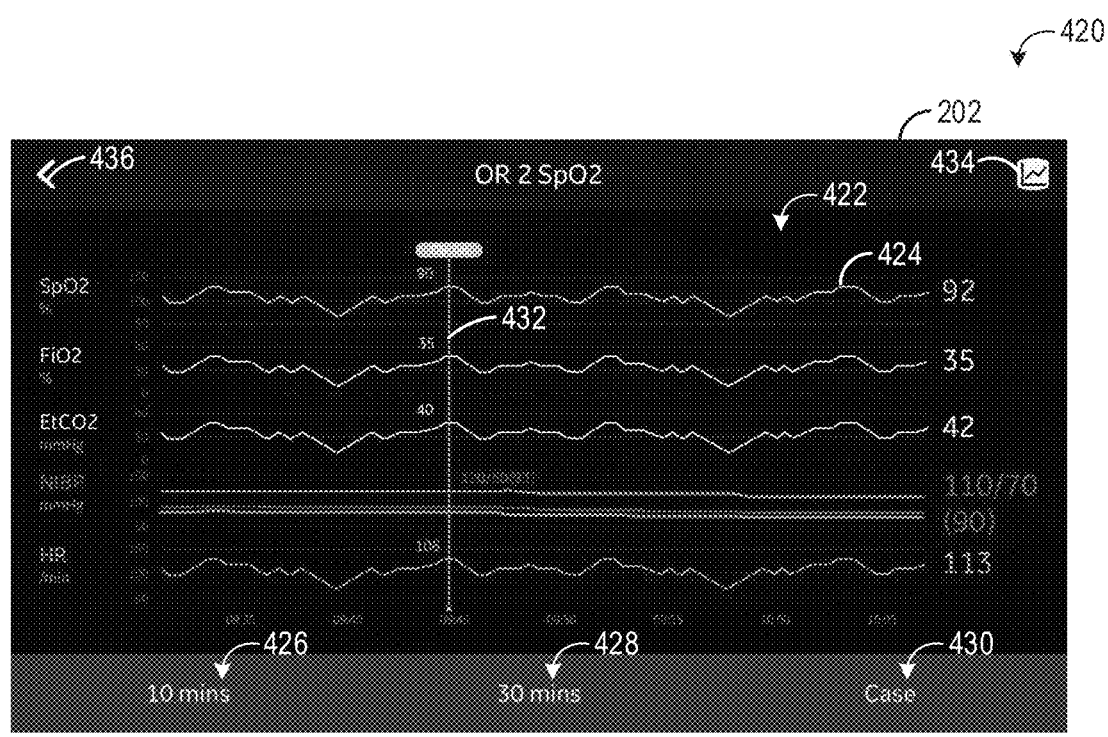

FIG. 4B shows a second view 420 of single-patient GUI 200 displayed on display device 202. Second view 420 includes a set of trends 422 that may be displayed in response to user selection of the SpO2 tile 404. The set of trends 422 may be displayed as an overlay on top of the first view 400, or the set of trends 422 may be displayed as a separate window, taking the place of or fully obscuring the first view 400. The set of trends 422 includes an SpO2 trend line 424 and a plurality of related trend lines, herein the fraction of inspired air comprised of oxygen (FiO2), end-tidal CO2 (EtCO2), blood pressure (NIBP, including diastolic and systolic measurements), and heart rate (HR). Each trend line is plotted on its own y-axis, such that the values of each patient monitoring parameter may be plotted on different scales and with different units where applicable. Each trend line is plotted on a common x-axis, so that the trend lines are time-aligned. The trend lines may be stacked vertically. In this way, relationships or correspondence of changes among the displayed patient monitoring parameters may be easily identified by a viewer.

The patient monitoring parameter trends that are displayed along with the SpO2 trend line 424 in response to the selection of the SpO2 tile 404 may include trends of patient monitoring parameters not necessarily included in the oxygenation category 312. For example, EtCO2 may be displayed as part of the ventilation category 314, while NIBP and HR are each displayed as part of the circulation category 310. FiO2 may not be displayed in any of the categories shown in FIG. 4A. In this way, the patient monitoring parameters may be grouped together in categories based on the relatedness of what each patient monitoring parameter is detecting, which may aid the user in being able to quickly navigate to view a desired patient monitoring parameter(s) when viewing the first view 400 or another view that shows the most-recently determined values for each patient monitoring parameter. Then, when the user wants to view a trend for a selected patient monitoring parameter, other patient monitoring parameters that have been predetermined to be related to the selected patient monitoring parameter, or otherwise have been predetermined to be informative about past or current patient status, may be presented along with the selected patient monitoring trend, without the user having to enter additional inputs.

The patient monitoring parameter trends that are displayed along with the selected patient monitoring trend may be predetermined by the user, e.g., via a settings menu. In other examples, the patient monitoring parameter trends that are displayed along with the selected patient monitoring trend may be automatically determined by the supervisory application 44. For example, the supervisory application may include default sets of related patient monitoring parameters, and when one patient monitoring parameter in a set is selected, all other patient monitoring parameters in that set may also be displayed. In some examples, the supervisory application 44 may learn or otherwise adjust over time which patient monitoring parameter trends should be displayed together.

The second view 420 further includes time range control buttons displayed along a bottom of the set of trends 422. For example, a first time range control button 426 may be selected to show the set of trends over a first time range (e.g., 10 minutes), a second time range control button 428 may be selected to show the set of trends over a second time range (e.g., 30 minutes), and a third time range control button 430 may be selected to show the set of trends over a third time range (e.g., the entirety of the case/procedure). However, other time ranges are possible without departing from the scope of this disclosure.

In some examples, user input to the set of trends 422 may cause display of a timeline 432. The timeline 432 may include a vertical line bisecting each trend line at a given point in time. The timeline 432 may be moved (e.g., drug) along the x-axis to a desired time point. Further, instantaneous values of each patient monitoring parameter at the time point corresponding to the position of the timeline may be displayed alongside the timeline 432. For example, in FIG. 4B, the timeline 432 is positioned at 09:46, and thus values for SpO2, FiO2, EtCO2, NIBP, and HR determined at or near 09:46 (or, depending on the frequency at which each patient monitoring parameter is determined, an inference of the value at that time) are displayed next to the timeline 432.

The second view 420 further includes, at least in some examples, a trends icon 434. User selection of the trends icon 434 may cause a trends GUI to be displayed, which will be explained in more detail below with respect to FIGS. 6 and 7. Additionally, the second view 420 includes a back button 436. When selected, the back button 436 may trigger display of the first view 410 and/or other view of the single-patient GUI that was previously displayed.

Figure 4C:
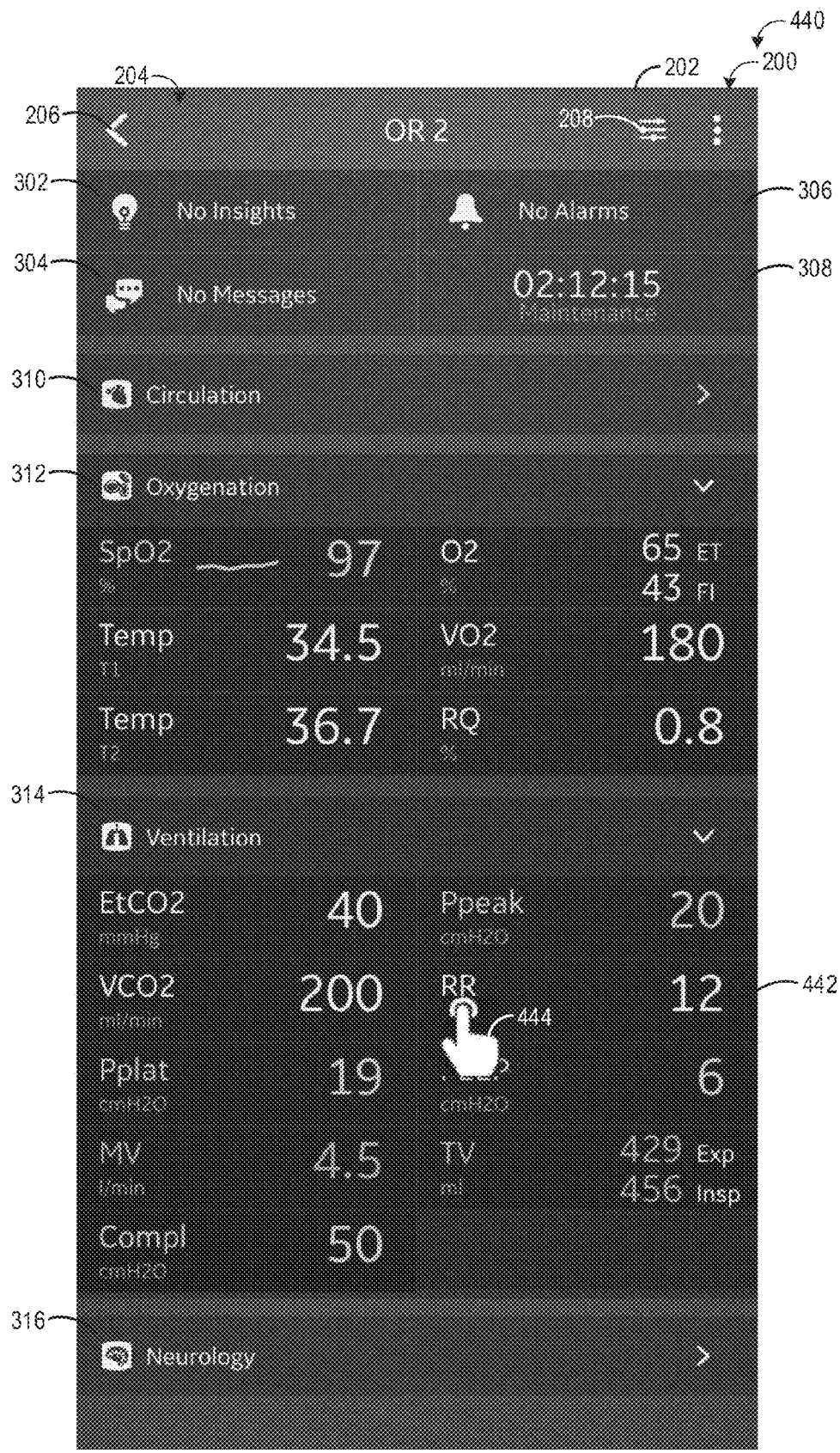

FIG. 4C shows a third view 440 of the single-patient GUI 200. In the third view 440, the circulation category 310 has been collapsed, the oxygenation category 312 remains expanded, the ventilation category 314 is expanded, and the neurology category 316 remains collapsed. In the example shown in FIG. 4C, the ventilation category 314 includes nine patient monitoring parameters (e.g., EtCO2, respiration rate (RR), plateau pressure (Pplat), and so forth) each related to ventilation.

As explained above, the user may select a patient monitoring parameter tile in order to view a trend for that patient monitoring parameter over time. In the example shown in FIG. 4C, the user is selecting a respiration rate (RR) tile 442 via a touch input (shown schematically by hand 444). Selection of the respiration rate tile 442 causes a set of trends to be displayed as an overlay across a portion of the third view 440, as shown in FIG. 4D.

Figure 4D:
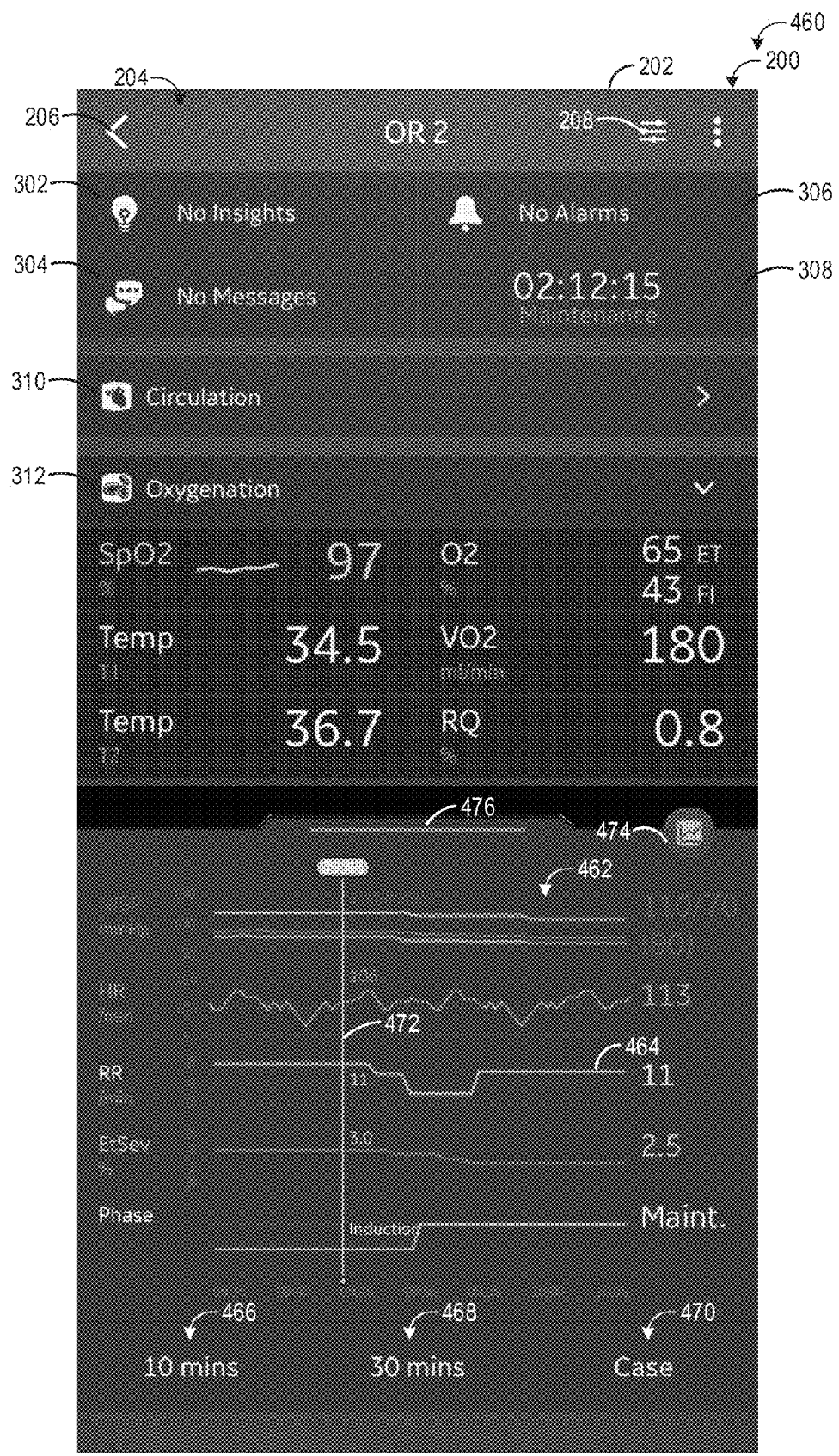

FIG. 4D shows a fourth view 460 of single-patient GUI 200. In the fourth view 460, a set of trends 462 is displayed at a bottom portion of the single-patient GUI 200. The set of trends 462 includes a trend line 464 for respiration rate, as the set of trends 462 was displayed in response to user selection of the respiration rate tile 442, as explained above with respect to FIG. 4C. The set of trends 462 includes a plurality of related trend lines, herein blood pressure (NIBP, including diastolic and systolic measurements), heart rate (HR), end-tidal concentration of sevoflurane (EtSev), and anesthesia phase (e.g., induction, maintenance, or emergence). Each trend line is plotted on its own y-axis, such that the values of each patient monitoring parameter may be plotted on different scales and with different units where applicable. Each trend line is plotted on a common x-axis, so that the trend lines are time-aligned. The trend lines may be stacked vertically. In this way, relationships or correspondence of changes among the displayed patient monitoring parameters may be easily identified by the user.

As explained previously, the patient monitoring parameter trends that are displayed along with the respiration rate trend line 464 may include trends of patient monitoring parameters not necessarily included in the same category as respiration rate. Further, the patient monitoring parameter trends that are displayed along with the respiration rate trend may be predetermined by the user or determined automatically by the supervisory application.

The fourth view 460 further includes time range control buttons displayed along a bottom of the set of trends 462. For example, a first time range control button 466 may be selected to show the set of trends over a first time range (e.g., 10 minutes), a second time range control button 468 may be selected to show the set of trends over a second time range (e.g., 30 minutes), and a third time range control button 470 may be selected to show the set of trends over a third time range (e.g., the entirety of the case/procedure). However, other time ranges are possible without departing from the scope of this disclosure. When prompted, a timeline 472 may be displayed, similar to the timeline 432 described above.

The fourth view 460 further includes, at least in some examples, a trends icon 474. Additionally, the fourth view 460 includes a swipe tab 476. When the user makes a down-swipe motion to the swipe tab 476, the set of trends 462 may collapse to reveal the categories/patient monitoring parameters displayed in the third view 440. When the set of trends is collapsed, the swipe tab 476 may be visible, and an up-swipe motion to the swipe tab 476 may cause the set of trends 462 to be displayed again.

In some examples, when the user selects a patient monitoring parameter tile, the resultant set of trends may be displayed in the manner shown in FIG. 4D when the display device 202 is at a first orientation (e.g., portrait, with the longitudinal axis of the display device oriented vertically with respect to the ground) and the set of trends may be displayed in the manner shown in FIG. 4B when the display device 202 is at a second orientation (e.g., landscape, with the longitudinal axis of the display device orientated horizontally with respect to the ground).

While FIGS. 4C and 4D illustrated a patient monitoring parameter trend and a set of additional trends of related patient monitoring parameters, in some examples, when a patient monitoring parameter tile is selected, a more detailed trend view for only that patient monitoring parameter may be shown. For example, referring back to FIG. 4A, one of the patient monitoring parameter tiles included in the circulation category is an ECG tile, where the patient's ECG signal is represented by a single waveform. However, ECG monitors may include multiple electrodes/leads, such as 12, each generating a respective ECG signal. Selection of the ECG tile may cause a trends view to be displayed where only ECG signals are shown, such as the signals from some or all of the ECG leads.

Figure 5:
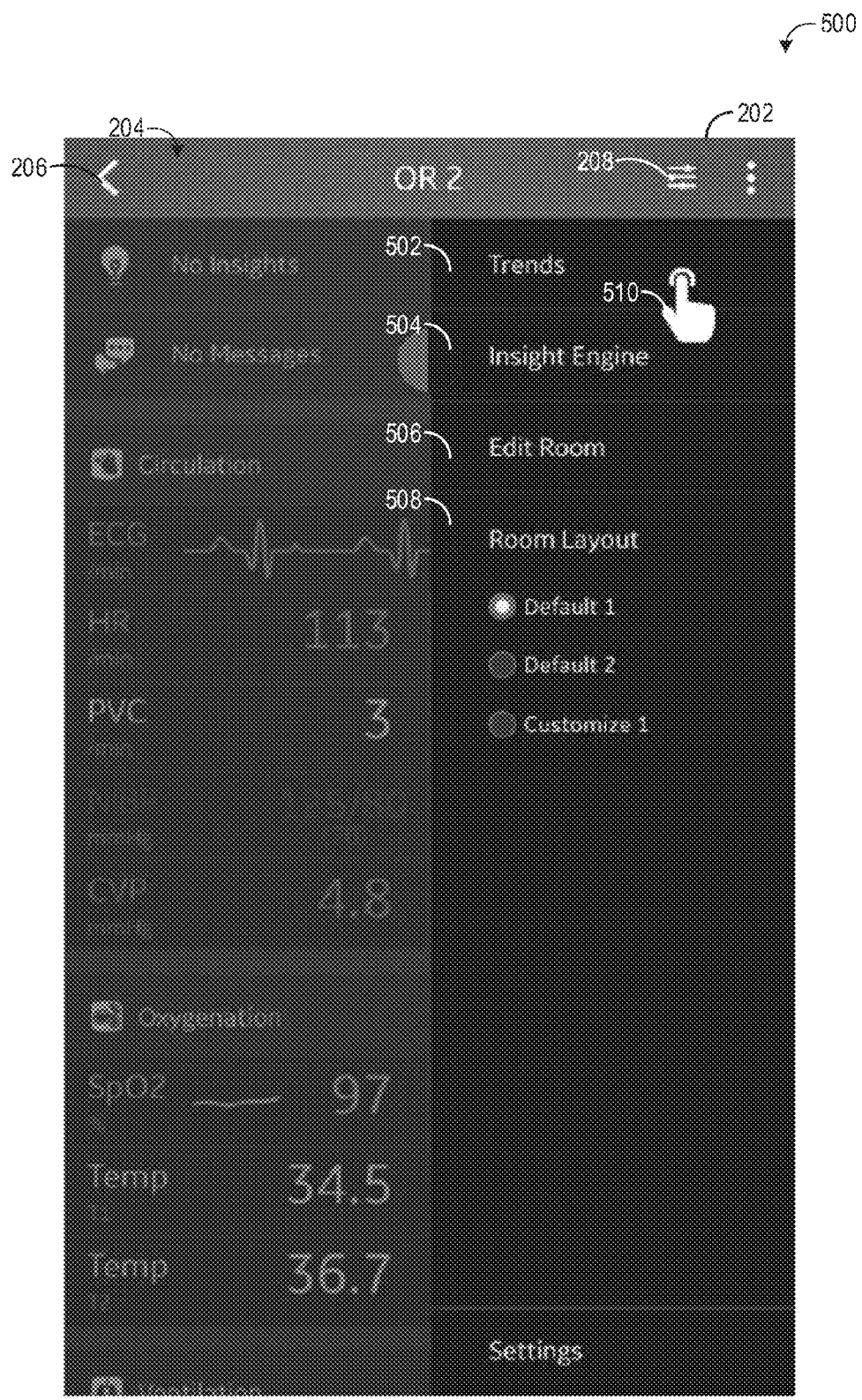

FIG. 5 shows a context menu 500 that may be displayed as part of a single-patient GUI, such as single-patient GUI 200. The context menu 500 may be displayed in response to user selection of the menu button 208. The context menu 500 may be displayed as an overlay on top of an existing view of the single-patient GUI (as shown in FIG. 5) or as a separate menu.

The context menu 500 may include a plurality of control buttons that may trigger different actions. For example, the context menu 500 may include a trends button 502, an insights engine button 504 (which may trigger display of an insights GUI, as will be described in more detail below with respect to FIGS. 17-20), an edit room button 506, and a room layout set of buttons 508. The room layout set of buttons 508 may include a button for each different possible layout for how the single-patient GUI is configured for display. For example, a first layout (e.g., corresponding to single-patient GUI 200) may be displayed when the "Default 1" button is selected, a second default/preconfigured layout may be displayed when the "Default 2" button is selected, and a third layout (which may be a layout customized by the user) may be displayed when the "Customize 1" button is selected. When a user makes adjustments to the layout of a single-patient GUI, including changing which patient monitoring parameter tiles are included in the single-patient GUI, the user may save the layout of the single-patient GUI, which may then be selectable as a customized layout from the context menu.

When the edit room button 506 is selected, the single-patient GUI (in the chosen layout) may be displayed with selectable control buttons displayed for each currently-selected patient monitoring parameter. User input to a control button may toggle that patient monitoring parameter between being selected (and thus included in the GUI) and not selected (and thus not included in the GUI). Additional patient monitoring parameter(s) may be added via an add control button. Further details of how patient monitoring parameters may be added to a GUI are presented below with respect to FIGS. 15 and 16. In some examples, when a patient monitoring parameter is added to the GUI or removed from the GUI, one or more of the remaining patient monitoring parameter tiles may be adjusted (e.g., moved from a first location to a second location, resized, rescaled, adjusted to show more or less information) in order to accommodate the new patient monitoring parameter tile, present a visually pleasing and easy to view arrangement of tiles, show as much information as possible on the display, etc. The adjustment of the one or more remaining tiles may be performed automatically, or the user may make desired adjustments in the manner described herein.

In the example shown in FIG. 5, a touch input is being entered to the trends button 502 (shown schematically by hand 510). Selection of the trends button 502 causes a trends GUI to be displayed. FIG. 6 shows an example trends GUI 600 that may be displayed in response to selection of a trends button from a context menu (e.g., selection of trends button 502) and/or in response to selection of a trends icon (e.g., trends icon 474). Trends GUI 600 is specific to a selected patient, herein the patient located in OR 2. Trends GUI 600 includes an identification header 604 that identifies the patient for which the trends are being displayed, including a back button 606 and an edit button 608. When selected, the edit button 608 may allow a user to select which trends to view via the trends GUI 600. The trends GUI 600 may be similar to the sets of trends that may be displayed in response to user selection of a patient monitoring parameter, as explained above with respect to FIGS. 4B and 4D. As such, the trends GUI 600 may include a set of trends 610 for each of a plurality of patient monitoring parameters, time-aligned and stacked vertically. When prompted, trends GUI 600 may display a timeline 612, similar to the timeline 432 described above, that bisects each trend line and that may be moved along the x-axis to a desired time. As explained above, the timeline 612 may include an instantaneous value for each patient monitoring parameter at the time coinciding with the position of the timeline 612.

The trends GUI 600 further includes time range control buttons displayed along a bottom of the set of trends 610. For example, a first time range control button 614 may be selected to show the set of trends over a first time range (e.g., 10 minutes), a second time range control button 616 may be selected to show the set of trends over a second time range (e.g., 30 minutes), and a third time range control button 618 may be selected to show the set of trends over a third time range (e.g., the entirety of the case/procedure). However, other time ranges are possible without departing from the scope of this disclosure.

As shown in FIG. 6, the displayed physiological parameter trends include heart rate, blood pressure, SpO2, temperature, FiO2, EtCO2, tidal volume (TV), respiration rate (RR), and positive end expiratory pressure (PEEP). The displayed machine setting trends include machine mode (herein, the machine is controlled in a volume control ventilation (VCV) mode). The displayed trends may be customized by the user, for example by selecting the edit button 608 and deleting displayed trends or adding trends to be displayed (e.g., from a list of possible patient monitoring parameter trends). While each of the trends shown in FIG. 6 are formatted as trend lines, in some embodiments one or more of the patient monitoring parameter trends may be displayed in a different format, such as a series of bar graphs.

As explained above, the trends GUI 600 may include a timeline when prompted. In some embodiments, the timeline may be displayed in response to a first user input, such as a single touch input entered to the display along the time points displayed above the set of trends 610. While the timeline may show respective values for each of the patient monitoring parameters at a single point in time, it may be beneficial for the user to view changes in the patient monitoring parameters in a more quantifiable manner (e.g., rather than having to guess at an overall trend based on the trend lines). Accordingly, a set of timelines may be displayed in response to a second user input, such as two concurrent touch inputs made to the display at the set of trends 610 (e.g., two fingers touching the display at the same time). A respective timeline may then be displayed at times corresponding to the location of the touch inputs, as shown in FIG. 7.

Figure 7:
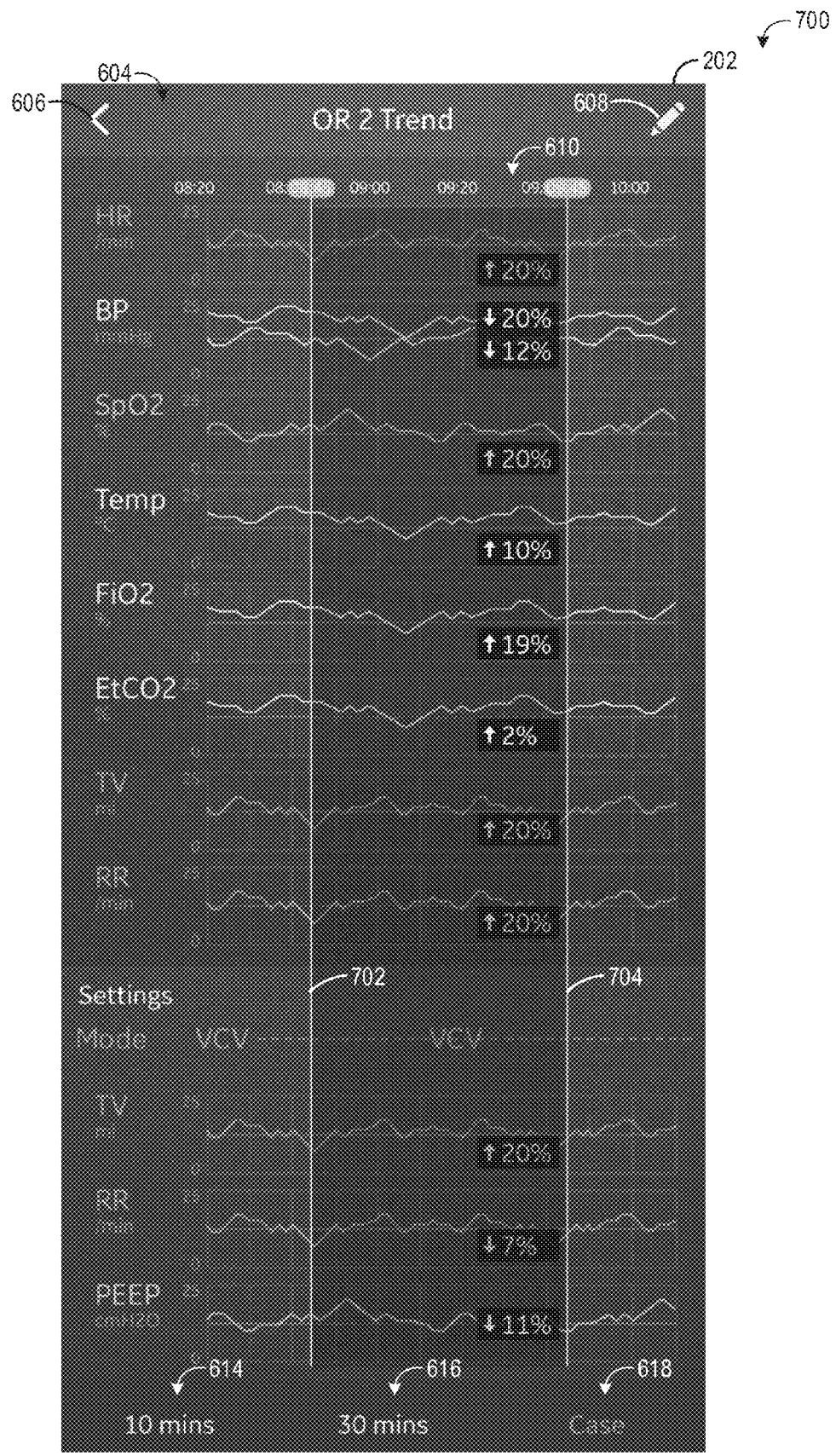

FIG. 7 shows a view 700 of the trends GUI 600 of FIG. 6 with two timelines displayed on the set of trends 610. The timelines include a first timeline 702 and a second timeline 704. First timeline 702 may be positioned at a location corresponding to a first touch input (e.g., at 08:45) and second timeline 704 may be positioned at a location corresponding to a second touch input (e.g., at 09:45) of two concurrent touch inputs. The two timelines may be moved in response to a third touch input, such as the two timelines being brought closer together or moved further apart in response to concurrent touch inputs to the two timelines followed by dragging of the timelines closer together or further apart.

When the two timelines are displayed as shown in FIG. 7, rather than displaying corresponding instantaneous values for each displayed patient monitoring parameter (as shown in FIG. 6), an overall change in each patient monitoring parameter over the duration between the first timeline 702 and the second timeline 704 is displayed. For example, an overall change in heart rate may be determined from 08:45 to 09:45 (e.g., an increase of 20%) and displayed next to the trend line for heart rate.

As explained above with respect to FIG. 2, single-patient GUI 200 includes an insights tile 302, a message tile 304, and an alarms tile 306, where notifications regarding insights, messages, and alarms, respectively, specific to the patient are displayed. When an insight or alarm has been triggered, or when a message has been received, the user may select the appropriate tile to cause the insight, message, or alarm to be displayed. FIGS. 8-10 show example views of single-patient GUI 200 where the insights tile is selected, the alarm tile is selected, and the messages tile is selected, respectively.

Referring first to FIG. 8, it shows an insights view 800 of single-patient GUI 200 displayed on display device 202 where the insights tile 302 indicates that two insights have been triggered for the patient (e.g., located in OR 2). User selection of the insights tile 302 (shown schematically by hand 802) causes an insights banner 804 to be displayed. The insights banner 804 may indicate the insight(s) that have been triggered for the patient, such as an oxygen/medical gas flow via the ventilator to the patient that has been greater than 6 pounds a minute for more than 10 minutes (as shown in FIG. 8). In the example shown in FIG. 8, the insights banner 804 is showing information related to a first insight. If additional insights have been triggered for the patient, user input (e.g., a touch input swiping the insights banner) may cause the additional insight(s) to be displayed at the insights banner 804. Further, a visual notification of the addition insights may be displayed, such as the two dots shown above the insights banner 804 in FIG. 8.

Additionally, user selection of the insights tile 302 causes action buttons to be displayed, including an acknowledge button 806 and a snooze button 808. When selected, the acknowledge button 806 may indicate to the supervisory application that the user has seen the insight, and thus further notification of the insight via the current single-patient GUI 200 may be dispensed with. When selected, the snooze button 808 may indicate to the supervisory application that the user has seen the insight, but would like to be reminded of the insight again after a threshold time period has elapsed (e.g., 10 minutes).

In some embodiments, patient monitoring information relevant to the insight may be displayed along with the insights banner 804. In the example shown in FIG. 8, a set of trends 810 is displayed below the insights banner 804. The set of trends 810 includes a trend line 812 for the oxygen/medical gas flow referenced in the insight as well as trend lines for parameters related to the oxygen/medical gas flow, shown here as including the anesthesia phase, anesthesia concentration (e.g., Sev %), and patient oxygen saturation (e.g., O2%). Similar to the other sets of trends explained above, a timeline 814 may be displayed in response to user input (e.g., a touch input to a selected time point of the set of trends 810).

Referring to FIG. 9, it shows an alarm view 900 of single-patient GUI 200 displayed on display device 202 where the alarm tile 306 indicates that an alarm has been triggered for the patient (e.g., located in OR 2). User selection of the alarm tile 306 (shown schematically by hand 902) causes an alarm banner 904 to be displayed. The alarm banner 904 may indicate the alarm(s) that have been triggered for the patient, such as SpO2 being below a threshold value (as shown in FIG. 9). In the example shown in FIG. 9, the alarm banner 904 is showing information related to a first alarm. If additional alarms have been triggered for the patient, user input (e.g., a touch input swiping the insights banner 804) may cause the additional alarm(s) to be displayed at the alarm banner 904.

Additionally, user selection of the alarm tile 306 causes action buttons to be displayed, including an acknowledge button and a snooze button, similar to the acknowledge and snooze buttons presented above with respect to FIG. 8. Also shown in FIG. 9 is a settings button 906 that may be displayed when the alarm tile 306 is selected. When selected, the settings button 906 may cause display of settings/system alarms menu where the user may customize the alarms, e.g., delete existing alarms, add new alarms, and/or edit existing alarms.

Referring to FIG. 10, it shows a message view 1000 of single-patient GUI 200 displayed on display device 202 where the message tile 304 indicates that a consultation for the patient (e.g., located in OR 2) has been requested by another care provider (e.g., a subordinate care provider or other care provider located in the room with the patient). User selection of the message tile 304 (shown schematically by hand 1002) causes a message banner 1004 to be displayed. The message banner 1004 may indicate the nature of the message that has been received, such as the consultation being requested. In the example shown in FIG. 10, the message banner 1004 is showing that a consultation has been requested. However, other types of messages may be received, such as SMS-based text messages from another care provider requesting a particular type of assistance, asking questions, sharing details of current patient status, and so forth. In such examples, the message banner 1004 may indicate that a text message has been received from a care provider currently caring for that patient. Further, if additional messages have been received that are related to the patient, user input (e.g., a touch input swiping the message banner) may cause the additional messages to be displayed at the message banner 1004.

Additionally, user selection of the message tile 304 and/or of message banner 1004 may cause a message thread 1006 to be displayed, where messages sent and received with the care provider who sent the triggering message may be displayed. Also shown in FIG. 9 is a message input box 1008 where the user may enter text or voice input in order to send a message to the requesting care provider. For example, as shown, the user may respond with an estimated amount of time for the user to be available for the requested consultation.

Thus, FIGS. 2-10 show various views of a single-patient GUI that may be displayed on a care provider device as part of the supervisory application. Via the single-patient GUI, a user (such as a supervising anesthesiologist or other supervising care provider) may view real-time patient monitoring parameters for a specific patient, which may include physiological parameters of the patient and/or machine settings for one or more therapy devices being used to perform a procedure on the patient. Further, via the single-patient GUI, the user may view trends for one or more patient monitoring parameters for the specific patient over time, as well as view and respond to alarms, insights, and/or messages specific to the patient. The user may customize which patient monitoring parameters to view, which trends to view, and which alarms and insights are to be triggered/received for the patient. Further, the user may select from two or more default layouts for how the single-patient GUI is to be configured visually and/or customize the layout of the single-patient GUI (e.g., square tiles arranged in an array, such as shown in FIG. 2, rectangular tiles arranged according to category as shown in FIG. 4A, etc.).

The supervisory application may also enable the user to view multi-patient GUIs where a limited amount of information is viewed for a plurality of different patients. FIGS. 11-16 show example multi-patient GUIs that may be displayed as part of the supervisory application according to embodiments of the present disclosure.

Figure 11:
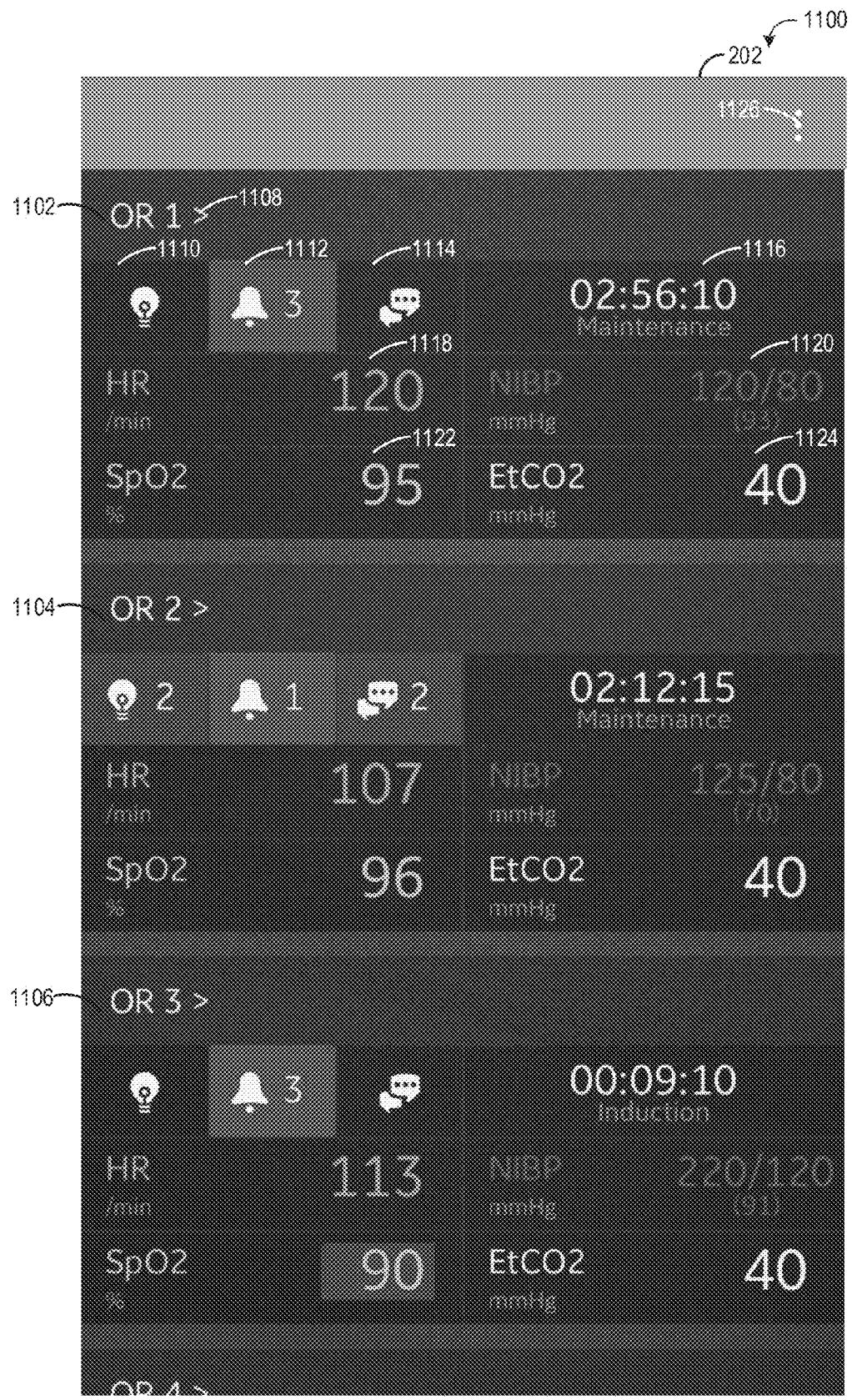
FIGS. 11-15 show the display device displaying various views of a multi-patient graphical user interface generated via the supervisory application.

FIG. 11 shows a multi-patient GUI 1100 displayed on display device 202. Multi-patient GUI 1100 may be displayed in response to launching the supervisory application and/or in response to selection of a back button from a single-patient GUI. Multi-patient GUI 1100 may display information for each of a plurality of patients being overseen by the user of the care provider device associated with display device 202, such as a supervising care provider, as explained above with respect to FIG. 2. As shown in FIG. 11, information for a first patient, a second patient, and a third patient is shown. Information for additional patients may be viewed by scrolling up or down. Each patient may be identified by a patient banner, such as patient banner 1102 (showing that information for the patient in OR 1 is being shown), patient banner 1104 (showing that information for the patient in OR 2 is being shown), and patient banner 1106 (showing that information for the patient in OR 3 is being shown). Each patient banner may include a forward button, such as forward button 1108, or other suitable action button that, when selected, may cause display of the single-patient GUI for that patient. For example, if the forward button in patient banner 1104 is selected, single-patient GUI 200 may be displayed.

A limited amount of patient monitoring information is displayed for each patient via the multi-patient GUI 1100. For example, as shown for the first patient (e.g., located in OR 1), an insights tile 1110, an alarm tile 1112, and a message tile 1114 may all be displayed, similar to the insights tile, the alarm tile, and the message tile of the single-patient GUI 200. However, due to the limited space available, each of the insights tile 1110, alarm tile 1112, and message tile 1114 may be smaller relative to the tiles in the single-patient GUI 200. As appreciated by alarm tile 1112, when an alarm has been triggered for that patient, a number may be displayed in the alarm tile 1112, indicating the number of alarms that have been triggered for that patient. Similar numbers may be displayed in the insights tile 1110 and message tile 1114 when insights or messages, respectively, are triggered or received for that patient. Further, the tile (e.g., alarm tile 1112) may have a different visual appearance when an insight, alarm, or message is triggered or received for the patient. For example, the tile may change in color, become highlighted, or otherwise change in visual appearance to signify the presence of an insight, alarm, or message. An insights tile, an alarm tile, and a message tile may be displayed for each patient.

The patient information that is displayed via the multi-patient GUI 1100 may include a procedure timing tile, such as procedure timing tile 1116, that indicates the phase of the procedure (e.g., phase of anesthesia delivery, such as maintenance) and the current duration of the procedure. Further, as shown in FIG. 11, a plurality of patient monitoring parameter tiles may be displayed for each patient, such as a first patient monitoring parameter tile 1118 (showing heart rate for the first patient patient), a second patient monitoring parameter tile 1120 (showing blood pressure), a third patient monitoring parameter 1122 (showing SpO2), and a fourth patient monitoring parameter 1124 (shown EtCO2). In the example shown in FIG. 11, for each patient, the same patient monitoring parameters may be displayed. The patient monitoring parameters that are displayed via the multi-patient GUI 1100 may be customized by the user, as will be explained below.

Figure 12:
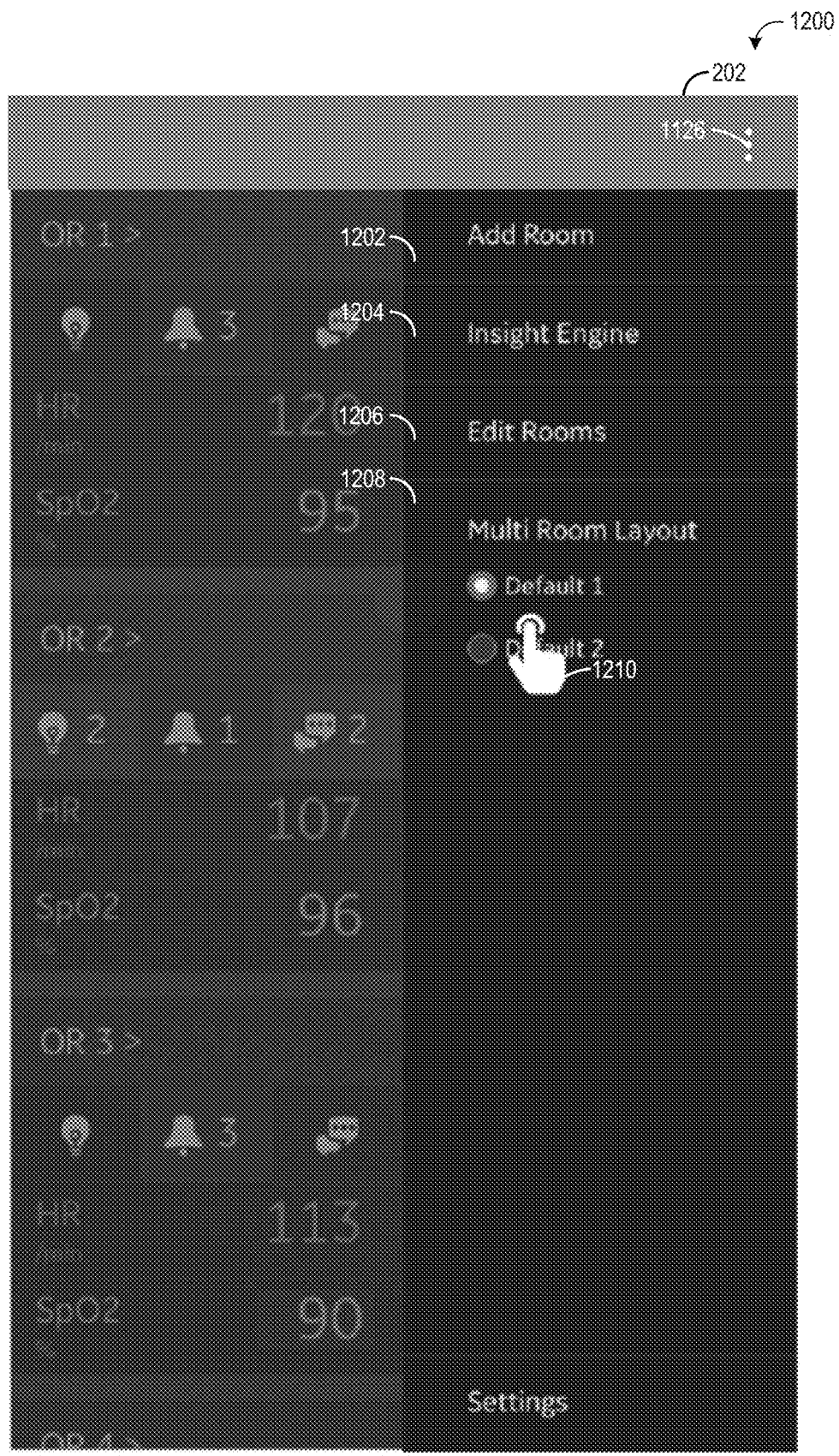

Multi-patient GUI 1100 further includes a menu button 1126. When selected, menu button 1126 may cause a context menu to be displayed, via which various aspects of the multi-patient GUI may be adjusted. FIG. 12 shows an example context menu 1200 that may be displayed on display device 202, for example in response to user selection of the menu button 1126. Context menu 1200 may be similar to context menu 500 of FIG. 5, and thus includes a plurality of control buttons that may trigger different actions. For example, the context menu 1200 may include an add room button 1202, an insights engine button 1204 (which may trigger display of an insights GUI, as will be described in more detail below with respect to FIGS. 17-20), an edit rooms button 1206, and a room layout set of buttons 1208. The room layout set of buttons 1208 may include a button for each different possible layout for how the multi-patient GUI is configured for display. For example, a first layout (e.g., corresponding to multi-patient GUI 1100) may be displayed when the "Default 1" button is selected and a second layout (e.g., corresponding to multi-patient GUI 1300 described below) may be displayed when the "Default 2" button is selected. While not shown in FIG. 12, one or more additional layouts (which may be layouts customized by the user) may be displayed when a "Customize" button is displayed. Additionally, context menu 1200 may include a settings button (shown at the bottom of the context menu) that may cause a settings GUI to be displayed, when selected. Via the settings GUI, various settings of the supervisory application may be adjusted, such as language, notification settings (e.g., sound, vibration), room set-up, add new room, and system alarms. For example, in the system alarms page, preset alarms (e.g., for heart rate, SpO2, and blood pressure) may be turned on or off, and new alarms may be set, at least in some examples.

FIG. 12 shows a user input being entered (shown schematically by hand 1210) to switch from the first layout of multi-patient GUI 1100 to a second layout of multi-patient GUI 1300 of FIG. 13. As a result of the user input, multi-patient GUI 1300 is displayed, as shown in FIG. 13. Multi-patient GUI 1300 may include less information for each patient than multi-patient GUI 1100, and thus more patients may be viewed on one screen. As shown in FIG. 13, multi-patient GUI 1300 includes a plurality of patient banners, such as patient banner 1302 (showing that information for the patient in OR 1 is being shown), patient banner 1304 (showing that information for the patient in OR 2 is being shown), and patient banner 1306 (showing that information for the patient in OR 3 is being shown). Each patient banner may include a forward button, such as forward button 1308, or other suitable action button that, when selected, may cause display of the single-patient GUI for that patient. For example, if the forward button 1301 is selected, single-patient GUI 200 may be displayed.

A limited amount of patient monitoring information is displayed for each patient via the multi-patient GUI 1300. For example, as shown for the first patient (e.g., located in OR 1), an insights tile 1310, an alarm tile 1312, and a message tile 1314 may all be displayed, similar to the insights tile, the alarm tile, and the message tile of the single-patient GUI 200. However, due to the limited space available, each of the insights tile 1310, alarm tile 1312, and message tile 1314 may be smaller relative to the tiles in the single-patient GUI 200. As appreciated by alarm tile 1312, when an alarm has been triggered for that patient, a number may be displayed in the alarm tile, indicating the number of alarms that have been triggered for that patient. Similar numbers may be displayed in the insights tile and message tile when insights or messages, respectively, are triggered or received for that patient. Further, the tile (e.g., alarm tile 1312) may have a different visual appearance when an insight, alarm, or message is triggered or received for the patient. For example, the tile may change in color, become highlighted, or otherwise change in visual appearance to signify the presence of an insight, alarm, or message. An insights tile, an alarm tile, and a message tile may be displayed for each patient. The patient information that is displayed via the multi-patient GUI 1300 may include a procedure timing tile, such as procedure timing tile 1316, that indicates the phase of the procedure (e.g., phase of anesthesia delivery, such as maintenance) and the current duration of the procedure. Multi-patient GUI 1300 also includes a menu button 1318 that may cause context menu 1200 to be displayed when selected.

Figure 14:
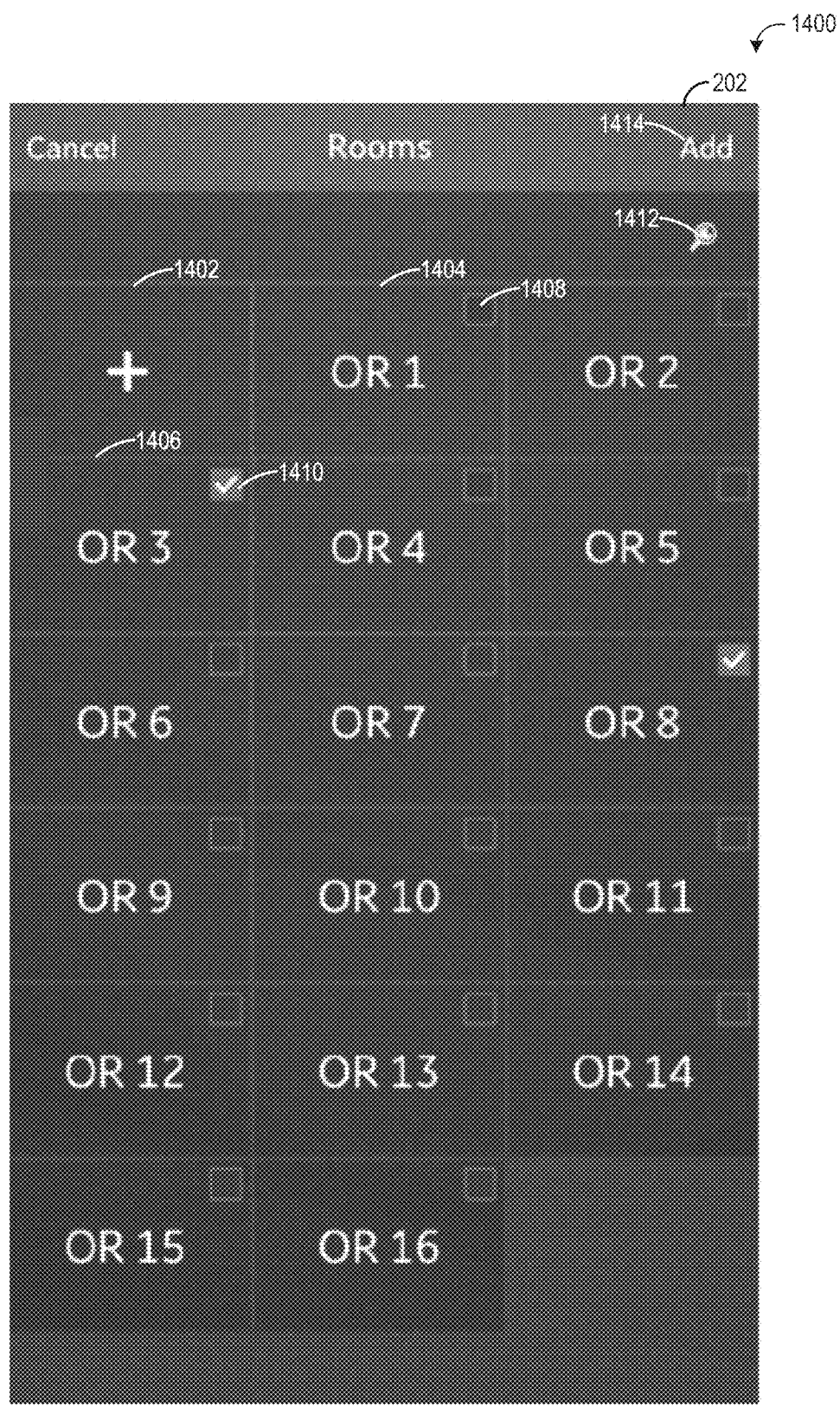

Returning to FIG. 12, as explained above, the context menu 1200 includes an add room button 1202. Selection of the add room button 1202 causes display of an add room page, such as the add room page 1400 shown in FIG. 14. As shown in FIG. 14, the add room page 1400 includes a plurality of square tiles arranged in an array, with the tiles indicating the available rooms which can be added to the multi-patient GUI 1100 or 1300. A first tile 1402 may include a new room button. When selected, the new room button may cause display of rooms not already shown in the add room page 1400. Likewise, the add room page 1400 includes a search button 1412 that may be selected to cause a search box to be displayed so that the user may search for rooms not shown on add room page 1400.

A second tile 1404 shows that OR 1 is available to be added to the multi-patient GUI and a third tile 1406 shows that OR 3 is already added (or has been selected to be added) to the multi-patient GUI. The second tile 1404 includes an unchecked box 1408, signifying that OR 1 has not been added to the multi-patient GUI. User selection of the unchecked box 1408 causes OR 1 to be added to the multi-patient GUI. The third tile 1406 includes a checked box 1410, signifying that OR 3 is already added or is chosen to be added to the multi-patient GUI. User selection of the checked box 1410 will cause OR 3 to be removed from the multi-patient GUI. Once desired rooms have been added or removed, user selection of an add button 1414 will save the added or removed rooms and update the multi-patient GUI accordingly. Changes to the multi-patient GUI, such as adding or removing rooms as explained above, may be saved in the settings/configuration database of the edge device, as explained above with respect to FIG. 1B.

Figure 15:
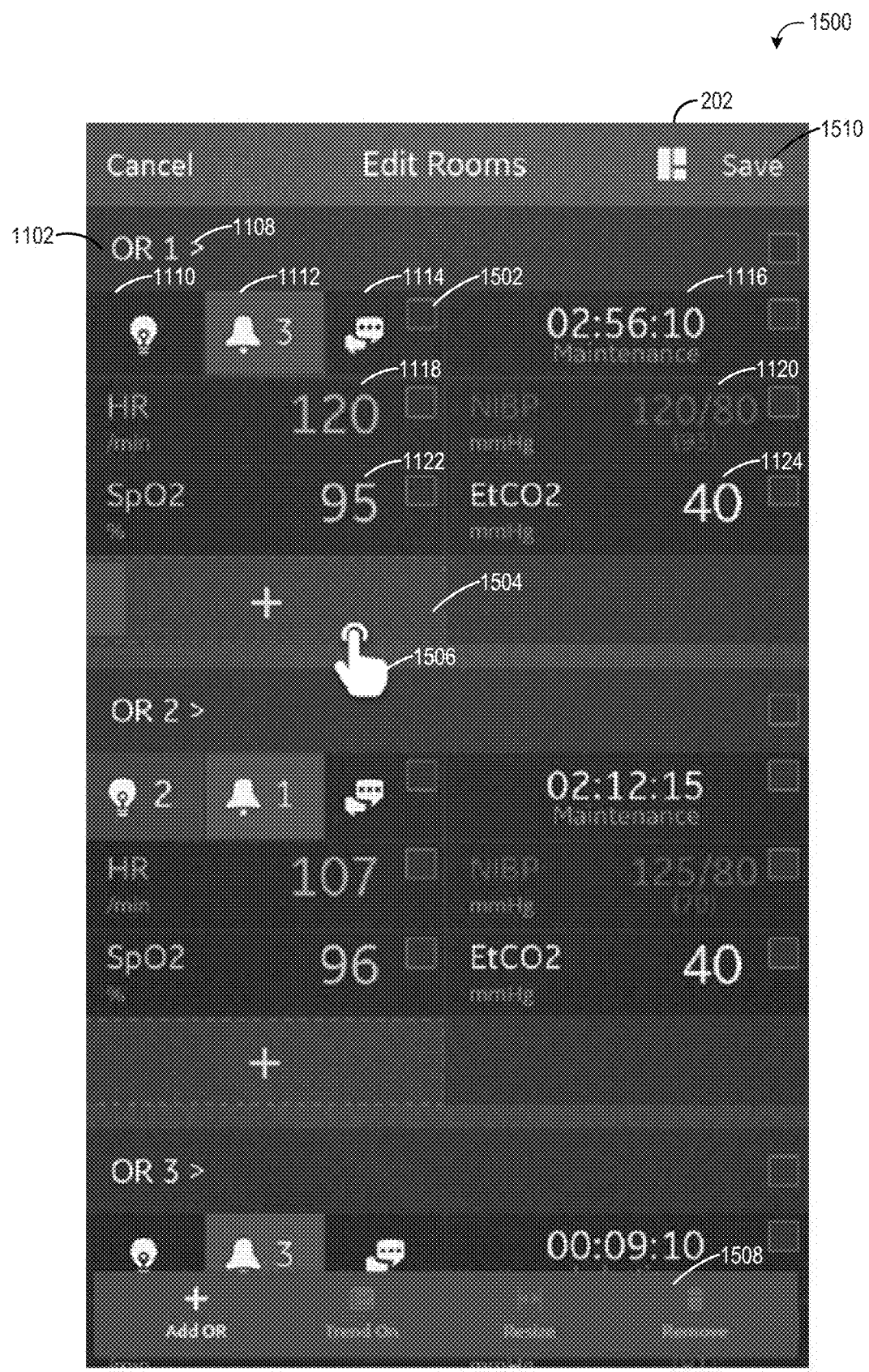

Returning again to FIG. 12, when the edit rooms button 1206 is selected, the multi-patient GUI (in the current layout) may be displayed with selectable control buttons displayed for each currently-selected patient monitoring parameter. FIG. 15 shows an example edit rooms page 1500 that may be displayed in response to selection of the edit rooms button 1206. The edit rooms page 1500 includes a view similar to multi-patient GUI 1100, but also includes selectable control buttons, such as button 1502, within each patient monitoring parameter tile (other than the insights tile and alarm tile, which may not be removed by the user, at least in some examples). User input to a control button may toggle that patient monitoring parameter between being selected (and thus included in the GUI) and not selected (and thus not included in the GUI). Further, additional patient monitoring parameter(s) may be added via an add control button, such as add control button 1504.

Additionally, the edit rooms page 1500 may include an edit banner 1508 that may include various edit functionalities, such as adding a room, turning on a trend for a particular patient monitoring parameter, resizing a patient monitoring parameter tile, and removing a patient monitoring parameter tile. For example, when the user selects a control button, such as the control button that is within tile 1118, the "trend on," "resize," and "remove" buttons may become selectable. By selecting the "trend on" button, a trend for that patient monitoring parameter may be shown, in addition or alternative to the most-recently obtained value for that patient monitoring parameter. When the "resize" button is selected, the tile for that patient monitoring parameter may resized (e.g., made larger or smaller, which may also cause more or less information associated with that patient monitoring parameter to be displayed). When the "remove" button is selected, the tile for that patient monitoring parameter may be removed. Once the user has made desired changes to the patient monitoring parameters shown for each patient, the user may select a save button 1510, which will save and apply the changes to the multi-patient GUI.

Figure 16:
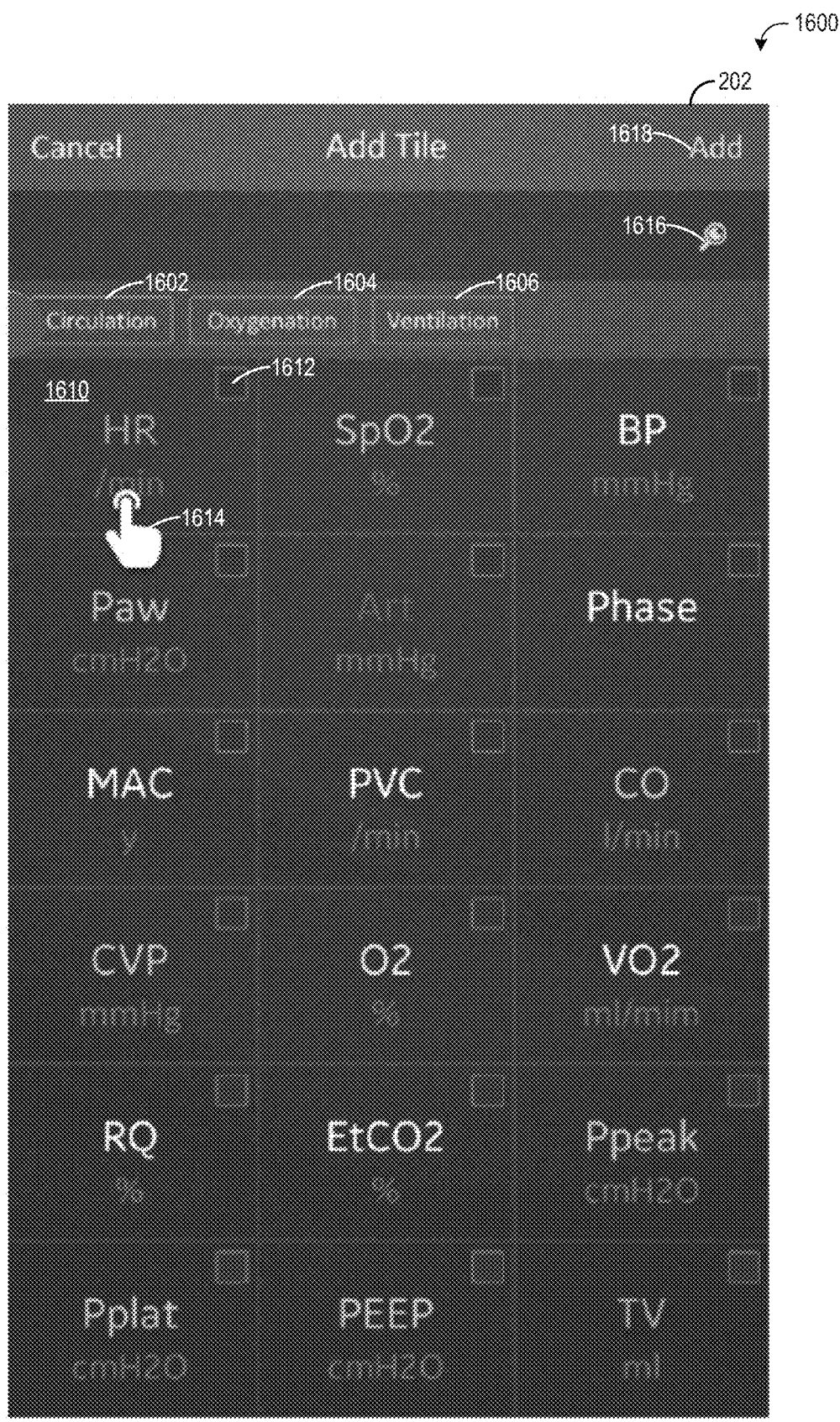
FIGS. 16-20 show the display device displaying various views of an insight graphical user interface generated via the supervisory application.

In the example shown in FIG. 15, a touch input is being entered to the add control button 1504 (shown schematically by hand 1506). As a result, an add tile page is displayed, via which the user may choose patient monitoring parameter tiles to add for the selected patient/room. FIG. 16 shows an example add tiles page 1600. The add tiles page 1600 may include a plurality of patient monitoring parameter buttons arranged in an array. The patient monitoring parameter buttons may each be associated with a patient monitoring parameter. For example, a first patient monitoring parameter button 1610 may be specific to heart rate. The patient monitoring parameter buttons may be organized and displayed by category, which may aid the user in quickly navigating through the plurality of possible patient monitoring parameters to add to the GUI. For example, as shown in FIG. 16, a circulation button 1602 has been selected, causing patient monitoring parameters related to circulation to be displayed on the add tiles page 1600. The add tiles page 1600 also includes an oxygenation button 1604 and a ventilation button 1606, which when selected cause display of patient monitoring parameters related to oxygenation and ventilation, respectively. The add tiles page 1600 also includes a search button 1616 that may cause a search box to be displayed, via which the user may enter search terms to find a desired patient monitoring parameter.

Each patient monitoring parameter button may include a box, such as box 1612. User input to the patient monitoring parameter button may cause the associated box to become checked/selected (if not selected) or unchecked/unselected (if selected). For example, user input to button 1610 (shown by hand 1614) may cause box 1612 to become checked, indicating that heart rate is being chosen to be added as a patient monitoring parameter to be displayed on the GUI. Once the user has made desired edits (e.g., adding desired patient monitoring parameters), an add button 1618 may be selected, causing the selected patient monitoring parameter (s) to be added to the appropriate GUI.

While FIGS. 15 and 16 were described above as being specific to the multi-patient GUI (such as multi-patient GUI 1100), it is to be understood that similar edit rooms and add tiles pages may be displayed when customizing a single-patient GUI. For example, an edit rooms page may be displayed in response to user selection of edit room button 506 of context menu 500, with the edit rooms page including similar functionality as the edit rooms page 1500 (e.g., control buttons to remove, resize, or add trends to patient monitoring parameters that are currently being displayed and control buttons to add patient monitoring parameter tiles).

As explained previously, the supervisory application may apply insights, which may be similar to alarms but may be based on multiple patient monitoring parameters, may be applied conditionally, and so forth, which may provide a more nuanced approach to alerting care providers when patient condition has changed. The insights may include functions that are applied on the received medical device data to determine a current patient status (not otherwise easily determined from viewing individual patient monitoring parameters), predict a future patient status, determine a current phase or portion of a medical procedure, and other applications. The functions may include simple threshold-based comparisons, including one or more patient monitoring parameters and/or limited by a scope, and also may include more complex models and/or algorithms to analyze the received medical device data. As such, the insights described herein may also be referred to as functions.

FIGS. 17-20 show example views of an insights GUI that may be displayed on a care provider device as part of supervisory application 44. Via the insights GUI, a user may be able to define and edit insight rules to be applied to patients being monitored by the user, search for and apply insights created by other users, whether locally (e.g., at the same medical facility) or globally, and view insights that have been triggered for patients being monitored by the user, as explained below.

FIG. 17 shows a first view 1700 of an insights GUI being displayed on display device 202. The insights GUI, and in some examples specifically the first view 1700, may be displayed in response to user selection of an insight engine button from a context menu (e.g., insights engine button 504 of FIG. 5 and/or insights engine button 1204 of FIG. 12) of the supervisory application, or other suitable user input. Via the first view 1700, the user may be able to browse or search for public/shared insights. For example, the first view 1700 includes a search box 1702. The user may enter search terms into the search box 1702, and the supervisory application may display any relevant insights in response.

The first view 1700 includes a first section of insights, referred to as the "quick picks" section, where insights that have been developed by other users may be browsed. For example, a first insight tile 1704 is displayed in the quick picks section. The first insight tile 1704 may include an indication of the insight rules (e.g., trigger an insight if total flow is greater than 6 pounds a minute for 10 minutes) for a first insight. The first insight tile 1704 may also include an indication of how many users have applied the first insight. The first view 1700 may include four insight tiles displayed as part of the quick picks section, but other numbers of insight tiles are possible. Further, additional insight tiles created by other users may be viewed by selecting the "view all" button within the quick picks section.

The insights that are displayed as part of the quick picks section may be generated by all users, whether locally or at other medical facilities. In some examples, the insights in the quick picks section may be organized by popularity, such that the insights that have been applied by the most users may be displayed first. However, other methods for organizing and presenting the insights are possible, such as by patient monitoring parameter.

The first view 1700 further includes a second insights section, referred to as a "hospital insights" section, where insights created by users at the same medical facility may be browsed. For example, the hospital insights section includes a second insight tile 1706, where insight rules for a second insight are displayed, along with the number of users applying the insight and the author of the insight. The first view 1700 may include four insight tiles displayed as part of the hospital insights section, but other numbers of insight tiles are possible. Further, additional insight tiles created by other users at the medical facility may be viewed by selecting the "view all" button within the hospital insights section.

The insights that are displayed as part of the hospital insights section may be generated only by users that attend to patients at the medical facility where the user interacting with the first view 1700 (e.g., the user of the care provider device associated with display device 202) attends to patients. In this way, the user may browse insights from trusted sources that conform to any internal standards or guidelines applied by the medical facility or other administrative organization. In some examples, the insights in the hospital insights section may be organized by popularity, by patient monitoring parameter, by date the insight was created, etc.

The first view 1700 includes a plurality of control buttons displayed along a bottom of the first view 1700. The control buttons include a discover button 1708, an activity button 1710, and a my insights button 1712. When the discover button 1708 is selected, the first view 1700 may displayed, which may enable the user to discover/search for new insights. When the activity button 1710 is selected, a second view of the insights GUI may be displayed where a list of the user's selected insights, and in some examples alarms, that have been applied to a patient may be viewed. When the my insights button 1712 is selected, a third view of the insights GUI may be displayed where the user may add, remove, and edit insights.

Figure 18:
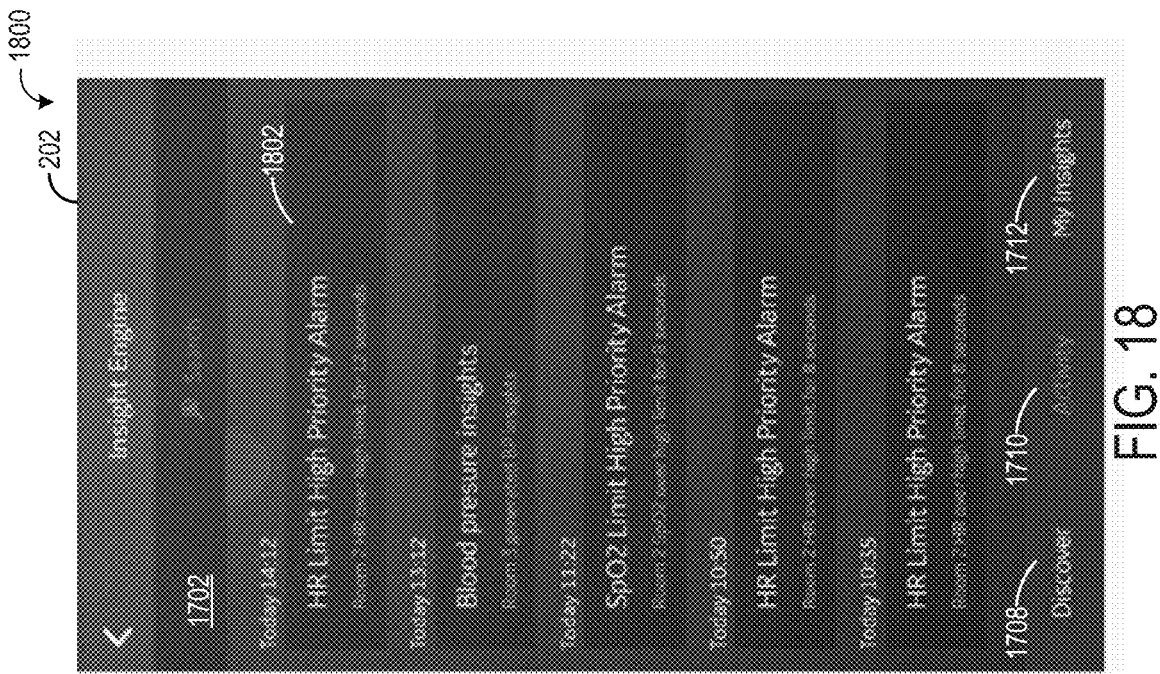

FIG. 18 shows an example of a second view 1800 of the insights GUI that may be displayed in response to user selection of an activity button, such as activity button 1710. The second view 1800 includes the search box 1702, the discover button 1708, the activity button 1710, and the my insights button 1712, similar to the first view 1700. The second view includes a list of insights and alarms that have been applied to one or more patients. The insights and alarms that are listed in the second view 1800 may include insights and alarms chosen by the user to be applied to the patients being monitored by the user, that were applied to a patient during the course of a procedure where the patient was being monitored/treated by one or more of the medical devices described herein. For example, a first applied insight tile 1802 is displayed in the first view 1800. The first applied insight tile 1802 includes an indication of the rules of the insight/alarm that was applied, herein a heart rate limit high priority alarm. The tile 1802 further includes an indication of when the insight/alarm was triggered (e.g., today at 14:12), on which patient (e.g., the patient in room 2), and for how long the triggering condition persisted (e.g., for 12 seconds). The applied insights/alarm tiles may be organized chronologically, reverse-chronologically, or in another suitable manner.

Figure 19:

FIG. 19 shows an example of a third view 1900 of an insights GUI that may be displayed in response to user selection of a my insights button (e.g., my insights button 1712). The third view 1900 includes the discover button 1708, the activity button 1710, and the my insights button 1712, similar to the first view 1700 and second view 1800. In the third view 1900, a list of all alarms and insights saved/selected by the user are shown, including alarms/insights that are selected to be applied and alarms/insights that are currently not being applied. For example, a first tile 1902 includes an indication of the rules of the alarm/insight (e.g., SpO2 high alarm) and an indication of which patients that alarm/insight is be applied to (e.g., all patients). The tile 1902 also includes an on/off button 1904 showing that the alarm/insight is on, which indicates that the alarm/insight will be applied with patient monitoring parameters meeting the alarm/insight rules. The third view 1900 includes a second tile 1906 that includes alarm/insight rules (e.g., arterial mean pressure high alarm) and who the alarm/insight applies to (e.g., all). The second tile 1906 includes an on/off button 1908 showing that the alarm/insight is no longer being applied.

If the user selects an alarm or insight listed in the third view 1900, or if the user selects an add alarm/insight button 1910, a fourth view 2000 of the insights GUI may be displayed, as shown in FIG. 20. Via the fourth view 2000, aspects of the alarm/insight may be edited. For example, the fourth view 2000 includes an information tile 2002 for the selected insight/alarm, which indicates the insight rules (e.g., if heart rate is greater than 150 beats/minute for 5 minutes during maintenance phase), priority level (e.g., level 1), and who the insight is to be applied to (e.g., all rooms). The tile 2002 includes a toggle button 2004 that the user may move to turn the insight on (as shown) or off. Further, the fourth view 2000 includes an edit button 2006 and a delete button 2008. When selected, the edit 2006 button may cause display of an edit page, where aspects of the insight may be changed. When selected, the delete button 2008 may cause the selected insight to be removed from the user's list of insights (e.g., the insight will not be shown in the third view 1900). In some examples, the fourth view 2000 may include a share insight button 2010 that may change the privacy settings of the displayed insight from private to public when selected. For example, the insight displayed in FIG. 20 is marked as private, but selection of share insight button 2010 may switch the privacy setting to public. Once the privacy setting is changed to public, other uses may view and apply the insight, if desired.

Figure 29:
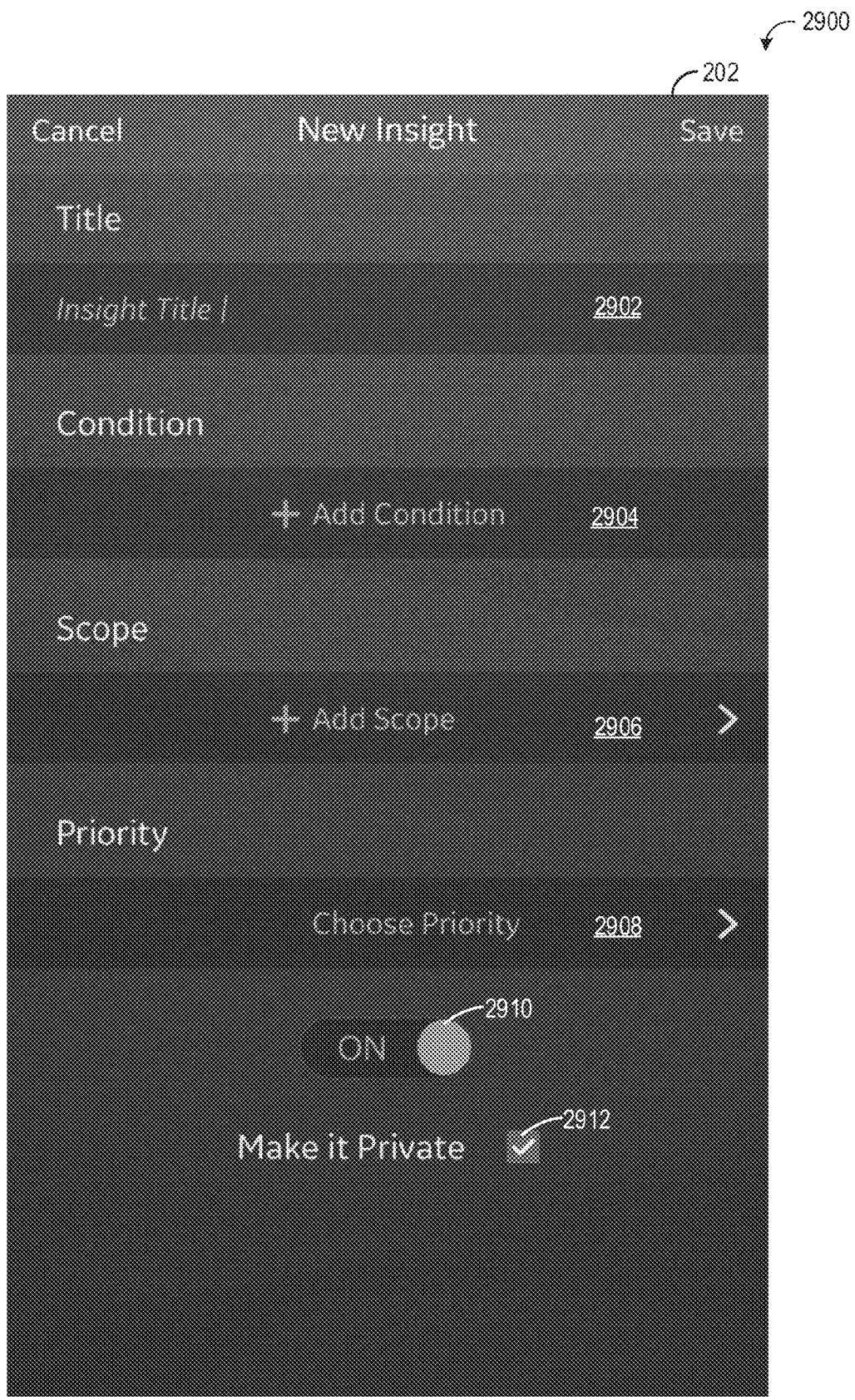
FIG. 29 shows an example display device displaying a new insights view generated via the supervisory application.

The example insight shown in FIG. 20 may include a condition (heart rate being greater than 150 beats per minute) and two scopes, the condition persisting for a specified amount of time (e.g., five minutes) and the condition occurring during a particular time of the procedure (e.g., during maintenance phase). The user may create the example insight via a new insights view of the insights GUI. FIG. 29 shows an example new insights view 2900 that may be displayed on display device 202 in response to a user request to create a new insight, such as in response to user selection of a new insight button (e.g., button 1910 of FIG. 19). Via the new insights view 2900, a user may enter a title for the insight in a title box 2902, add a condition for the insight via a condition menu 2904, add a scope for the condition via a scope menu 2906, and select a priority for the insight (e.g., low, medium, or high) via a priority menu 2908.

The condition(s) that may be added via the condition menu 2904 may be selected from a predefined set of parameters. The predefined set of parameters may include any patient monitoring parameter available in the system, and thus selection of the condition menu 2904 may launch a view that is similar to the view shown in FIG. 16 where available patient monitoring parameters are shown and may be selected for the condition. The predefined set of parameters may include other insights that the user has created or selected to be applied. Once a patient monitoring parameter is selected, a threshold for that parameter may be entered. The scope for the condition may be fully user defined (e.g., the user may enter text to define the scope) or the scope menu 2906 may include different types of scopes from which the user may select (e.g., number of minutes the condition is to persist, the phase of the procedure the condition is to occur in, etc.). The scope menu may include a predefined set of operators, such as "and", "or", "while", and so forth, that may allow the user to create an insight having multiple parameters and/or multiple scopes. In doing so, the user may gain more knowledge of patient status than by relying on the machine-generating alarms, which may only track a single patient monitoring parameter.

Further, the user may select to turn on the insight via an on/off button 2910 and may adjust the privacy setting of the insight, such as share the insight or make the insight private, via a share selection box 2912. Once the user has created the insight and set all the insight parameters, the insight may be saved by selecting the save button.

Thus, the supervisory application may allow a user, such as a supervising care provider, to oversee multiple patients at one time, from any location within a medical facility. The supervisory application may present patient monitoring parameters in real-time, as well as historical data such as changes in patient monitoring parameters over time, via a plurality of GUIs, as explained above. The GUIs presented above with respect to FIGS. 2-20 may be a first set of GUIs that are displayable if the user is a supervising care provider. For example, upon initially launching the supervisory application, the user may be authenticated via a suitable authentication mechanism. The authentication process may include determining if the user is a supervising care provider (e.g., anesthesiologist supervising multiple nurse anesthesiologists) or if the user is a subordinate care provider (e.g., one of the nurse anesthesiologists). Once the supervisory application has confirmed the identity of the user via the authentication process, the supervisory application may access care provider information stored in memory of a device of the hospital network (e.g., on the edge device, on a hospital operations system device) or available remotely (e.g., via the MDD processing system or other cloud-based service) to determine which care providers the user is supervising (if the user is a supervising care provider) or determine which care provider is supervising the user (if the user is a subordinate care provider), in order to coordinate communication among the supervising care providers and the associated one or more subordinate care providers. If the user is identified as a supervising care provider, the GUIs presented above with respect to FIGS. 2-20 may be displayed on the user's device when prompted. However, if the user is identified as a subordinate care provider, the GUIs presented above may not be displayed. Instead, an in-room GUI that presents information for only for a single patient may be displayed. As will be discussed in more detail below with respect to FIGS. 21-23, the in-room GUI may present real-time patient monitoring parameters for a patient and alarm notifications, similar to the single-patient GUIs described above. The in-room GUI may also facilitate rapid communication between the in-room (e.g., subordinate) care provider and the supervising care provider via a one-touch/click consultation button (which requests a consultation with the supervising care provider), a message button that launches a message thread with the supervising care provider, and a snapshot button that captures an image of the current patient monitoring parameters being viewed via the in-room GUI. This image may be sent to the supervising care provider, which may allow the supervising care provider to quickly assess patient state without having to navigate to the supervising care provider's own single-patient GUI for that patient.

Figure 21:
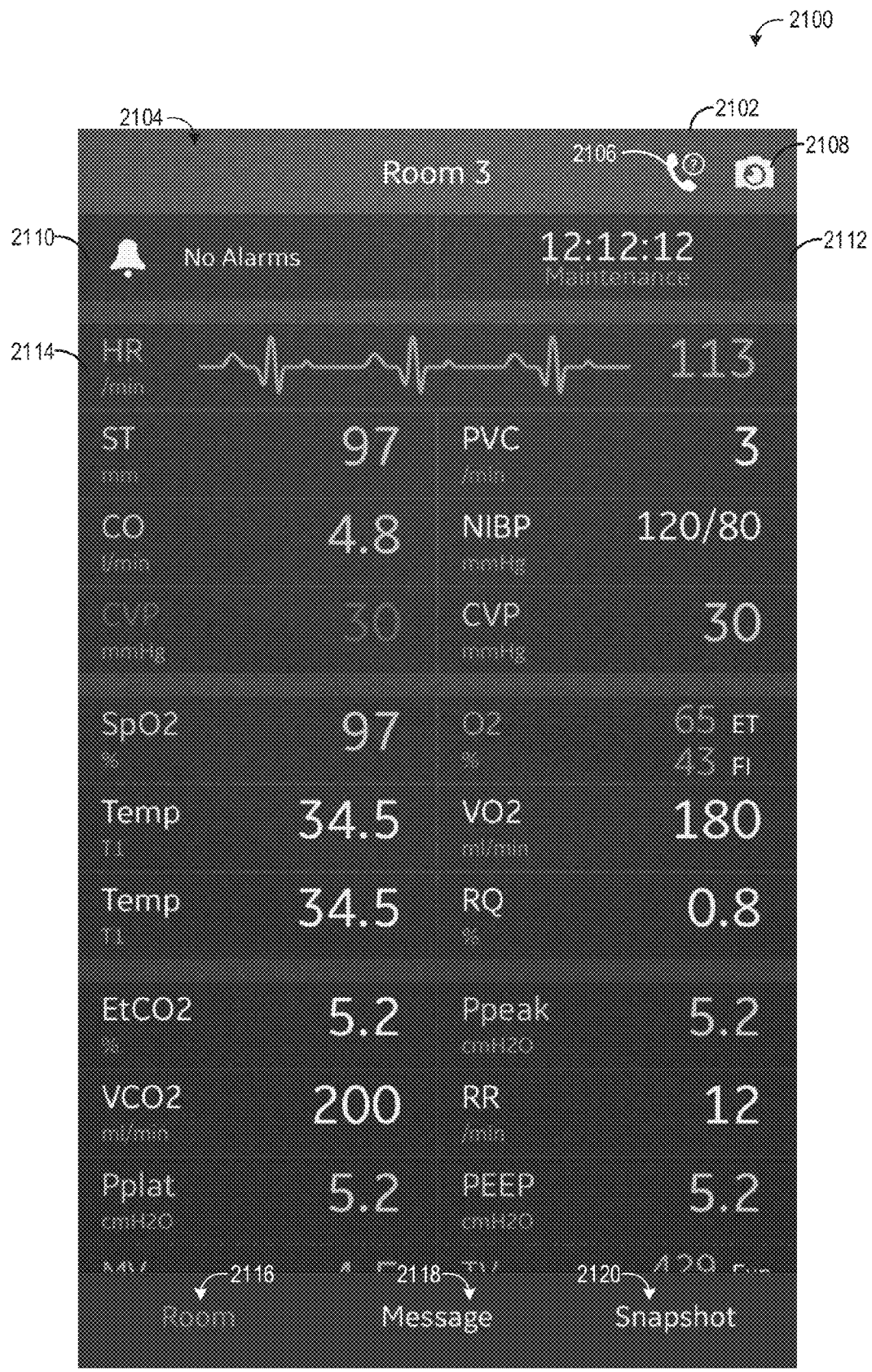
FIGS. 21-23 show an example display device displaying various views of an in-room graphical user interface generated via the supervisory application.
Figure 23:
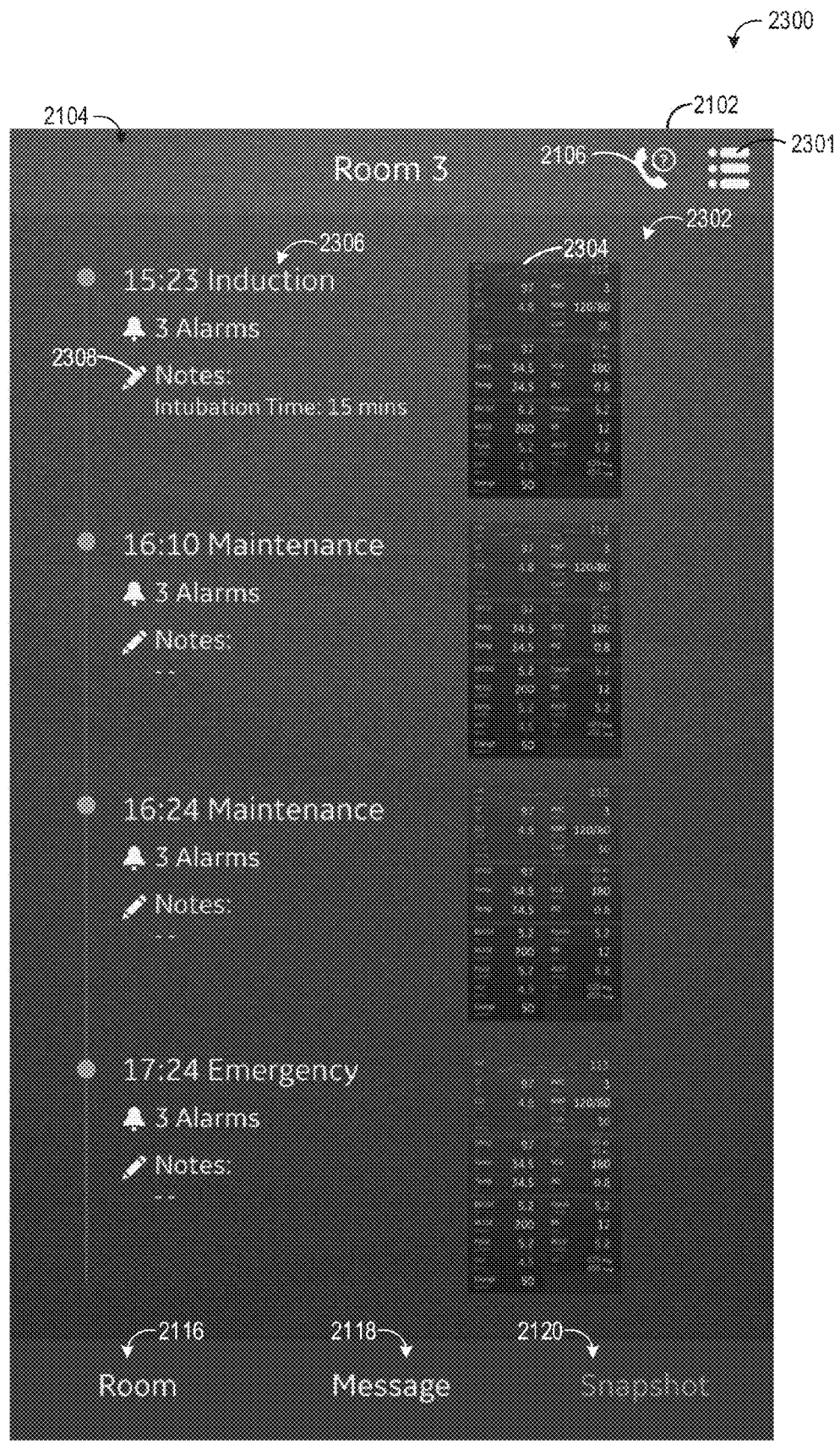

FIGS. 21-23 show various views or pages of an in-room GUI that may be displayed to a subordinate care provider. FIG. 21 shows a first view of an in-room GUI 2100 being displayed on a display device 2102. Display device 2102 may be associated with a care provider device, such as care provider device 136. In-room GUI 2100 may include an identification header 2104 that identifies the room or patient that the GUI is showing patient monitoring parameters for, herein room 3. The identification header 2104 includes a call button 2106. When selected, the call button 2106 may send a request for a consultation to the care provider device of the care provider overseeing the user of the device on which the in-room GUI is being displayed. For example, the in-room GUI may be viewed on a care provider device (e.g., care provider device 136) by a nurse anesthesiologist attending to the patient in room 3, and selection of the call button 2106 may cause a consultation request to be sent to the care provider device (e.g., care provider device 134) of the supervising anesthesiologist that is supervising the nurse anesthesiologist, but who is in a different location (e.g., in a different room in the medical facility). The identification header 2104 also includes a snapshot button 2108. When selected, the snapshot button 2108 takes a snapshot (e.g., an image) of the currently-displayed in-room GUI and saves the captured image in memory, where the captured image can be sent to the supervising care provider and/or annotated with additional information, as will be described in more detail below.

The in-room GUI 2100 includes an alarm tile 2110 and a procedure timing tile 2112. The alarm tile 2110 may include an indication of how many alarms have been triggered for the patient, similar the alarm tile explained above with respect to FIG. 9, for example. When selected, the alarm tile 2110 may cause an explanation of each triggered alarm to be displayed within the in-room GUI 2100, as explained above with respect to FIG. 9. The procedure timing tile 2112 may include an indication of the current phase of the procedure as well as the total elapsed duration of the procedure being carried out on the patient.

The in-room GUI 2100 includes a plurality of patient monitoring tiles, such as patient monitoring tile 2114 (which is displaying patient heart rate both as a representative ECG waveform and as a most-recently determined value). The patient monitoring parameters that are displayed via the in-room GUI 2100 may not be customized by the user of the in-room GUI. Rather, the patient monitoring parameters that are displayed in the in-room GUI 2100 may be synched with the patient monitoring parameters that have been selected by the supervising care provider to be displayed in the single-patient GUI for that patient. For example, the supervising care provider may customize a single-patient GUI for room 3, as explained above with respect to FIGS. 15 and 16. The patient monitoring parameters selected by the supervising care provider to be included in the single-patient GUI for room 3 may also be included in the in-room GUI 2100. This may include the inclusion of the patient monitoring parameters and may also include whether the value(s) for each patient monitoring parameter is viewed as a trend/waveform and/or most-recently determined value and the location of each patient monitoring parameter tile. In this way, the information and the visual appearance of the in-room GUI may mimic the corresponding single-patient GUI.

The in-room GUI 2100 includes a plurality of control buttons that may be displayed along a tile at the bottom of the in-room GUI 2100 or other location. The plurality of control buttons includes a room view button 2116, a message view button 2118, and a snapshot view button 2120. When selected, the room view button 2116 causes the first view of the in-room GUI to be displayed (e.g., as shown in FIG. 21). The message view button 2118, when selected, causes display of a message view where a message thread between the subordinate care provider and supervising care provider may be viewed and carried out, which is shown in FIG. 22 and described in more detail below. The snapshot view button 2120, when selected, causes display of a snapshot view where snapshots of the in-room GUI that have been captured via the snapshot button may be displayed and annotated, as shown in FIG. 23 and described in more detail below.

FIG. 22 shows a message view 2200 of the in-room GUI 2100 that may be displayed when the message view button 2118 is selected. The message view 2200 includes the identification header 2104, including the call button 2106 and the snapshot button 2108. The message view 2200 also includes the room view button 2116, the message view button 2118, and the snapshot view button 2120.

The message view 2200 includes a message thread 2202 occurring between the user of the in-room GUI 2100 (e.g., the subordinate care provider) and the corresponding supervising care provider. The message thread 2202 may include text messages (e.g., the message stating "cannot resolve alarm, need help!" read at 16:26). When desired, the user may send a snapshot of a view of the in-room GUI, such as a snapshot of the first view shown in FIG. 22. Thus, as shown, the message thread 2202 includes a snapshot 2204 of the first view of the in-room GUI 2100 that includes the patient monitoring parameters. In this way, when the subordinate care provider requests assistance or advice from the supervising care provider, the subordinate care provider may send a message (by entering text into message box 2206 or by entering voice input) explaining the issue the subordinate care provider is having (e.g., an alarm that cannot be resolved), and if the subordinate care provider thinks it may be helpful, the subordinate care provider may send a snapshot of the values of the patient monitoring parameters displayed via the in-room GUI. The supervising care provider may then be able to assess current patient state, machine settings, and/or other relevant information (e.g., additional information conveyed by the subordinate care provider via the message thread) in a single view, without having to navigate to other GUIs or pages. The supervising care provider may then send advice or instructions to the subordinate care provider via the message thread.

The supervising care provider may view the message thread 2202 on the supervising care provider's device. For example, as shown in FIG. 4A, the single-patient GUI 200 may include a message tile 304. When a message is received from a subordinate care provider that is specific to the patient of the single-patient GUI 200, the message tile 304 may include an indication that a message is available. When the message tile 304 is selected, the message thread between the supervising care provider and the subordinate care provider may displayed, for example in a manner similar to the message thread shown in FIG. 10.

FIG. 23 shows a snapshot view 2300 of the in-room GUI 2100 that may be displayed when the snapshot view button 2120 is selected. The snapshot view 2300 includes the identification header 2104, including the call button 2106 and a format button 2301. The snapshot view 2300 also includes the room view button 2116, the message view button 2118, and the snapshot view button 2120.

The snapshot view 2300 includes a list of snapshots 2302 captured by the user for the patient (e.g., of the in-room GUI for room 3) displayed in a timeline format. Each snapshot included in the list of snapshots 2302 includes a captured image 2304 (e.g., the snapshot) and corresponding information 2306. The corresponding information 2306 may include the timing and the phase of the procedure when the snapshot was taken (e.g., 15:23 induction), how many alarms were triggered for the patient when the snapshot was taken (e.g., 3 alarms), and notes as entered by the user. The notes may be entered and/or edited by selecting a notes button 2308. In the example shown in FIG. 23, the notes entered by the user includes an indication that the patient had been intubated for 15 minutes when the snapshot was taken. In some examples, user selection of the alarms shown in the corresponding information 2306 may trigger display of information pertaining to the alarms that were triggered for the patient at the time the snapshot was taken. Further, the captured images, such as captured image 2304, shown in the snapshot view 2302 may be zoomed out/miniaturized images so that multiple images may be viewed on one screen. While this may facilitate quick viewing of each snapshot, it may be difficult for the values of the patient monitoring parameters in each snapshot to be viewed. Thus, at least in some examples, each captured image may be viewed in a separate page when that image is selected. The snapshots and associated information shown in FIG. 23 are arranged chronologically into a timeline. However, selection of the format button 2301 may cause the snapshot view to be displayed in a different format, for example in a phases format where the snapshots for a given patient and procedure are arranged by procedure phase, such as by anesthesia phase. The phases format may include a similar format button that, when selected, causes the timeline format of the snapshots to be displayed.

Figure 24:
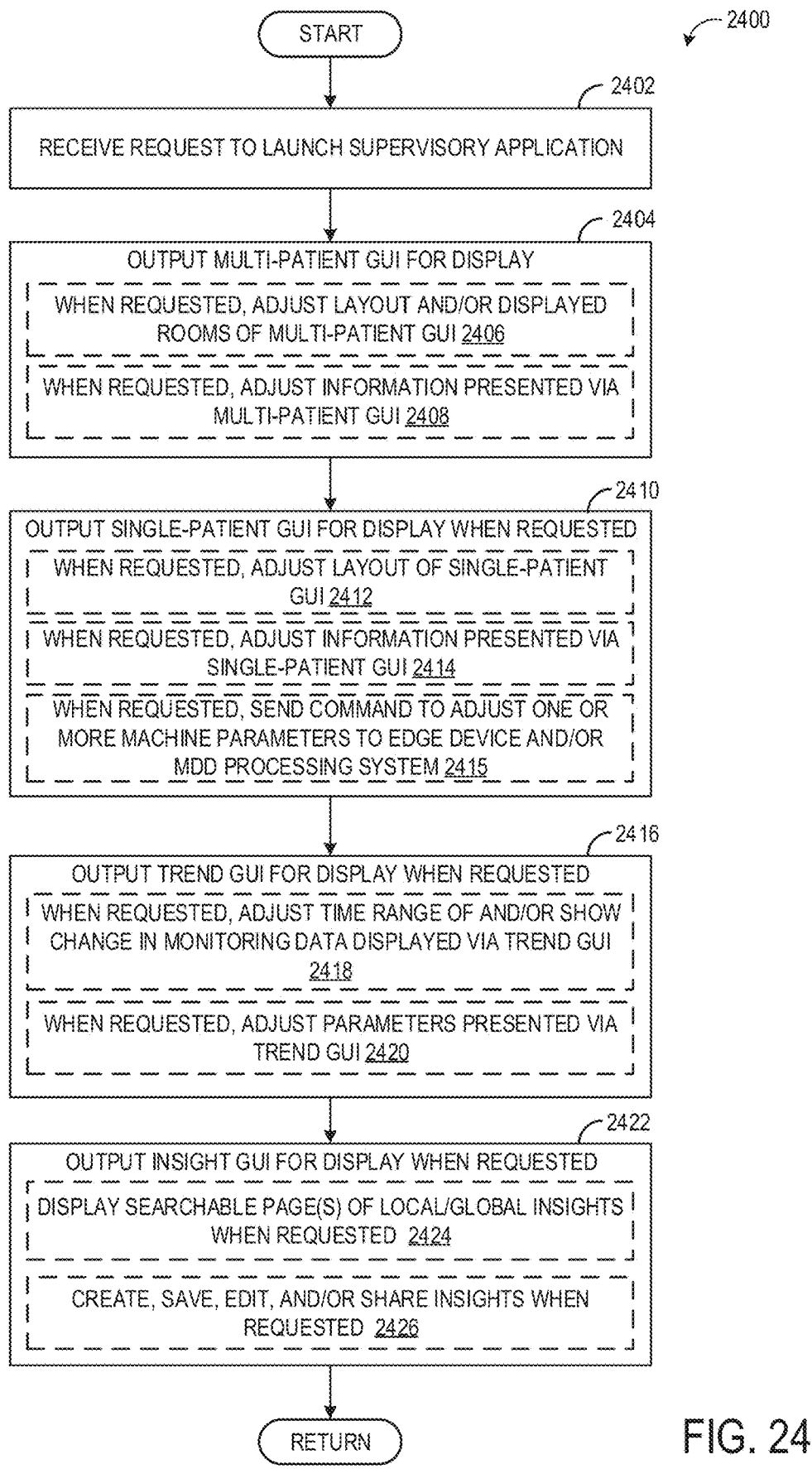
FIG. 24 is a flow chart illustrating an example method for displaying supervising graphical user interfaces generated via the supervisory application.

FIG. 24 is a flow chart illustrating an example method for displaying supervising graphical user interfaces generated via a supervisory application on a display device associated with a care provider device. Method 2400 may be implemented by a care provider device (such as care provider device 134) being used by a supervising care provider in combination with an edge device connected to the care provider device (e.g., edge device 20), a cloud in communication with the edge device and/or care provider device (e.g., MDD processing system 12), or any appropriate combination thereof.

At 2402, a request to launch the supervisory application is received. The request to launch the supervisory application may be received via user input, such as a user of the care provider device selecting a supervisory application icon displayed on a home page or other location of the display device associated with the care provider device. Upon the request to launch the supervisory application being received, a multi-patient GUI is output for display on the display device, as indicated at 2404. In some examples, the multi-patient GUI may be the default page for the supervisory application, such that any time the supervisory application is launched from an unlaunched state, the multi-patient GUI is displayed. Further, in some examples, prior to displaying the multi-patient GUI and after the request to launch the supervisory application is received, an authentication/log-in page may be displayed, via which the user may enter log-in information via text input, via a captured image (e.g., facial recognition), via a fingerprint, or other suitable mechanism for entering credentials for authentication. Once the user is authenticated, the multi-patient GUI may be launched. In still further examples, if the user has not already set up their view of the supervisory application, a set-up page may be displayed after user authentication, via which the user may select which rooms/patients to display in the multi-patient GUI.

As an example, after launching the supervisory application and authenticating the user, the supervisory application may display an initial set-up page, which may include a menu button (similar to menu button 1126 of FIG. 11) that when selected causes display of a context menu that includes an add room button, similar to the context menu 1200 and the add room button 1202 of FIG. 12. When the user selects the add room button, an add rooms page may be displayed, similar to the add rooms view 1400 of FIG. 14. The user may then select which rooms/patients are to be added to the multi-patient GUI. In some examples, the initial set-up page may include an add room box or other more direct mechanism that when selected by the user causes display of the add rooms view.

The multi-patient GUI may include limited information for each of a plurality of patients. For example, the multi-patient GUI 1100 of FIG. 11 includes, for each selected room/patient, a subset of all available patient monitoring parameters that may be viewed for that patient (e.g., the patient monitoring parameter tiles 1118, 1120, 1122, and 1124) and one or more alert and timing tiles, such as an alarm tile (e.g., alarm tile 1112), a message tile (e.g., message tile 1114), an insights tile (e.g., insights tile 1110), and a procedure timing tile (e.g., procedure timing tile 1116). The layout of the multi-patient GUI and/or the rooms that are displayed as part of the multi-patient GUI may be adjusted when requested, as indicated at 2406. For example, the multi-patient GUI 1100 of FIG. 11 may be a first layout for the multi-patient GUI, and the user may select to switch to a different layout, such as the layout of the multi-patient GUI 1300 of FIG. 13, by selecting the appropriate layout from the context menu. The second layout shown in FIG. 13 may include the alert and timing tiles, but may not include any patient monitoring parameter tiles. Further, the user may add or remove rooms/patients from the multi-patient GUI by selecting the add rooms button of the context menu (e.g., button 1202 of menu 1200), which may launch the add rooms view 1400. As explained above, via the add rooms view, the user may add rooms/patients to the multi-patient GUI and may also remove rooms/patients from the multi-patient GUI.

In some examples, the user may further customize the layout of the multi-patient GUI by adjusting the information presented via the multi-patient GUI, as indicated at 2408. As explained previously, the multi-patient GUI may display, via the subset of patient monitoring parameters, real-time determined values for each of the patient monitoring parameters, as received from one or more medical devices (e.g., the medical devices 16 of FIG. 1A, which may include physiological monitoring devices 16a as well as patient therapy devices 16b, e.g., anesthesia delivery machines) and streamed from an intermediary device (e.g., streamed from the streaming server 114 of the edge device 20). The user may customize which patient monitoring parameters are included in the multi-patient GUI by selecting an edit rooms button of the context menu, such as edit rooms button 1206 of menu 1200, which may cause an edit rooms view to be displayed, such as the edit rooms page 1500 of FIG. 15. Via the edit rooms view, the user may add or remove patient monitoring parameters to the multi-patient GUI in a patient/room-specific manner, select to view the patient monitoring parameters as trends or single values, and/or resize the tiles for the patient monitoring parameters.

At 2410, a single-patient GUI may be output for display when requested. The single-patient GUI may include notifications/alerts and/or patient monitoring parameters for a single patient, rather than multiple patients. Example single-patient GUIs are shown in FIGS. 2 and 4A and explained above. The single-patient GUI may be output for display in response to a user request, such as the user selecting a room/patient from the multi-patient GUI. For example, referring to FIG. 13, user selection of the forward button 1301 may cause single-patient GUI 200 to be displayed. The single-patient GUI may include more information for the selected patient than the corresponding information in the multi-patient GUI for that patient, thus allowing the care provider to drill down to a more-detailed for a single patient when desired.

The single-patient GUI, similar to the multi-patient GUI, may be customized by the user to have a desired layout, display desired information, and so forth. Thus, as indicated at 2412, the layout of the single-patient GUI may be adjusted when requested. The layout may be adjusted similarly to the layout adjustment of the multi-patient GUI, e.g., in response to user selection of a desired layout from a context menu (e.g., context menu 500 of FIG. 5). Further, as indicated at 2414, the information presented via the single-patient GUI may be adjusted when requested. Similar to the multi-patient GUI, the single-patient GUI may be adjusted via an edit rooms view and/or add tiles view similar to the edit rooms page 1500 of FIG. 15 and add tiles page 1600 of FIG. 16.

In some examples, a user may request to add a patient monitoring parameter to the single-patient GUI, remove a patient monitoring parameter from the single-patient GUI, request to view a patient monitoring parameter as a value or as a trend in a tile, request to view the result of an insight as a tile on the single-patient GUI, or perform another action that may cause the layout of the single-patient GUI to change. In such examples, one or more of the remaining patient monitoring parameter tiles on the single-patient GUI may be adjusted in response to the user action. For example, one or more patient monitoring parameter tiles may be moved, resized, scaled, etc., to accommodate a newly added tile, take up space left by a removed tile, and so forth. The adjustments may be performed automatically by the supervisory application in some examples. When a tile is resized, different information may be displayed in a smaller tile versus a larger tile. As an example, if a user chooses to view a patient monitoring parameter as a trend rather than or in addition to a value, that patient monitoring parameter tile may be increased in size and more information may be displayed. If a patient monitoring parameter tile is reduced in size, less information may be shown. Further, each patient monitoring parameter tile may have seven states: a numerical state, an edit state, a selected state, a trend state, a waveform state, an alarm state, and a drag state, which may be displayed according to user input. The numerical state may show only a value for that parameter, the edit state may include a checkbox allowing the user to select or deselect the parameter (thus adding or deleing the tile), the selected state may include a visual indication that the tile has been selected by the user (e.g., highlighting), the trend state may include a trend of the parameter over time (e.g., a trend line), the waveform state may show the parameter as a waveform rather than value (e.g., ECG waveform), the alarm state may highlight the value of the parameter if an alarm condition is reached, and the drag state may include the tile having a visual appearance indicating the user is dragging the tile (e.g., to a new location), such as the tile changing color or transparency.

Figure 28:
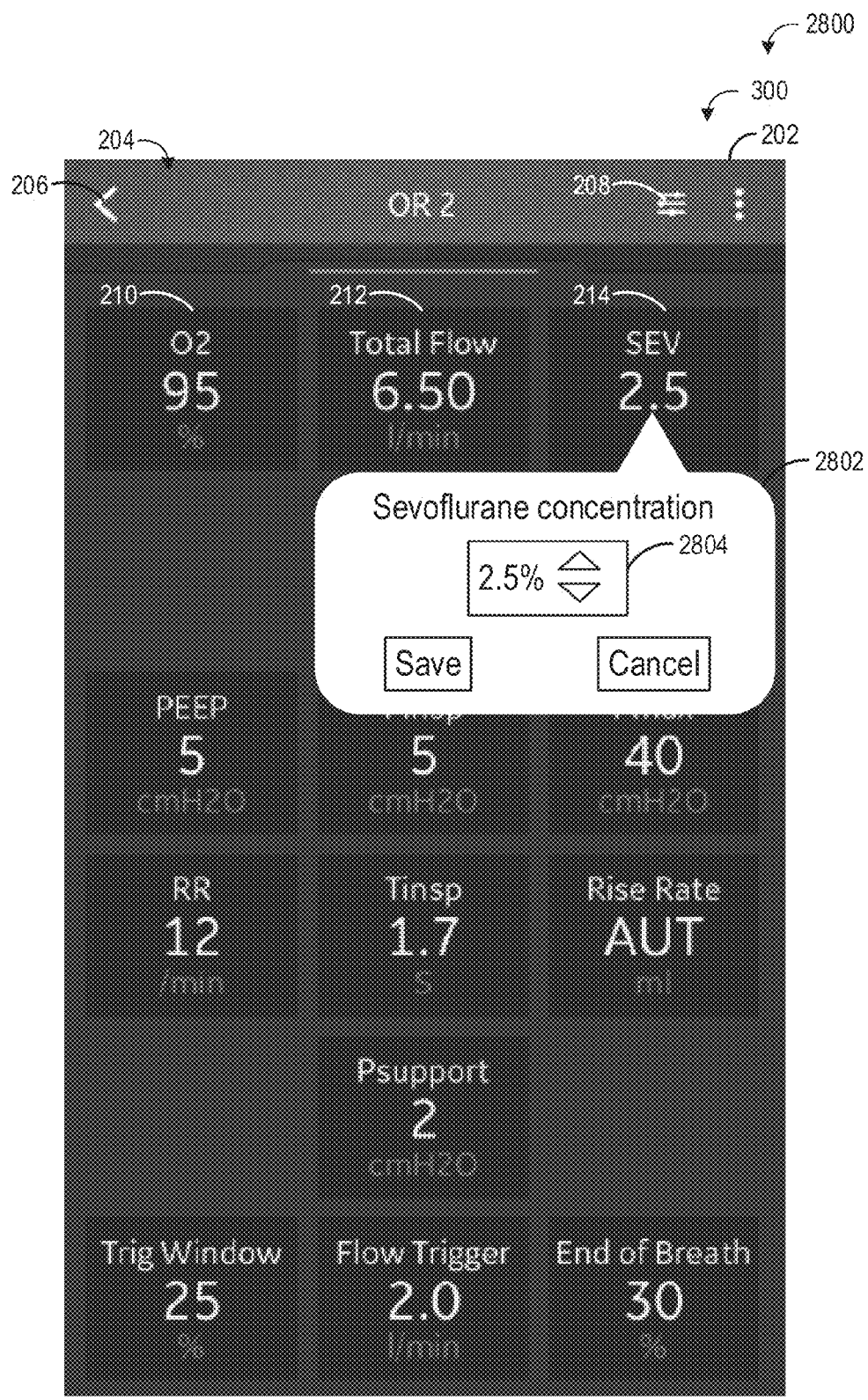

As explained previously, the patient monitoring parameters that may be displayed via the single-patient GUI may include physiological parameters such as measured or inferred heart rate, blood pressure, temperature, and so forth. The patient monitoring parameters may further include, at least in some examples, machine settings for one or more therapy devices being used to carry out a procedure on the patient (or being used in support of the procedure being carried out on the patient), such as settings for an anesthesia delivery machine. The settings may include anesthetic agent concentration, medical gas flow rate, ventilator settings, and so forth. While viewing these settings may be helpful for a user who is located in a different location than the patient (e.g., attending to another patient), the supervisory application may also allow for the user to directly adjust one or more machine settings remotely, without having to actually be in the room where the therapy device is located. Accordingly, as indicated at 2415, a command to adjust one or more machine parameters may be sent to the edge device and/or MDD processing system, when requested. FIG. 28 shows a non-limiting example of how a user may command a change to a machine parameter via the single-patient GUI. FIG. 28 shows an adjustment view 2800 of the single-patient GUI 200 of FIG. 2, which includes the third tile 214 displaying anesthetic agent type and concentration. User selection of the third tile 214 may cause an adjustment box 2802 to be displayed. The adjustment box 2802 may include the selected machine parameter (e.g., sevoflurane concentration) and an adjustment mechanism 2804, which herein includes an up arrow and a down arrow. User input to the adjustment mechanism may cause the sevoflurane concentration to increase or decrease, which may be reflected in the sevoflurane concentration displayed in the adjustment box 2802. Once the user has adjusted the concentration to a desired concentration, the user may save the adjusted concentration by selecting a save button, for example, or may exit the adjustment box 2802 without adjusting the concentration by selecting a cancel button, for example. If the user has adjusted the concentration and selected the save button, the supervisory application may generate and send a command to the edge device and/or MDD processing system to adjust the sevoflurane concentration to the commanded concentration. The therapy device (e.g., anesthesia delivery machine) may then receive the command and automatically change the sevoflurane concentration.

Returning to FIG. 24, the method may include, at 2416, outputting a trends GUI for display when requested. The trends GUI may include trends in selected patient monitoring parameters over time. FIG. 6 shows an example trends GUI, where each trend is visualized as a trend line over the same time duration (e.g., 10 minutes, 30 minutes, or the entire case). The trends GUI may be displayed in response to user selection of a trends button of a single-patient GUI context menu, such as trends button 502 of menu 500. In other examples, the trends GUI may be displayed in response to user selection of a trends icon displayed on the single-patient GUI, such as trends icon 474 of FIG. 4D. The time range of the patient monitoring parameter values displayed in the trends GUI may be adjusted when requested, as indicated at 2418. For example, the trends GUI may include a plurality of buttons each corresponding to a different time range, and user selection of one of the buttons may cause the time range of the displayed trends to change. Further, as also indicated at 2418, the trends GUI may show a quantified change in patient monitoring/medical device data over a specified time period when requested. The quantified change may include an overall percent change between two specified time points, as shown in FIG. 7, which may be requested in response to user input (e.g., a concurrent two touch input to the trends GUI). The trends of the patient monitoring parameters presented via the trends GUI may be adjusted when requested, as indicated at 2420. For example, the trends GUI may include an edit button, such as edit button 608, that causes a trend edit page to be displayed. Via the trend edit page, patient monitoring parameters may be added or removed from the trends GUI. Further, the relative location of each trend on the trends GUI (e.g., the order in which the trends are presented) may be adjusted via the trend edit page.

At 2422, an insights GUI may be output for display when requested. The insights GUI may present insights, which are similar to threshold-based alarms but may be based on more parameters, have limitations on when the insights are applied, and other factors that may make the insights more nuanced and less binary than threshold-based alarms. The insights GUI may be output for display in response to a user request, such as a user selection of an insight engine button from a context menu (e.g., selection of insights engine button 1204 of menu 1200) or other suitable user input. As indicated at 2424, outputting the insights GUI may include displaying a searchable page(s) of local and/or global insights, generated by other users, when requested. FIG. 17 shows an example of a searchable page of the insights GUI, where insights generated by other users at the medical facility where the user is employed (e.g., the local insights) may be displayed, browsed, and/or searched, and where insights generated by other users at other medical facilities (e.g., the global insights) may be displayed, browsed, and/or searched. The user may select one or more insights to be applied to the user's patients/rooms. As indicated at 2426, outputting the insights GUI may include creating, saving, and/or sharing insights when requested. For example, FIG. 19 shows a "my insights" view of the insights GUI where the user may view all insights saved and/or created by the user. When an insight is selected, an insight edit page may be displayed, where the user may turn on or off an insight or edit the rules for the insight. A user may create an insight, such as via the new insights view shown in FIG. 29. Further, an insight may be shared in response to user request (e.g., via selection of a share insight button, such as button 2010 of FIG. 20). When an insight is shared, the privacy setting of the insight may be adjusted to allow other users to view and apply the insight. This may include the insight being sent to another device and/or the cloud, where other users may access the insight. Method 2400 then returns.

Figure 25:
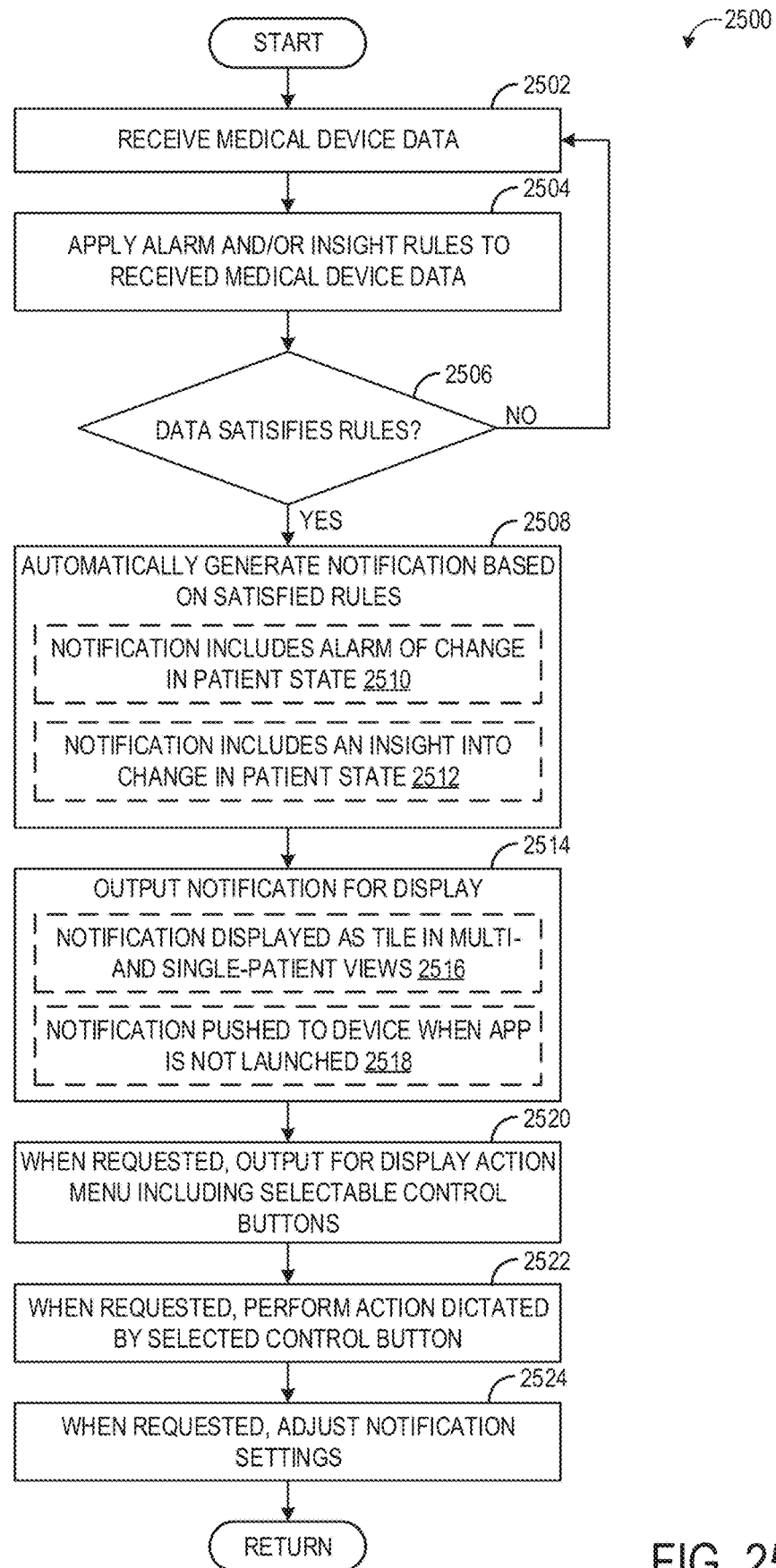
FIG. 25 is a flow chart illustrating an example method for generating and outputting notifications via the supervisory application.

FIG. 25 is a flow chart illustrating an example method 2500 for generating and outputting notifications via the supervisory application. The notifications that are output via the method 2500 of FIG. 25 may be output on a display device associated with a care provider device. Method 2400 may be implemented by a care provider device (such as care provider device 134) in combination with an edge device connected to the care provider device (e.g., edge device 20), a cloud in communication with the edge device and/or care provider device (e.g., MDD processing system 12), or any appropriate combination thereof.

At 2502, medical device data is received. The medical device data may be received from one or more medical devices, such as the medical devices 16 of FIG. 1A. The medical device data may be received by a data ingestion module of the edge device, for example, and in some examples may be processed by a stream processing module of the edge device, as explained above with respect to FIG. 1B. At 2504, alarm and/or insight rules are applied to the received medical device data. For example, the medical device data that is received may be supplied to a rules engine and/or an inference engine of the edge device, which may apply insight rules in order to determine if the received medical device data satisfies any of the saved insight rules. The insight rules may include a plurality of sets of insight rules with each set of insight rules including a condition and a scope of the condition. For example, the condition may include a specified patient monitoring parameter and a condition relative to a threshold for that patient monitoring parameter (e.g., heart rate being greater than 150 beats per minute) and the scope may include a duration of the condition and/or procedure phase in which the condition is to occur in order to trigger the insight, such as for five minutes and/or during maintenance phase of anesthesia delivery.

Each set of alarm rules and each set of insight rules may also include an indication of which patient(s) the rules are applicable to and may also include an indication of which user(s) of the supervisory application should receive a notification if the alarm rules or insight rules are satisfied.

The alarm rules may include a plurality of sets of alarm rules, with each set of alarm rules including a specified patient monitoring parameter (e.g., heart rate) meeting a condition relative to a threshold (e.g., being greater than 150 beats per minute). In some examples, the alarms described herein may be generated by individual medical devices and sent to the edge device, which then outputs the alarm to the appropriate care provider device (as explained below). In such cases, the only alarm rules that may be applied by the supervisory application may include whether a user has chosen to receive a particular alarm or has chosen to not be notified of a particular alarm.

At 2506, method 2500 includes determining if the received medical device data satisfies the alarm rules and/or the insight rules, such that an alarm or an insight is triggered. For example, if medical device data specific to a first patient indicates that the heart rate of the patient is greater than 150 beats per minute, and if the rules engine includes a set of alarm rules indicating that an alarm should be output if the first patient's heart rate is greater than 150 beats per minute, then the medical device data satisfies that set of alarm rules. If no alarm or insight rules have been triggered, method 2500 loops back to 2502 and continues to receive medical device data and apply the alarm and/or insight rules to the received data.

If the received medical device data satisfies at least one set of alarm rules or one set of insight rules, method 2500 proceeds to 2508 to automatically generate a notification based on the satisfied rules. Generating the notification may include, as indicated at 2510, generating a notification that includes an alarm of a change in patient state. If a set of alarm rules is satisfied, an alarm may be generated. The alarm may include an indication of which alarm rules were satisfied, the patient the alarm is for, the user(s) who should receive the alarm, and/or the time the alarm was triggered. Further, generating the notification may include, as indicated at 2512, generating a notification that includes an insight into a change in patient state. If a set of insight rules is satisfied, an insight notification may be generated. The insight notification may include an indication of which insight rules were satisfied, the patient the insight is specific to, the user(s) who should receive the insight notification, and/or the time the insight was triggered. In some examples, the insight notification may include processed data, a prediction of future patient state, a determination of current patient state or procedure phase, or other non-alert result. In such examples, the result of the insight may be displayed as a tile on a single-patient GUI and/or multi-patient GUI during all conditions.

At 2514, the notification is output for display. In some examples, the notification may be generated by the edge device and sent to the appropriate care provider device directly (e.g., via a hospital network communicatively coupling the edge device and the care provider device) or indirectly (e.g., via cloud-based service). When the care provider device receives the notification, the care provider device may display the notification as a tile in a multi-patient GUI and/or a single-patient GUI, as indicated at 2516. For example, as shown in FIG. 9, a brief notification of an alarm may be displayed in an alarm tile (e.g., tile 306) and a more detailed notification of the alarm may be displayed when requested by the user (e.g., as the alarm banner 904). In some examples, as indicated at 2518, the notification is pushed to the care provider device (e.g., via the cloud-based service), even when the supervisory application is in an unlaunched state on the care provider device. In such an example, when the supervisory application is not launched on the care provider device, the care provider device may output the notification for display on a notification page, a home page, and/or a sleep page of the care provider device.

At 2520, an action menu including selectable control buttons may be output for display when requested. The action menu may be displayed when an alarm or insight tile of a multi-patient or single-patient GUI is selected, such as the acknowledge button 806 and snooze button 808 of FIG. 8 that are displayed in response to user selection of the insights tile 302. At 2522, an action dictated by the selected control button may be performed when requested. For example, if the user selects the snooze button, the notification of the triggered alarm or insight may be output again after a predetermined amount of time, such as 10 minutes.

At 2524, the notification settings for a specific user (and hence the user's care provider device) may be adjusted when requested. For example, if a settings button is selected (e.g., button 906 of FIG. 9), an alarms setting page may be displayed where saved alarms may be turned on, turned off, or removed, and where new alarms may be added. In another example, via input to a displayed insight in a "my insights" view of an insights GUI of the supervisory application, an edit insight page may be displayed (e.g., as shown in FIG. 20) where saved insights may be turned on, turned off, edited, or deleted, and where new insights may be created. In a still further example, insights created by other users may be searched or browsed via a "discovery" view of the insights GUI (as shown in FIG. 17), and any selected insights from the discovery view may be saved to be applied for that user. Method 2500 then returns.

Figure 26:
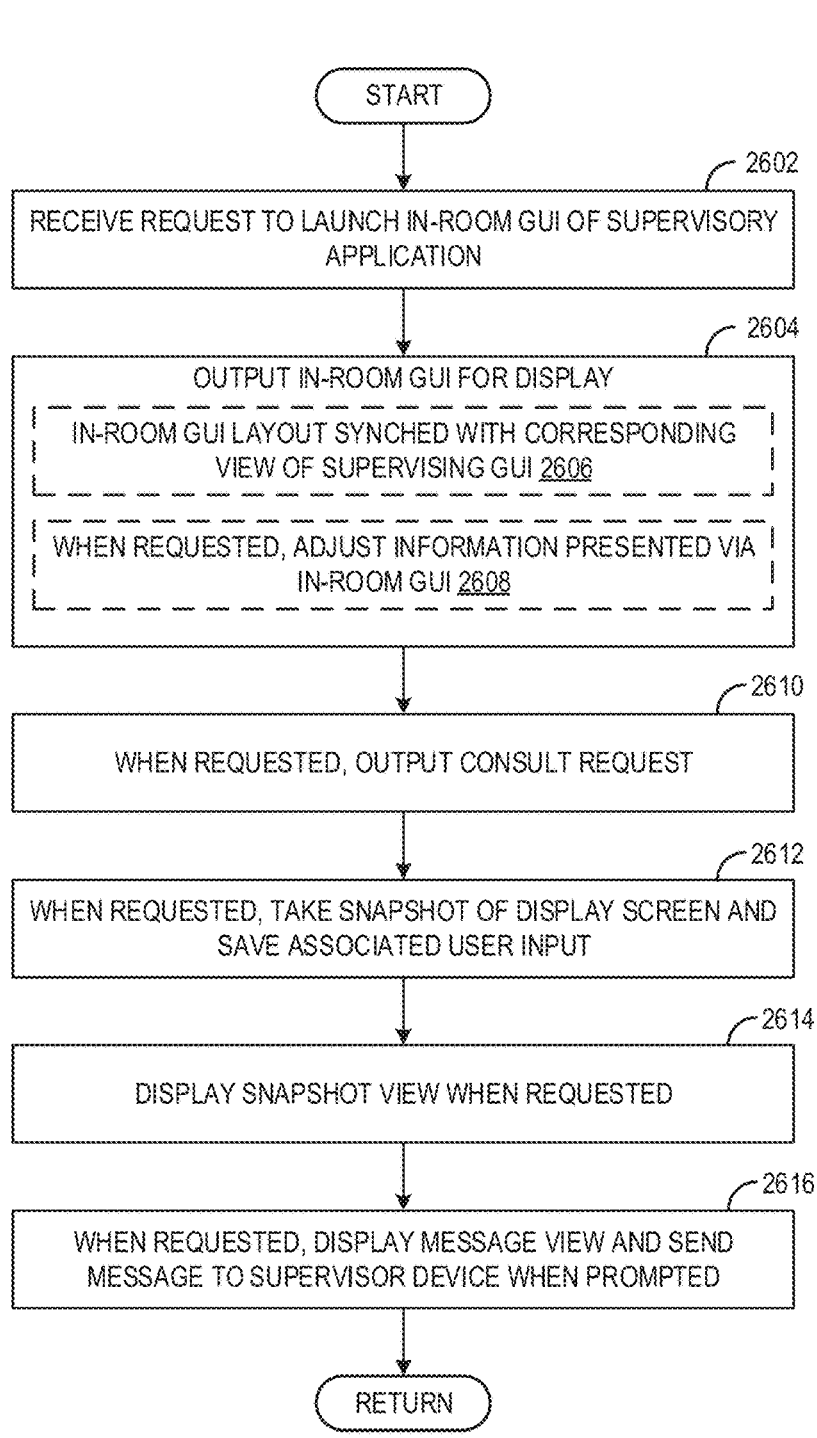
FIG. 26 is a flow chart illustrating an example method for displaying in-room graphical user interfaces generated via the supervisory application.

FIG. 26 is a flow chart illustrating an example method 2600 for displaying in-room graphical user interfaces generated via the supervisory application on a display device associated with a care provider device. Method 2600 may be implemented by a care provider device (such as care provider device 136) being used by a subordinate care provider in combination with an edge device connected to the care provider device (e.g., edge device 20), a cloud in communication with the edge device and/or care provider device (e.g., MDD processing system 12), or any appropriate combination thereof.

At 2602, a request to launch an in-room GUI of the supervisory application is received. The request to launch the in-room GUI of the supervisory application may be received via user input, such as a user of the care provider device selecting a supervisory application icon displayed on a home page or other location of the display device associated with the care provider device. Upon the request to launch the in-room GUI of the supervisory application being received, an in-room GUI is output for display on the display device, as indicated at 2604. FIG. 21 shows an example of an in-room GUI.

In some examples, prior to displaying the in-room GUI and after the request to launch the in-room GUI is received, an authentication/log-in page may be displayed, via which the user may enter log-in information via text input, via a captured image (e.g., facial recognition), via a fingerprint, or other suitable mechanism for entering credentials for authentication. Once the user is authenticated, the in-room GUI may be launched. The in-room GUI may be displayed in response to determining that the user requesting to launch the supervisory application is a subordinate care provider, or a care provider that is otherwise overseeing only a single patient at a time and/or is intended to be located in a single room over the course of a patient procedure. Further, in some examples, the edge device may include a registry component that dynamically maintains the location (room, unit, department) and patient association for each streaming device data session (e.g., each time a care provider device launches the supervisory application). The supervisory application may determine, via the registry, which care providers are in which rooms, and launch the appropriate in-room GUI based on the location of the care provider devices. The care providers are assigned to a department/unit. The user of the supervisory application will know which patient is currently in the given operating room, and hence is able to associate a given patient to the streaming data provided by the operating room, at any given point of time.

Outputting the in-room GUI for display may include outputting an in-room GUI having a layout that is synched with the layout of the corresponding supervising GUI, as indicated at 2606. For example, the in-room GUI may be displayed on a display device of a care provider device that is being used by/associated with a subordinate care provider that is being overseen by a supervising care provider, where the subordinate care provider and supervising care provider are each attending to the same patient. The supervising care provider may select/customize a layout for a single-patient GUI for the patient, as explained above with respect to FIGS. 2, 4A, and 24, for example. The layout of the in-room GUI for the patient may match the layout of the single-patient GUI, at least with respect to the patient monitoring parameters that are displayed. In some examples, the user of the in-room GUI may not be able to adjust the layout of the in-room GUI, and may not be able to adjust which patient monitoring parameters are displayed via the in-room GUI. By synching the view of the in-room GUI with that of the corresponding single-patient GUI, the supervising care provider and subordinate care provider may view the same information in the same format, which may ensure that the care providers are able to properly coordinate care of the patient and may prevent errors or miscommunication due to the care providers viewing different patient monitoring parameters. However, in other examples, the information presented via the in-room GUI may be adjusted when requested, as indicated at 2608, such as via an edit function of the in-room GUI.

At 2610, a consult request may be output when requested. The consult request may be a quick, one-input mechanism for the subordinate care provider to request that the supervising care provider come to the room where the subordinate care provider is attending to the patient. The consult request may be requested by user selection of a call button, such as call button 2106 of FIG. 21. When a consult is requested, a notification may be output to the supervising care provider's device and displayed as a notification in a message tile of the single-patient GUI for the patient or a multi-patient GUI and/or pushed to the supervising care provider's device, similar to the way in which an alarm or insight notification is delivered to a care provider device.

At 2612, a snapshot of the display screen may be taken and any associated user input may be saved with the snapshot, when requested. A snapshot may include an image of what is displayed on the display device at the time the snapshot request is received, which may include the current values for the patient monitoring parameters being presented via the in-room GUI. The snapshot may be taken in response to user selection of a snapshot button on the in-room GUI, such as the snapshot button 2108 of FIG. 21. The snapshot may be saved in a snapshot view of the in-room GUI, such as the snapshot view 2300 of FIG. 23. The snapshot may be saved with relevant patient information, such as procedure phase and timing, number of triggered alarms, etc., as well as information input by the user of the in-room GUI. The snapshot view may be displayed when requested, as indicated at 2614, such as in response to user selection of a snapshot view button of the in-room GUI (e.g., button 2120 of FIG. 21).

At 2616, a message view may be displayed when requested, such as the message view 2200 shown in FIG. 22. The message view may be displayed in response to user selection of a message view button of the in-room GUI, such as button 2118. In the message view, a message thread between the user of the in-room GUI (e.g., the subordinate care provider) and the supervising care provider may be displayed. Further, as indicated at 2616, a message may be sent to the supervising care provider's device when prompted. For example, the user of the in-room GUI may enter text or voice input that may be formatted into a text message and sent to the supervising care provider's device. The user may also send rich-media based messages, such as a snapshot. When the message is received at the supervising care provider's device, the single-patient GUI or multi-patient GUI may include an indication of the received message in a message tile (e.g., tile 304) and when the supervising care provider selects the message tile, the message thread, including the received message, may be displayed on the supervising care provider's device (e.g., as shown in FIG. 9). Further, similar to the alarm and insight notifications, the message notification may be pushed to the supervising care provider's device even when the supervisory application on the supervising care provider's device is in an unlaunched state. Method 2600 then returns.

Figure 27:
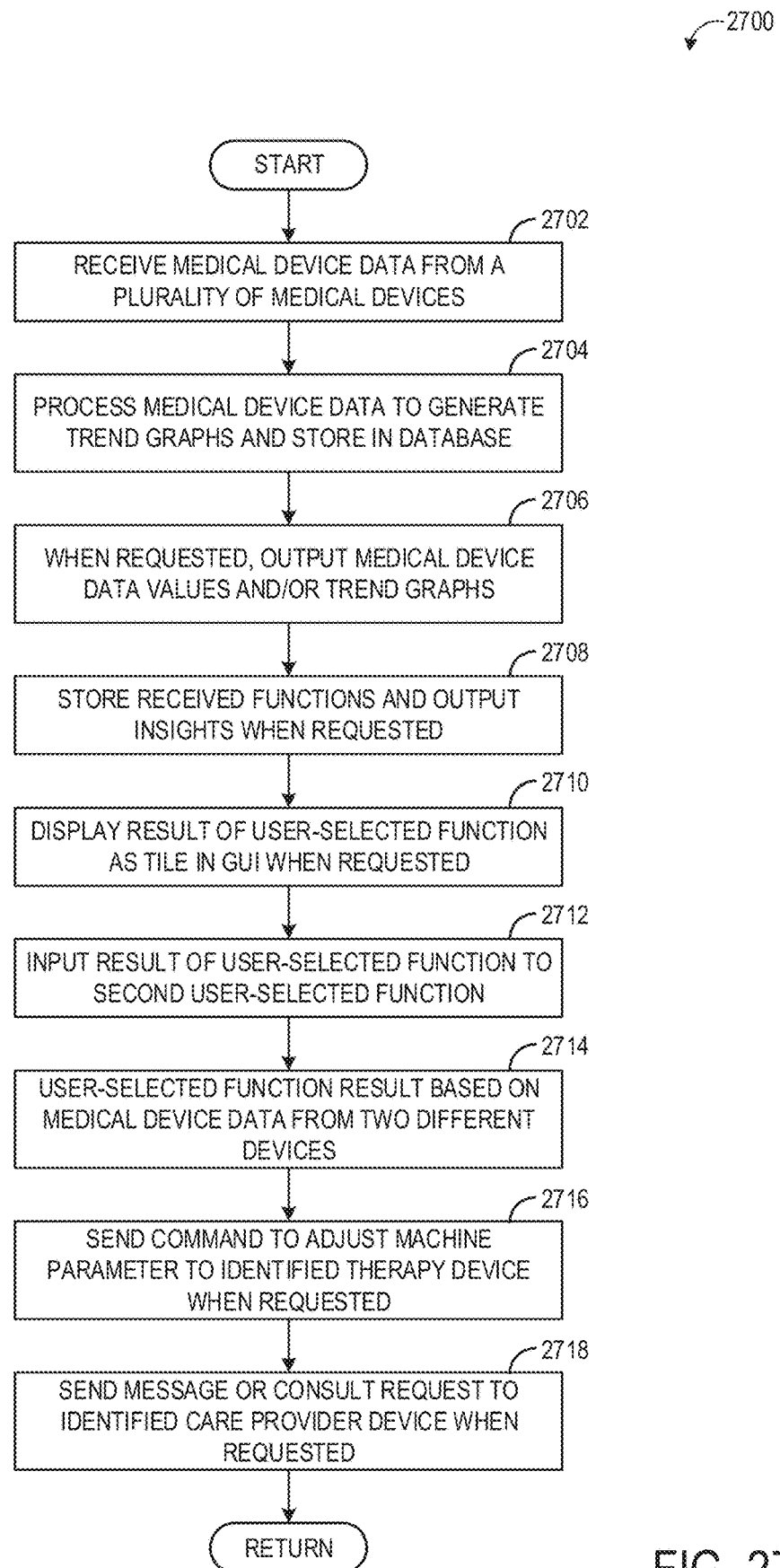
FIG. 27 is a flow chart illustrating an example method for a supervisory application.

FIG. 27 is a flow chart illustrating an example method 2700 for a supervisory application. Method 2700 may be implemented by an edge device connected to the care provider device (e.g., edge device 20), a cloud in communication with the edge device and/or care provider device (e.g., MDD processing system 12), a care provider device (such as care provider device 134), or any appropriate combination thereof.

At 2702, medical device data from a plurality of medical devices is received. The medical device data may be received from one or more medical devices, such as the medical devices 16 of FIG. 1A. The medical device data may be received by a data ingestion module of the edge device, for example, and in some examples may be processed by a stream processing module of the edge device, as explained above with respect to FIG. 1B. Additionally or alternatively, the medical device data may be sent to a cloud-based device, such as the MDD processing system 12 of FIG. 1A, where the medical device data may be ingested by an ingestion module (e.g., high speed ingestion module 22).

At 2704, the medical device data may be processed to generate trend graphs and the trend graphs are stored in a database. For example, each stream of medical device data may be stored, at least temporarily, as a trend graph (which may be a line graph, a series of bar graphs, or another suitable representation of data values over time) in a data storage location, such as data storage 104 of FIG. 1B and/or operation case storage 30 of FIG. 1A.

At 2706, medical device data values and/or trend graphs are output when requested. For example, when a supervisory application (such as supervisory application 44) is launched on a care provider device (such as care provider device 134), a single-patient GUI (e.g., single patient GUI 200 of FIG. 2), a multi-patient GUI (e.g. multi-patient GUI 1100 of FIG. 11 or multi-patient GUI 1300 of FIG. 13), or an in-room GUI (such as in-room GUI 2100 of FIG. 21) may be displayed on a display of the care provider device. When one of these GUIs is displayed, the supervisory application may stream real-time medical device data values to the care provider device, via a streaming server such as streaming server 114 of FIG. 1B. In another example, a trends GUI may be displayed on the display of the care provider device, and selected assembled/stored trend graphs may be output to the care provider device to be displayed as part of the trends GUI. In a still further example, when the single-patient GUI is displayed on the display of the care provider device, user selection of a patient monitoring parameter tile may cause display of a trend graph for that patient monitoring parameter and/or additional trend graphs of related patient monitoring parameters, and the selected assembled/stored trend graphs may be output to the care provider device to be displayed as part of the single-patient GUI.

At 2708, received functions are stored and selected stored functions are output when requested. The received functions may be received from the care provider device, for example in response to user-creation of a function (e.g., an insight) via an insights GUI (e.g., insights GUI 1700) displayed on the display of the care provider device. Functions may be created via other mechanisms, and may include models, algorithms, or other routines to process the medical device data from one or more medical devices and produce a result based on the medical device data. Functions may be received by other care provider devices at one or more medical facilities. The received functions may be stored at the edge device and/or on the MDD processing system. Further, when a user creates a function, that function may be shared with other users in response to a request from the user. Thus, if a request to share a function is received, that function may be output to a different storage location (e.g., the rules defining the insight may be sent from the edge device to the MDD processing system or other cloud-based service). In other examples, such as when all functions are stored on the cloud, the function may not be output to a different location when shared, but the privacy setting of the function may be changed to allow the function to be shared with other users.

At 2710, the result of a user-selected function is displayed as a tile in a GUI, such as a single-patient GUI, when requested. For example, a user may select to apply a function for a specific patient or room, such as by selecting a function created by another user via the insights GUI 1700 or by selecting to apply a function created by the user, for example by generating a function via the new insights view 2900 and selecting to apply that function. The user-selected function may produce a transient result, such as a notification that is only triggered when a condition and a scope of the condition are met by the medical device data for the patient. As another example, the user-selected function may produce a persistent result that may generated under some or all of the duration of the patient monitoring for the patient, such as a determination of the anesthesia phase or an indication of a determined current patient state, such as a sepsis risk. In the example of the function that produces a sepsis risk result, the sepsis risk result may be on a scale of 1-10, classified as low, medium, or high, or another representation of the risk, and the representation of the risk may be determined and output at any time over the course of the patient monitoring. If the function produces a transient result, the result of the function may be displayed as a tile (e.g., as an insights tile) in a single-patient GUI specific to the patient or room and/or in a multi-patient GUI only in response to the rules of the function (e.g., the condition/scope) being met. If the function produces a persistent result, the result from the function may be displayed as a tile in the single-patient GUI for the patient in response to a user request to display the tile, and may only be removed from the GUI in response to a user request to remove the tile.

At 2712, the result of a user-selected function is input into a second user-selected function, when requested. As explained above, some functions may include the output of another function as an input, along with the medical device data. If a second user-selected function includes the result of a first user-selected function as an input, the result of the first user-selected function may be determined and then supplied to the second user-selected function. For example, a first function may produce current anesthesia phase as a result and a second function may include a notification being output as a result when heart rate is greater than a threshold during maintenance phase of anesthesia. The result of the first function may be used by the second function to determine the result of the second function along with the received medical device data (e.g., the anesthesia phase may be analyzed along with the heart rate as determined from a medical device monitoring a patient to determine if a notification should be output). As another example, a first function may produce sepsis risk as a result and a second function may include a notification being output as a result when heart rate is greater than a first threshold and when sepsis risk is greater than a second threshold. The result of the first function may be used by the second function to determine the result of the second function along with the received medical device data (e.g., the sepsis risk as determined by the first function may be analyzed along with the heart rate as determined from a medical device monitoring a patient to determine if a notification should be output).

At 2714, in some examples, the result of a user-selected function is based on medical device data from at least two different medical devices, and the respective patient monitoring values or trends from each of the two different medical devices may be displayed as respective tiles on a single-patient GUI, and in some examples, the result of the user-selected function is displayed as a separate tile on the single-patient GUI. For example, a function that produces a sepsis risk value (e.g., on a scale of 1-10) may determine the sepsis risk value based on, among other parameters, heart rate and body temperature. Heart rate may be determined from first medical device data output by a first medical device (e.g., a heart rate monitor) and body temperature may be determined from second medical device data output by a second medical device (e.g., a temperature sensor). The heart rate may be displayed in a first patient monitoring parameter tile on a single-patient GUI, the body temperature may be displayed in a second patient monitoring parameter tile on the single-patient GUI, and the sepsis risk may be displayed as a third tile on the single-patient GUI.

As another example, a function that produces a notification when a change in heart rate over a specified duration is above a threshold change and when body temperature is above threshold temperature may include as input into the function heart rate as determined from first medical device data output by a first medical device (e.g., a heart rate monitor) and body temperature as determined from second medical device data output by a second medical device (e.g., a temperature sensor). The heart rate may be displayed in a first patient monitoring parameter tile on a single-patient GUI, the body temperature may be displayed in a second patient monitoring parameter tile on the single-patient GUI, and the notification output as a result of the function may be displayed as a third tile on the single-patient GUI, at least when the specified conditions trigger the notification. In this way, user-selected functions may utilize medical device data, which may include medical device data from two or more devices in some examples, and may also use the results of other functions to provide insights into current or future patient state that may not be possible by monitoring the output of individual medical devices in isolation. For example, a heart rate monitor may be configured to output an alarm when heart rate is very high, such as greater than 150 beats per minute. While such an alarm may be useful, the alarm may miss earlier or more subtle signs that the patient may be undergoing duress. Thus, a function that combines a change in heart rate with body temperature may be able to provide an earlier potential warning of sepsis or other deterioration in patient state than by relying solely on heart rate reaching a predefined threshold. If the patient has a low resting heart rate, for example, the relative change in heart rate may be more informative than the absolute number of beats per minute, and by combining the change in heart rate with body temperature, the change in heart rate may be put into better context and thus provide different information to a care provider than if heart rate changed while body temperature remained stable.

At 2716, a command to adjust a machine parameter is sent to an identified therapy device if requested. For example, a determination may be made if a request to change a machine parameter has been received. As explained above with respect to FIG. 24, a user of the supervisory application (e.g., the supervising care provider interacting with the supervising application on a care provider device) may request a machine parameter or setting be adjusted via an adjustment box displayed as part of the single-patient GUI. The care provider device may send a request to the edge device to adjust the machine parameter. The therapy device may be identified based on the received request from the care provider device, which may specify which machine (e.g., therapy device) is to be adjusted and which parameter of the machine is to be adjusted (and by how much).

At 2718, a message or consult request is sent to an identified care provider device if requested. For example, a message or consult request may be received from a first care provider device (e.g., from a device being used by a subordinate care provider, such as care provider device 136) that is displaying the in-room GUI. If a message or consult request has been received, the message or consult request may be sent to an identified care provider device. The recipient care provider device may be identified in the message or consult request sent by the care provider device, and the identified care provider device may be a second, different care provider device, such a care provider device being used by a supervising care provider (e.g., care provider device 134). Method 2700 then returns.

In another representation, a system includes a display and a computing device operably coupled to the display and storing instructions executable to: output, to the display, a graphical user interface (GUI) that includes real-time medical device data collected by a plurality of medical devices each monitoring a patient and also includes one or more machine parameters for one or more therapy devices being utilized in a medical procedure performed on the patient; responsive to a user input, output, to the display, an action menu including one or more control buttons selectable to adjust a selected machine parameter of the one or more machine parameters; and responsive to user selection of one or more of the one or more control buttons, send a request to adjust the selected machine parameter to a therapy device associated with the selected machine parameter, the request sent via an intermediate processing system.

In another representation, a system includes a display and a computing device operably coupled to the display and storing instructions executable to output, on the display, a user interface that presents to a user medical device data aggregated from multiple medical devices, the user interface also configured to present to the user available parameters that are based on the medical device data and available operators, and the user interface is configured to receive user input specifying a user-defined relationship for display in a tile of the user interface, the user-defined relationship using selected ones of the available operators and the available parameters.

In another representation, a system includes a display and a computing device operably coupled to the display and storing instructions executable to output, on the display, a user interface that presents to a user medical device data aggregated from multiple medical devices, the user interface configured to present to medical device data as a plurality of patient monitoring parameter tiles, and where the user interface is configurable by the user and presents a plurality of user-selectable display formats for medical device data in the plurality of patient monitoring parameter tiles. In an example, the plurality of user-selectable display formats includes a first display format where the medical device data is presented as a most-recently determined value, a second display format where the medical device data is presented as a trend of values over a specified time duration, a third display format where the medical device data is presented as a waveform, a fourth display format where multiple related parameters of the medical device data are displayed in a single tile, and combinations thereof. The multiple related parameters of the medical device data that may be displayed in a single tile include systolic and diastolic blood pressure displayed in a single tile and end tidal (Et) oxygen content and fraction of inspired air (Fi) oxygen content in a single tile.

A technical effect of a supervisory application that displays medical device data aggregated from multiple medical devices on a single graphical user interface in a user-configurable manner is that a user, such as a care provider, may view desired patient monitoring parameters for a patient the user is monitoring on a limited display area, with as much data as possible displayed on the limited display area. The displaying of the medical device data from multiple medical devices on the single graphical user interface in a user-configurable manner also allows the user to monitor patient status from any location and provide instructions via the supervisory application. The user may view new medical device data as new medical devices are coupled to the patient. The user may define functions and/or access functions defined by other users via the supervisory application that may transform and/or analyze the medical device data (from multiple medical devices) to provide results of patient status not detectable from single values of the medical device data. The functions may be created and accessed at any time, which may allow new functions to be defined and applied as new devices are added. Via the supervisory application, the user may locate and view desired data without having to navigate through multiple menus, which may increase user efficiency in interacting with a computing device.

In an embodiment, a system includes a display; and a computing device operably coupled to the display and storing instructions executable to: output, to the display, a graphical user interface (GUI) that includes a plurality of trend lines each showing values for a respective patient monitoring parameter over a first time range, the plurality of trend lines time-aligned and vertically stacked relative to each other; responsive to a first user input, adjust each of the plurality of trend lines to show values for the respective patient monitoring parameter over a second time range; and responsive to a second user input, display, on the GUI, an overlay that shows a relative change in each patient monitoring parameter over a specified time duration. In a first example of the system, the GUI is a trends GUI, and wherein the instructions are executable to output, to the display, a single-patient GUI in response to a user request, the single-patient GUI including real-time medical device data determined from output of one or more medical devices each monitoring a patient, and where at least some of the real-time medical device data displayed via the single-patient GUI is displayed as a plurality of patient monitoring parameter tiles, each patient monitoring parameter tile showing a most-recently determined value for that patient monitoring parameter, and wherein the values for each respective patient monitoring parameter for the plurality of trend lines are determined from the output of the one or more medical devices. In a second example of the system, which optionally includes the first example, the instructions are executable to output, to the display, a set of trends within the single-patient GUI in response to user selection of a first patient monitoring parameter tile, wherein the set of trends includes a first trend line showing values for the first patient monitoring parameter over the first or second time range, the values for the first patient monitoring parameter determined from the output from the one or more medical devices. In a third example of the system, which optionally includes one or both of the first and second examples, the set of trends further includes a trends icon, and wherein the instructions are executable to output the trends GUI to the display in response to user selection of the trends icon. In a fourth example of the system, which optionally includes one or more or each of the first through third examples, the instructions are executable to output the trends GUI to the display in response to user selection of a trends button of a context menu, the context menu output to the display in response to user selection of a menu button displayed on the display as part of the single-patient GUI. In a fifth example of the system, which optionally includes one or more or each of the first through fourth examples, the instructions are executable to output a multi-patient GUI including real-time medical device data determined from output of a plurality of medical devices monitoring a plurality of patients, the plurality of patients including the patient and one or more additional patients, and wherein the instructions are executable to output the single-patient GUI in response to user selection of a representation of the patient in the multi-patient GUI. In a sixth example of the system, which optionally includes one or more or each of the first through fifth examples, the first time range is different than the second time range, and wherein the specified time range is specified by a user.

In an embodiment, a method includes outputting, to a display, a first graphical user interface (GUI) that includes real-time medical device data determined from output of one or more medical devices each monitoring a patient, and where at least some of the real-time medical device data displayed via the first GUI is displayed as a plurality of patient monitoring parameter tiles, each patient monitoring parameter tile showing a most-recently determined value for that patient monitoring parameter; and responsive to a user request, outputting, to a display, a second GUI that includes a plurality of trend lines each showing values for a respective patient monitoring parameter over a first time range, the plurality of trend lines time-aligned and vertically stacked relative to each other. In a first example of the method, outputting the second GUI responsive to the user request includes outputting the second GUI responsive to user selection of a trends icon displayed as part of the first GUI or responsive to user selection of a trends button of a context menu that is configured to be displayed in response to user selection of a menu button of the first GUI. In a second example of the method, which optionally includes the first example, the first GUI further includes an alarm tile and an insights tile, the alarm tile including an indication of a number of alarms that have been triggered for the patient and the insights tile including an indication of a number of insights that have been triggered for the patient. In a third example of the method, which optionally includes one or both of the first and second examples, the method further includes receiving an alarm for the patient in response to a value of a specified patient monitoring parameter determined from a medical device meeting a predetermined condition relative to a threshold, and in response to user selection of the alarm tile, outputting an alarm banner in the first GUI that indicates the value of the specified patient monitoring parameter has met the predetermined condition relative to the threshold. In a fourth example of the method, which optionally includes one or more or each of the first through third examples, the method further includes triggering an insight for the patient in response to a set of values determined from the output of the one or more medical devices meeting a condition and a scope of the condition, and in response to user selection of the insight tile, outputting an insight banner in the first GUI that indicates the set of values has met the condition and the scope of the condition. In a fifth example of the method, which optionally includes one or more or each of the first through fourth examples, the method further includes adjusting a layout of the first GUI in response to user input, the layout of the first GUI including which patient monitoring parameter tiles are included in the first GUI and/or a visual appearance of each patient monitoring parameter tile of the first GUI. In a sixth example of the method, which optionally includes one or more or each of the first through fifth examples, the one or more medical devices include an anesthesia delivery machine, wherein the output of the medical devices includes physiological data of the patient collected by the anesthesia machine and machine data including settings of the anesthesia delivery machine, and wherein the plurality of trend lines of the second GUI are organized into physiological trends and machine settings trends.

In an embodiment, a system includes a display; and a computing device operably coupled to the display and storing instructions executable to: output, to the display, a graphical user interface (GUI) that includes real-time medical device data determined from output of one or more medical devices each monitoring a patient, and where at least some of the real-time medical device data displayed via the GUI is displayed as a plurality of patient monitoring parameter tiles, each patient monitoring parameter tile showing a most-recently determined value for that patient monitoring parameter; responsive to a user selection of a first patient monitoring parameter tile showing a most-recently determined value for a first patient monitoring parameter, adjust the GUI to include a trend display for the first patient monitoring parameter and also include one or more additional trend displays for related patient monitoring parameters. In a first example of the system, the related patient monitoring parameters are preselected by a user. In a second example of the system, which optionally includes the first example, the trend display for the first patient monitoring parameter and the one or more additional trend displays for the related patient monitoring parameters each include a trend line each showing a change in values for a respective patient monitoring parameter over a time duration. In a third example of the system, which optionally includes one or both of the first and second examples, the instructions are executable to overlay a timeline on the trend display for the first patient monitoring parameter and the one or more additional trend displays for the related patient monitoring parameters, the timeline including a respective value for the first patient monitoring parameter and each related patient monitoring parameter at a time corresponding to a position of the timeline. In a fourth example of the system, which optionally includes one or more or each of the first through third examples, the one or more medical devices include an anesthesia delivery machine, wherein the output of the medical devices includes physiological data of the patient collected by the anesthesia machine and machine data including settings of the anesthesia delivery machine, and wherein the first GUI further includes a procedure timing tile including a current phase of anesthesia delivery to the patient. In a fifth example of the system, which optionally includes one or more or each of the first through fourth examples, the first GUI includes a plurality of categories, and each patient monitoring parameter tile is assigned to a category of the plurality of categories.

In an embodiment, a system includes a computing device storing instructions executable to: receive an insight defined by a user, the insight dictating that a notification be output when a condition and a scope of the condition are met, the condition and the scope defined by the user; receive real-time medical device data determined from output from a plurality of medical devices monitoring a plurality of patients; determine if a set of values of one or more patient monitoring parameters of the medical device data meet the condition and the scope, and if so, output the notification for display on a display operably coupled to a first care provider device associated with the user; and responsive to a request from the user, adjust a privacy setting of the insight to allow the insight to be distributed to one or more additional care provider devices associated with other users. In a first example of the system, the insight is a first insight dictating that a first notification be output when a first condition and a first scope of the first condition are met, and wherein the instructions are further executable to: receive a first request, from the first care provider device, to view a plurality of second insights defined by one or more additional users; in response to receiving the first request, send the plurality of second insights to the first care provider device; receive a second request, from the first care provider device, to apply a selected one of the plurality of second insights, the selected one of the plurality of second insights dictating that a second notification be output when a second condition and a second scope of the second condition are met; and in response to the second request, determine if a second set of values of one or more patient monitoring parameters of the medical device data meet the second condition and the second scope, and if so, output the second notification for display on the display operably coupled to the first care provider device. In a second example of the system, which optionally includes the first example, the condition includes a selected patient monitoring parameter value or trend meeting a predetermined relationship relative to a threshold, and wherein the scope includes a timing- or procedure-based limitation on when the condition being met triggers the notification. In a third example of the system, which optionally includes one or both of the first and second examples, the insight is defined, by the user, as being applicable to only selected one or more patients of the plurality of patients. In a fourth example of the system, which optionally includes one or more or each of the first through third examples, the insight is a first insight dictating that a first notification be output when a first condition and a first scope of the first condition are met, and wherein the instructions are further executable to: receive a request, from the first care provider device, to apply a second insight, the second insight dictating that a second notification be output when a second condition and a second scope of the second condition are met and a third condition and a third scope of the third condition are all met; determine if a second set of values of one or more patient monitoring parameters the medical device data meet the second condition and the second scope and the third condition and the third scope, and if so, output the second notification for display on the display operably coupled to the first care provider device. In a fifth example of the system, which optionally includes one or more or each of the first through fourth examples, the instructions are further executable to: receive a second request, from a second care provider device of the one or more additional care provider devices, to view the insight, and in response, send the insight to the second care provider device. In a sixth example of the system, which optionally includes one or more or each of the first through fifth examples, the instructions are further executable to: receive a third request, from the second care provider device, to apply the insight to one or more patients of the plurality of patients; in response to the third request, determine if a second set of values of one or more patient monitoring parameters of the medical device data meet the condition and the scope, and if so, output the notification for display on a display operably coupled to the second care provider device. In a seventh example of the system, which optionally includes one or more or each of the first through sixth examples, the instructions are further executable to: receive an alarm from one of the plurality of medical devices; determine if the user has selected to receive the alarm; and if the user has selected to receive the alarm, output an indication of the alarm for display on the display operably coupled to the first care provider device. In an eighth example of the system, which optionally includes one or more or each of the first through seventh examples, the alarm indicates that a value of a patient monitoring parameter of medical device data determined from output of the one of the plurality of medical devices has reached a predetermined condition relative to a threshold.

An embodiment of a system includes a display; and a computing device operably coupled to the display and storing instructions executable to: output, to the display, real-time medical device data, the real-time medical device data viewable on the display in a graphical user interface (GUI), the real-time medical device data determined from output of one or more medical devices monitoring one or more patients; output, to the display, a determined result of a first user-selected function, the real-time medical device data entered as input into the first function, the determined result of the first function viewable on the display as a tile of the GUI; and output, to the display, a notification responsive to a second user-selected function being met, the determined result of the first function entered as input into the second function. In a first example of the system, the real-time medical device data is also entered as input into the second function, and wherein one or both of the first function and second function are selected via a second GUI displayed on the display. In a second example of the system, which optionally includes the first example, one or both of the first function and the second function are defined by a user. In a third example of the system, which optionally includes one or both of the first and second examples, the second function is defined by the first function, a second parameter selected by the user from a predefined set of parameters, and an operator selected by the user from a predefined set of operators. In a fourth example of the system, which optionally includes one or more or each of the first through third examples, the one or more medical devices includes an anesthesia delivery machine, wherein the determined result of the first function is a current phase of anesthesia delivery from the anesthesia delivery machine, wherein the predefined set of parameters includes each patient monitoring parameter that is able to be determined from the real-time medical device data, and wherein the predefined set of operators includes one or more of and, or, and while.

In an embodiment, a system includes a first display; and a first computing device operably coupled to the first display and storing instructions executable to: output, to the first display, a first graphical user interface (GUI) that includes real-time medical device data determined from output of one or more medical devices each monitoring a patient; display on the first GUI a notification indicating a request to communicate with a care provider attending to the patient has been received; and responsive to user selection of the notification, display on the first GUI a communication from the care provider, where the communication from the care provider is received via a second GUI displayed on a second display device operably coupled to a second computing device. In a first example of the system, the communication includes one or more of a request for a consultation, a text message, or a snapshot of the second GUI. In a second example of the system, which optionally includes the first example, the first GUI includes a first plurality of patient monitoring parameter tiles each displaying a respective patient monitoring parameter, each respective patient monitoring parameter showing a most-recently determined value and/or trend for that patient monitoring parameter obtained from the real-time medical device data, and wherein the notification is displayed in a notification tile on the first GUI. In a third example of the system, which optionally includes one or both of the first and second examples, the second GUI includes a second plurality of patient monitoring parameter tiles that matches the first plurality of patient monitoring parameter tiles, a call button, and a message view button. In a fourth example of the system, which optionally includes one or more or each of the first through third examples, the communication from the care provider being received via the second GUI includes the first computing device receiving the communication responsive to a selection, by the care provider, of the call button of the second GUI. In a fifth example of the system, which optionally includes one or more or each of the first through fourth examples, the communication from the care provider being received via the second GUI includes the first computing device receiving the communication responsive to a selection, by the care provider, of the message view button of the second GUI, the selection of the message view button causing a message box to be displayed on the second display via which the communication from the care provider is entered.

An embodiment for a system includes a display; and a computing device operably coupled to the display and storing instructions executable to: output, to the display, a graphical user interface (GUI) that includes real-time medical device data determined from output of one or more medical devices each monitoring a patient, and where at least some of the real-time medical device data displayed via the GUI is displayed as a plurality of patient monitoring parameter tiles, each patient monitoring parameter tile showing a most-recently determined value or a trend for that patient monitoring parameter, the plurality of patient monitoring parameter tiles arranged according to a first layout; and responsive to a user action, adjust one or more patient monitoring parameter tiles of the plurality of patient monitoring parameter tiles to form a second layout. In a first example of the system, adjusting the one or more patient monitoring parameter tiles of the plurality of patient monitoring parameter tiles to form the second layout includes moving or resizing the one or more patient monitoring parameter tiles to form the second layout. In a second example of the system, which optionally includes the first example, the user action comprises a request to switch from the first layout to the second layout, the request entered via a context menu displayed on the display. In a third example of the system, which optionally includes one or both of the first and second examples, the user action comprises a request to include a new patient monitoring parameter tile on the GUI or a request to remove one of the plurality of patient monitoring parameter tiles from the GUI. In a fourth example of the system, which optionally includes one or more or each of the first through third examples, the user action comprises a request to view a trend on a selected patient monitoring parameter tile. In a fifth example of the system, which optionally includes one or more or each of the first through fourth examples, adjusting the one or more patient monitoring parameter tiles comprises increasing a size of the selected patient monitoring parameter tile to accommodate the trend, and also adjusting one or more additional patient monitoring parameter tiles to accommodate the increased size of the selected patient monitoring parameter tile. In a sixth example of the system, which optionally includes one or more or each of the first through fifth examples, the user action comprises a request to arrange the plurality of patient monitoring parameters according to one or more categories. In a seventh example of the system, which optionally includes one or more or each of the first through sixth examples, the user action comprises a request to view a result from a user-selected function as a tile on the GUI. In an eighth example of the system, which optionally includes one or more or each of the first through seventh examples, the real-time medical device data is applied as input to the user-selected function. In a ninth example of the system, which optionally includes one or more or each of the first through eighth examples, the GUI is a single-patient GUI, and wherein instructions are executable to output a multi-patient GUI including real-time medical device data determined from output of a plurality of medical devices monitoring a plurality of patients, the plurality of patients including the patient and one or more additional patients, and wherein the instructions are executable to output the single-patient GUI in response to user selection of a representation of the patient in the multi-patient GUI.

An embodiment for a method includes displaying real-time medical device data determined from output of one or more medical devices each monitoring a patient via a plurality of patient monitoring parameter tiles of a graphical user interface (GUI) arranged to form a first layout; receiving a request to apply a user-selected function, the user-selected function configured to generate a result based on the real-time medical device data; in response to the request, displaying the result of the user-selected function in a function tile on the GUI and automatically adjusting one or more patient monitoring parameter tiles of the plurality of patient monitoring parameter tiles to form a second layout. In a first example of the method, automatically adjusting the one or more patient monitoring parameter tiles comprises automatically moving and/or resizing the one or more patient monitoring parameter tiles to accommodate the function tile. In a second example of the method, which optionally includes the first example, the user-selected function is defined by the user and the request to apply the user-selected function is received via input from the user. In a third example of the method, which optionally includes one or both of the first and second examples, the user-selected function is a first function, and wherein receiving the request to apply the first function comprises displaying an indication of the first function and a plurality of additional indications of additional functions and receiving user input from the user requesting to apply the first function, where the first function and the plurality of additional functions are defined by one or more other users. In a fourth example of the method, which optionally includes one or more or each of the first through third examples, the method further includes, responsive to a user action, further adjusting one or more patient monitoring parameter tiles of the plurality of patient monitoring parameter tiles to form a third layout.

An embodiment for a method includes displaying real-time medical device data determined from output of one or more medical devices each monitoring a patient via a plurality of patient monitoring parameter tiles of a graphical user interface (GUI) arranged to form a first layout, including displaying first medical device data determined from output of a first medical device in a first patient monitoring parameter tile and displaying second medical device data determined from output of a second medical device in a second patient monitoring parameter tile; receiving a request to apply a user-selected function, the user-selected function configured to generate a result based on the first medical device data displayed in the first patient monitoring parameter tile and the second medical device data displayed in the second patient monitoring parameter tile; and in response to the request, displaying the result of the user-selected function in a function tile on the GUI and automatically adjusting one or more patient monitoring parameter tiles of the plurality of patient monitoring parameter tiles to form a second layout. In a first example of the method, the result includes one of a determination of current patient status, a prediction of future patient status, and a determination of a current phase a medical procedure being performed on the patient. In a second example of the method, which optionally includes the first example, the method further includes receiving an alarm from the first medical device indicating that a value the first medical device data has reached a predetermined condition relative to a threshold, and in response, displaying a notification of the alarm in an alarm tile of the GUI. In a third example of the method, which optionally includes one or both of the first and second examples, automatically adjusting the one or more patient monitoring parameter tiles comprises automatically moving and/or resizing the one or more patient monitoring parameter tiles to accommodate the function tile. In a fourth example of the method, which optionally includes one or more or each of the first through third examples, the method further includes, responsive to a user action, further adjusting one or more patient monitoring parameter tiles of the plurality of patient monitoring parameter tiles to form a third layout.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
a computing device storing instructions executable to:
receive a first insight defined by a user, the first insight including a first function to be applied to medical device data of one or more patients, the first function including a first condition and a first scope of the first condition, the first condition and the first scope defined by the user;
receive real-time medical device data determined from output from a plurality of medical devices monitoring a plurality of patients;
determine if a first set of values of one or more patient monitoring parameters of the medical device data meet the first condition and the first scope, and if so, output a first notification for display on a display operably coupled to a first care provider device associated with the user;
responsive to a request from the user, adjust a privacy setting of the first insight to allow the first insight to be distributed to one or more additional care provider devices associated with other users, where the first insight is configured to be applied to medical device data of additional patients via the one or more additional care provider devices;
receive a second request, from the first care provider device, to view a plurality of second insights defined by one or more additional users;
in response to receiving the second request, send the plurality of second insights to the first care provider device;
receive a third request, from the first care provider device, to apply a selected one of the plurality of second insights, the selected one of the plurality of second insights including a second function to be applied to medical device data of one or more patients, the second function including a second condition and a second scope of the second condition; and in response to the third request, determine if a second set of values of one or more patient monitoring parameters of the medical device data meet the second condition and the second scope, and if so, output a second notification for display on the display operably coupled to the first care provider device.

2. The system of claim 1, wherein the first condition includes a selected patient monitoring parameter value or trend meeting a predetermined relationship relative to a threshold, and wherein the first scope includes a timing- or procedure-based limitation on when the first condition being met triggers the notification.

3. The system of claim 2, wherein the first insight is defined, by the user, as being applicable to only selected one or more patients of the plurality of patients.

4. The system of claim 1, wherein the instructions are further executable to:

receive a fourth request, from a second care provider device of the one or more additional care provider devices, to view the first insight, and in response, send the first insight to the second care provider device.

5. The system of claim 4, wherein the instructions are further executable to:

receive a fifth request, from the second care provider device, to apply the first insight to one or more patients of the plurality of patients;

in response to the fifth request, determine if a third set of values of one or more patient monitoring parameters of the medical device data meet the first condition and the first scope, and if so, output the first notification for display on a display operably coupled to the second care provider device.

6. The system of claim 1, wherein the instructions are further executable to:

receive an alarm from one of the plurality of medical devices;

determine if the user has selected to receive the alarm; and if the user has selected to receive the alarm, output an indication of the alarm for display on the display operably coupled to the first care provider device.

7. The system of claim 6, wherein the alarm indicates that a value of a patient monitoring parameter of medical device data determined from output of the one of the plurality of medical devices has reached a predetermined condition relative to a threshold.

8. A system, comprising:

a computing device storing instructions executable to:

receive a first insight defined by a user, the first insight including a first function to be applied to medical device data of one or more patients, the first function including a first condition and a first scope of the first condition, the first condition and the first scope defined by the user;

receive real-time medical device data determined from output from a plurality of medical devices monitoring a plurality of patients;

determine if a first set of values of one or more patient monitoring parameters of the medical device data meet the first condition and the first scope, and if so, output a first notification for display on a display operably coupled to a first care provider device associated with the user;

responsive to a first request from the user, adjust a privacy setting of the first insight to allow the first insight to be distributed to one or more additional care provider devices associated with other users, where the first insight is configured to be applied to medical device data of additional patients via the one or more additional care provider devices;

receive a second request, from the first care provider device, to apply a second insight, the second insight including a second function to be applied to medical device data of one or more patients, the second function including a second condition and a second scope of the second condition and a third condition and a third scope of the third condition; and determine if a second set of values of one or more patient monitoring parameters of the medical device data meet the second condition and the second scope and the third condition and the third scope, and if so, output a second notification for display on the display operably coupled to the first care provider device.

9. The system of claim 8, wherein the instructions are further executable to:

receive an alarm from one of the plurality of medical devices;

determine if the user has selected to receive the alarm; and if the user has selected to receive the alarm, output an indication of the alarm for display on the display operably coupled to the first care provider device.

10. The system of claim 9, wherein the alarm indicates that a value of a patient monitoring parameter of medical device data determined from output of the one of the plurality of medical devices has reached a predetermined condition relative to a threshold.

11. The system of claim 8, wherein the instructions are further executable to:

receive a third request, from a second care provider device of the one or more additional care provider devices, to view the first insight, and in response, send the first insight to the second care provider device.

12. The system of claim 11, wherein the instructions are further executable to:

receive a fourth request, from the second care provider device, to apply the first insight to one or more patients of the plurality of patients;

in response to the fourth request, determine if a third set of values of one or more patient monitoring parameters of the medical device data meet the first condition and the first scope, and if so, output the first notification for display on a display operably coupled to the second care provider device.

13. A system, comprising:

a display; and a computing device operably coupled to the display and storing instructions executable to:

output, to the display, real-time medical device data, the real-time medical device data viewable on the display in a graphical user interface (GUI), the real-time medical device data determined from output of one or more medical devices monitoring one or more patients;

output, to the display, a determined result of a first user-selected insight, the first insight including a first function to be applied to the real-time medical device data such that the real-time medical device data is entered as input into the first function, the determined result of the first insight viewable on the display as a tile of the GUI;

receive an indication that a second user-selected insight has been met, the second user-selected insight including a second function defined in part by the first function such that the determined result of the first insight is entered as input into the second function; and output, to the display, a notification responsive to the second user-selected insight being met.

14. The system of claim 13, wherein the real-time medical device data is also entered as input into the second function, and wherein one or both of the first insight and second insight are selected via a second GUI displayed on the display.

15. The system of claim 13, wherein one or both of the first insight and the second insight are defined by a user.

16. The system of claim 15, wherein the second function is defined by the first function, a second parameter selected by the user from a predefined set of parameters, and an operator selected by the user from a predefined set of operators.

17. The system of claim 16, wherein the one or more medical devices includes an anesthesia delivery machine, wherein the determined result of the first function is a current phase of anesthesia delivery from the anesthesia delivery machine, wherein the predefined set of parameters includes each patient monitoring parameter that is able to be determined from the real-time medical device data, and wherein the predefined set of operators includes one or more of and, or, and while.

* * * * *